US008097252B2

(12) United States Patent
McBride et al.

(10) Patent No.: US 8,097,252 B2
(45) Date of Patent: Jan. 17, 2012

(54) METHODS AND COMPOSITIONS FOR ADMINISTERING THERAPEUTIC AND DIAGNOSTIC AGENTS

(75) Inventors: William J. McBride, Boonton, NJ (US); Chien-Hsing Chang, Downingtown, PA (US); David M. Goldenberg, Mendham, NJ (US); Hans J. Hansen, Picayune, MS (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

(21) Appl. No.: 12/985,775

(22) Filed: Jan. 6, 2011

(65) Prior Publication Data
US 2011/0117010 A1 May 19, 2011

Related U.S. Application Data

(62) Division of application No. 12/420,864, filed on Apr. 9, 2009, now Pat. No. 7,892,547, which is a division of application No. 10/768,707, filed on Feb. 2, 2004, now Pat. No. 7,534,431.

(60) Provisional application No. 60/444,357, filed on Jan. 31, 2003.

(51) Int. Cl.
*A61K 39/00* (2006.01)
*A61K 39/44* (2006.01)
*A61K 38/08* (2006.01)
*A61K 39/395* (2006.01)
*A61K 49/06* (2006.01)
*C12P 21/08* (2006.01)
*C07K 16/18* (2006.01)
*C07K 16/22* (2006.01)
*C07K 16/24* (2006.01)

(52) U.S. Cl. ............... 424/136.1; 424/130.1; 424/133.1; 424/134.1; 424/135.1; 424/143.1; 424/145.1; 424/154.1; 424/155.1; 424/158.1; 424/175.1; 424/185.1; 424/1.69; 424/9.3; 424/9.4; 424/9.5; 424/9.6; 435/975; 514/21.9; 530/387.1; 530/387.3; 530/388.1; 530/388.22; 530/388.23; 530/388.24; 530/387.7; 530/388.73; 530/388.75; 530/388.8

(58) Field of Classification Search ........................ None
See application file for complete search history.

(56) References Cited

U.S. PATENT DOCUMENTS

| 5,630,996 | A |  | 5/1997 | Reno et al. |
| 5,914,312 | A | * | 6/1999 | Axworthy et al. ......... 424/133.1 |
| 6,183,744 | B1 |  | 2/2001 | Goldenberg et al. |
| 6,187,287 | B1 |  | 2/2001 | Leung et al. |
| 6,962,702 | B2 |  | 11/2005 | Hansen et al. |
| 7,138,103 | B2 | * | 11/2006 | Goldenberg et al. ......... 424/1.69 |
| 7,151,164 | B2 |  | 12/2006 | Hansen et al. |
| 7,238,785 | B2 |  | 7/2007 | Govindan et al. |
| 7,312,318 | B2 |  | 12/2007 | Hansen et al. |
| 7,521,056 | B2 | * | 4/2009 | Chang et al. ............... 424/192.1 |
| 7,527,787 | B2 | * | 5/2009 | Chang et al. ............... 424/133.1 |
| 7,534,431 | B2 | * | 5/2009 | McBride et al. ............ 424/136.1 |
| 7,560,110 | B2 | * | 7/2009 | Goldenberg et al. ....... 424/133.1 |
| 7,563,433 | B2 | * | 7/2009 | McBride et al. ............. 424/1.89 |
| 7,597,876 | B2 | * | 10/2009 | McBride et al. ............. 424/1.89 |
| 7,776,311 | B1 | * | 8/2010 | McBride et al. ............. 424/1.49 |
| 7,892,547 | B2 | * | 2/2011 | McBride et al. ............ 424/136.1 |
| 2003/0162709 | A1 | * | 8/2003 | Rossi et al. ..................... 514/12 |
| 2004/0018557 | A1 |  | 1/2004 | Qu et al. |
| 2004/0115193 | A1 | * | 6/2004 | Hansen et al. .............. 424/141.1 |
| 2004/0166615 | A1 | * | 8/2004 | Osanai .......................... 438/197 |
| 2009/0246130 | A1 | * | 10/2009 | McBride et al. ............. 424/1.49 |

FOREIGN PATENT DOCUMENTS

| WO | WO 99/66951 | * | 12/1999 |
| WO | WO02082041 |  | 10/2002 |

OTHER PUBLICATIONS

Sharkey et al, Cancer Res 63: 354-363, Jan. 15, 2003.*
Riemer et al, Mol. Immunol. 42: 1121-1124, 2005.*
Yu et al, Investigative Ophthalmology & Visual Science 49(2): 522-527, Feb. 2008.*
Witte et al, Cancer and Metastasis Reviews 17: 155-161, 1998.*
Boerman et al., "Pretargeted Radioimmunotherapy of Cancer: Progress Step by Step", J. Nucl. Med. 44(3):400-411 (2003).
Chang et al., "Molecular Advances in Pretargeting Radioimunotherapy with Bispecific Antibodies", Mol. Cancer Ther. 1(7):553-563 (2002).
Karacay et al., "Pretargeting for Cancer Radioimmunotherapy with Bispecific Antibodies: Role of the Bispecific Antibody's Valency for the Tumor Target Antigen", Bioconjugate Chem. 13:1054-1070 (2002).
Karacay et al., "Development of a Streptavidin-Anti-Carcinoembryonic Antigen Antibody, Radiolabeled Biotin Pretargeting Method for Radioimmunotherapy of Colorectal Cancer. Reagent Development", Bioconjugate Chem. 8:585-594 (1997).
Li et al., "Folate-Mediated Targeting of Antisense Oligodeoxynucleotides to Ovarian Cancer Cells", Pharmaceutical Res. 15(10):1540-1545 (1998).
Mattes et al., "The Advantage of Residualizing Radiolables for Targeting B-Cell Lymphomas with a Radiolabeled Anti-CD22 Monoclonal Antibody", Int. J. Cancer 71:429-435 (1997).
Pawlak-Byczkowska et al., "Two New Monoclonal Antibodies, EPB-1 and EPB-2, Reactive with Human Lymphoma", Cancer Res. 49(16):4568-4577 (1989).
Reddy et al., "Expression and Functional Characterization of the β-Isoform of the Folate Receptor on CD34+ Cells", Blood 93(11):3940-3948 (1999).
Sharkey et al., "A Universal Pretargeting System for Cancer Detection and Therapy Using Bispecific Antibody", Cancer Res. 63(2): 354-363 (2003).

(Continued)

Primary Examiner — Phuong Hyunh
(74) Attorney, Agent, or Firm — Richard A. Nakashima

(57) ABSTRACT

Methods and compositions are described for targeting therapeutic and diagnostic molecules to particular types of cells using targeting antibodies or other targeting moeities.

15 Claims, 9 Drawing Sheets

OTHER PUBLICATIONS

Stein et al., "Comparative Biodistribution and Radioimmunotherapy of Monoclonal Antibody RS7 and its F(ab')2 in Nude Mice Bearing Human Tumor Xenografts", Cancer 73(3):816-823 (1994).

Wang et al., "Folate-mediated targeting of antineoplastic drugs, imaging agents, and nucleic acids to cancer cells", J. Controlled Release 53(1-3):39-48 (1998).

Winkler et al., "Changing the antigen binding specificity by single point mutations of an anti-p24 (HIV-1) antibody", J Immunol. Oct. 15, 2000;165(8):4505-14.

Zhu et al., "Inhibition of tumor growth and metastasis by targeting tumor-associated angiogenesis with antagonists to the receptors of vascular endothelial growth factor", Invest New Drugs. 1999;17(3):195-212.

* cited by examiner

Step 1. Inject hA20 Fab'-c679Fab' producing B-Cell-CD20<-[hA20Fab'-c679Fab']

Step 2. Inject $^{131}$I-IMP 272 producing B-Cell-CD20<-[hA20Fab'-c679Fab']<[$^{131}$I-IMP 272]->[$^{131}$I-IMP 272]->[c679Fab'-hA20Fab']->B-Cell-CD20

SEQUENCE LISTING

<160> NUMBER OF SEQ ID NOS: 2

<210> SEQ ID NO 1
<211> LENGTH: 4
<212> TYPE: PRT
<213> ORGANISM: Artificial
<220> FEATURE:
<223> OTHER INFORMATION: synthetic oligopeptide backbone

<400> SEQUENCE: 1

Lys Tyr Lys Lys
1

<210> SEQ ID NO 2
<211> LENGTH: 4
<212> TYPE: PRT
<213> ORGANISM: Artificial
<220> FEATURE:
<223> OTHER INFORMATION: synthetic oligopeptide backbone

<400> SEQUENCE: 2

Phe Lys Tyr Lys
1

METHODS AND COMPOSITIONS FOR ADMINISTERING THERAPEUTIC AND DIAGNOSTIC AGENTS

CROSS-REFERENCE TO RELATED PATENT APPLICATIONS

This application is a divisional of U.S. application Ser. No. 12/420,864 filed on Apr. 09, 2009 (now U.S. Pat. No. 7,892,547), which was a divisional of U.S. application Ser. No. 10/768,707 (now U.S. Pat. No. 7,534,431), filed Feb. 2, 2004, which claimed the benefit under 35 U.S.C. 119(e) of U.S. Provisional Application No. 60/444,357 (now expired), filed Jan. 31, 2003, each of which is incorporated in its entirety by reference.

BACKGROUND OF THE INVENTION

The present invention relates to the field of administration of therapeutic and diagnostic agents in vivo, including methods and compositions for targeting such agents to particular types of cells.

The information provided herein and references cited are provided solely to assist the understanding of the reader and does not constitute an admission that such information or any of the cited references constitute prior art to the present invention.

The detection of a target site benefits from a high signal-to-background ratio of detection agent. Therapy benefits from as high an absolute accretion of therapeutic agent at the target site as possible, as well as a reasonably long duration of uptake and binding. The targeting ratio and amount of agent delivered to a target site can be improved using targeting vectors comprising diagnostic or therapeutic agents conjugated to a targeting moiety for preferential localization.

Examples of targeting vectors include diagnostic or therapeutic agent conjugates of targeting moieties, such as antibody or antibody fragments, cell- or tissue-specific peptides, and hormones and other receptor-binding molecules. For example, antibodies against different determinants associated with pathological and normal cells, as well as determinants associated with pathogenic microorganisms, have been used for the detection and treatment of a wide variety of pathological conditions or lesions. In these methods, the targeting antibody is directly conjugated to an appropriate detecting or therapeutic agent as described, for example, in Hansen U.S. Pat. Nos. 4,468,457, 4,444,744, 4,460,459, 4,460,561, 4,624,846 and 4,818,709, the disclosures of all of which are incorporated herein by reference.

One problem encountered in direct targeting methods, i.e., in methods in which the diagnostic or therapeutic agent (the "active agent") is conjugated directly to the targeting moiety, is that a relatively small fraction of the conjugate actually binds to the target site, while the majority of conjugate remains in circulation and compromises in one way or another the function of the targeted conjugate. In the case of a diagnostic conjugate, for example, a radioimmunoscintigraphic or magnetic resonance imaging conjugate, non-targeted conjugate which remains in circulation can increase background and decrease resolution. In the case of a therapeutic conjugate having a toxic therapeutic agent, e.g., a radioisotope, drug, or toxin, attached to a long-circulating targeting moiety such as an antibody, circulating conjugate can result in unacceptable toxicity to the host, such as marrow toxicity or systemic side effects.

Pretargeting methods have been developed to increase the target:background ratios of the detection or therapeutic agents. Examples of pre-targeting and biotin/avidin approaches are described, for example, in Goodwin et al., U.S. Pat. No. 4,863,713; Goldenberg, U.S. Pat. No. 5,525,338; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; Sharkey et al., Bioconjugate Chem 8:595-604, 1997; Stickney et al., Cancer Res. 51:6650, 1991; and Yuan et al., Cancer Res. 51:3119, 1991; all of which are incorporated by reference herein in their entireties.

In pretargeting methods, a primary targeting species (which is not bound to a diagnostic or therapeutic agent) is administered. The primary targeting species includes a targeting moiety which binds to the target site and a binding moiety which is available for binding to a binding site on a targetable construct. Once sufficient accretion of the primary targeting species is achieved, a targetable construct is administered. The targetable construct includes a binding site that recognizes the available binding site of the primary targeting species, and a diagnostic or therapeutic agent.

Pretargeting offers certain advantages over the use of direct targeting methods. For example, use of the pretargeting approach for the in vivo delivery of radionuclides to a target site for therapy, e.g., radioimmunotherapy, reduces the marrow toxicity caused by prolonged circulation of a radioimmunoconjugate. This is because the radioisotope is delivered as a rapidly clearing, low molecular weight chelate rather than directly conjugated to a primary targeting molecule, which is often a long-circulating species.

A characteristic encountered with some pretargeting methods is that circulating primary targeting species (primary targeting species which is not bound to the target site) interferes with the binding of the targetable conjugate to targeting species that are bound to the target site (via the binding moiety on the primary targeting species). In some methods, the level of circulating primary targeting species is reduced, such by using a clearing agent that binds to the primary targeting species and facilitates clearing that species from circulation. An example is described in Goodwin, et al., U.S. Pat. No. 4,863,713. However, reducing the level of circulating primary targeting species shifts the binding equilibrium, causing bound primary targeting species (which can be bound with targetable construct) to dissociate from the target, thereby reducing the period of time that the detection or therapeutic species is present at the targeted site.

SUMMARY OF THE INVENTION

The present invention provides advantageous methods for delivering biologically active species and constructs to biological targets. Thus, in one embodiment, the invention concerns improved targeting methods where the binding of a therapeutic or diagnostic agent (or other active species) at a target site is enhanced with an agent that increases the residence of the active species at the target site.

In another embodiment, the present invention concerns improved targeting methods where internalization of an active species or complex is enhanced by binding of a moiety or creation of a complex that is internalized in target cells to a greater extent and/or faster than without such internalization agent.

In a further embodiment, the invention concerns a method for targeted delivery of a therapeutic or diagnostic agent, by administering to a mammal a primary targeting agent that includes at least one target binding moiety and at least one targetable construct binding moiety; a targetable construct that includes at least one primary targeting agent binding moiety, a clearing agent binding moiety, and usually a therapeutic or diagnostic moiety; and a clearing agent that includes at least one targetable construct binding moiety, wherein the clearing agent enhances retention of the targetable construct at a target site.

In another embodiment, the invention provides a method for enhancing cellular internalization of a therapeutic or diagnostic agent, by administering to a mammal a primary targeting agent that includes a target binding moiety; and a separate internalization agent comprising an internalization moiety, where the primary targeting agent forms a complex with the internalization agent thereby enhancing internalization; and the complex also includes a therapeutic or diagnostic moiety.

Likewise, in another aspect, the invention concerns a method for increasing contrast in an in vivo visualization system, by adminstering to a mammal a primary targeting agent that includes a target binding moiety and at least one targetable construct binding moiety; a targetable construct that includes a primary targeting agent binding moiety, a clearing agent binding moiety, and a visualization moiety; and a clearing agent that includes at least one targetable construct binding moiety, thereby reducing the ratio of circulating targetable construct to target bound targetable construct and/or increasing the rate of clearance of circulating target.

The provision of clearing agents as described herein also provides a method for clearing a circulating therapeutic or diagnostic agent by administering a clearing agent to a mammal having a circulating therapeutic or diagnostic agent, where the clearing agent specifically binds to at least one moiety on a circulating molecule or complex that includes the therapeutic or diagnostic agent and enhances clearance of the molecule or complex.

In related aspects, the invention concerns constructs useful in the present methods. Thus, the invention concerns a trispecific targetable construct adapted for delivery of a therapeutic or diagnostic moiety. The construct includes at least one first binding moiety suitable for binding with a separate primary targeting agent; a second binding moiety suitable for binding with a clearing agent; and a third binding moiety suitable for binding with an internalization agent.

Further, the invention provides a clearing agent suitable for clearing a targetable construct from circulation in a mammal. The clearing agent includes a binding moiety suitable for binding a targetable construct; and an internalization moiety.

In another related aspect, the invention provides a molecular complex that includes a targetable construct comprising at least one primary targeting agent binding moiety and an internalizing agent binding moiety, bound with an internalizing agent.

Yet another related aspect concerns a molecular complex that includes a targetable construct that includes at least one, preferably 2, primary targeting agent binding moieties, a clearing agent binding moiety, and a therapeutic or diagnostic moiety, bound with a clearing agent.

A further embodiment is a molecular complex that includes a polyvalent primary targeting agent that includes a target binding moiety and a plurality of targetable construct binding moieties, bound with a polyvalent targetable construct comprising a plurality of primary targeting agent binding moieties; a clearing agent binding moiety, and a therapeutic or diagnostic moiety.

An additional molecular complex includes a primary targeting agent that includes a target binding moiety and at least one targetable construct binding moiety; bound with a targetable construct that includes at least one primary targeting agent binding moiety, a clearing agent binding moiety, and a therapeutic or diagnostic binding moiety; and bound with an internalizing agent that includes a targetable construct binding moiety or a clearing agent binding moiety, and an internalizing moiety.

Yet another complex includes a primary targeting agent that includes a target binding moiety and a therapeutic or diagnostic moiety, bound with an internalization agent comprising a primary targeting agent binding moiety and an internalizing moiety.

In certain embodiments, kits containing the components of the present invention are provided for use in the disclosed methods for targeting therapeutic or diagnostic agents to targeted cell.

In further embodiments, there are provided methods for treating and/or diagnosing a disease or condition in a subject (typically a patient), preferably a human subject. The method involves administering to a subject at least one therapeutic or diagnostic moiety in a targeted delivery method as described herein.

In yet another aspect, the invention provides an advantageous method for preparing DTPA conjugated peptides by synthesis on a solid phase medium, e.g., on a resin. The synthesis is exemplified by the description of the preparation of IMP 272 in the Examples herein.

Additional aspects and embodiments will be apparent from the following Description of the Drawings and the Detailed Description.

BRIEF DESCRIPTION OF THE DRAWINGS

FIG. 6 illustrates a B Cell with CD20 on its surface. FIG. 7 illustrates the binding of primary targeting agent to the cell surface markers shown in FIG. 6. FIG. 8 illustrates targetable construct bound to the localized primary targeting agents from FIG. 7, with each targetable construct crosslinking two localized primary targeting agents. FIG. 9 illustrates the binding of bi-valent clearing agent to localized targetable constructs, crosslinking two targetable constructs, and thereby forming a complex involving binding to 4 targets.

DETAILED DESCRIPTION OF THE PREFERRED EMBODIMENTS

Figure 1:
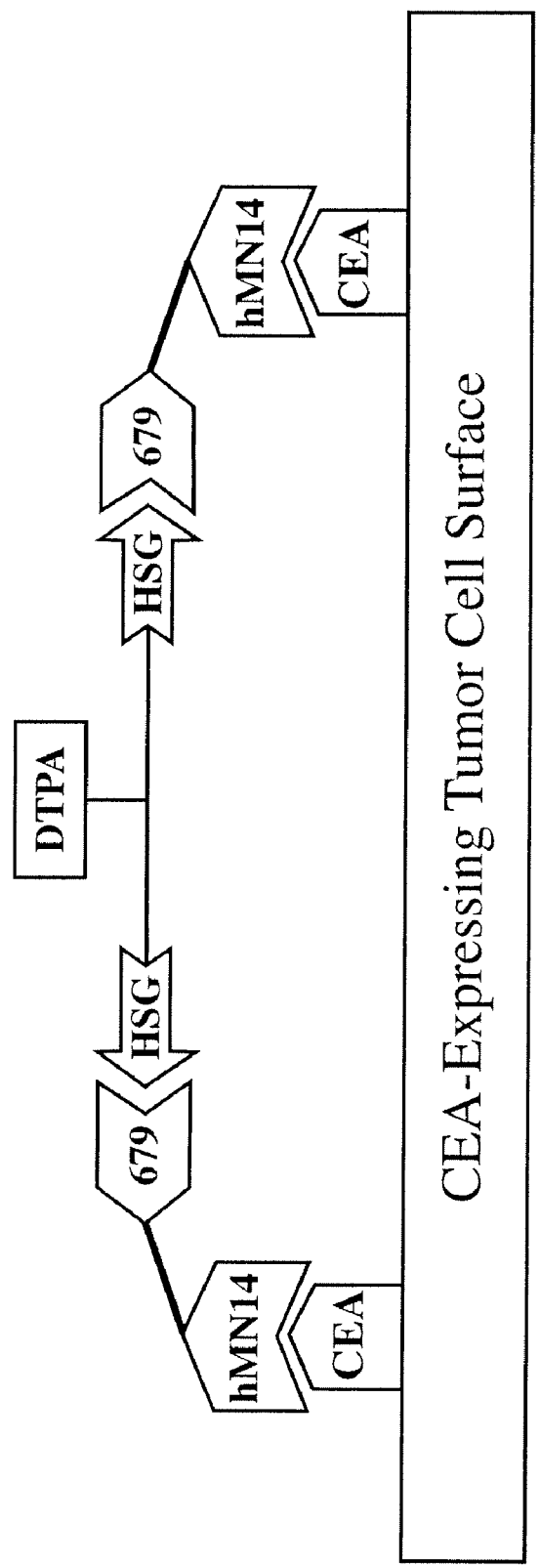
FIG. 1 is a schematic diagram illustrating pretargeting, with a primary targeting agent having a hMN14 Ab moiety that binds to CEA on a tumor cell, and a 679 Ab moiety that binds to the hapten, HSG on a targetable construct. The targetable construct has orthogonal haptens HSG (2 copies) and DTPA (1 copy), such that the targetable construct is bound to two target-bound primary targeting agents, and the DTPA moiety is free for binding to a clearing agent.
Figure 2:
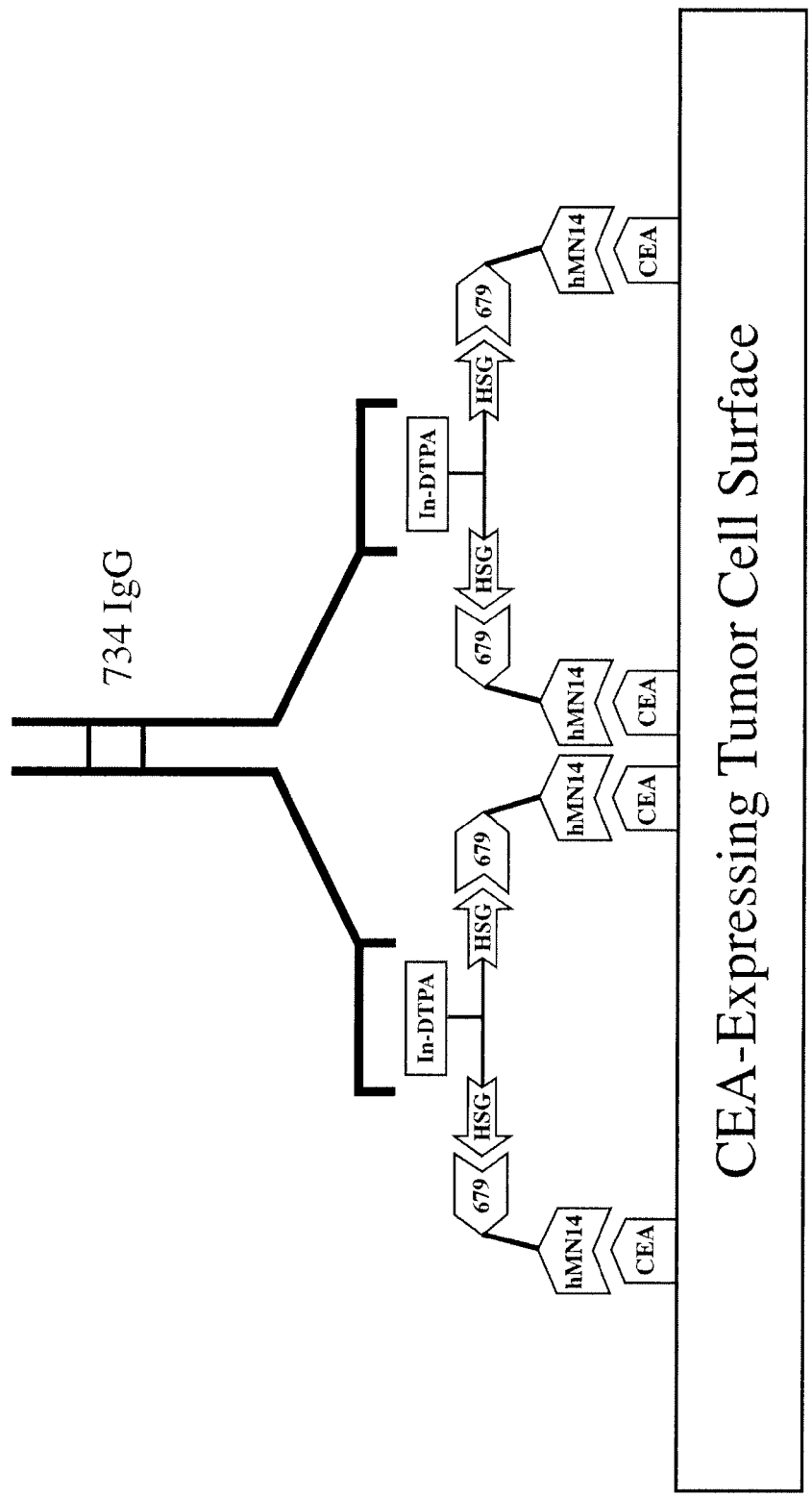
FIG. 2 is a schematic diagram showing the pretargeting of FIG. 1, with crosslinking of two target-bound complexes with a clearing agent that has a 734 IgG Ab that binds to an InDTPA hapten on each of two targetable constructs, thereby enhancing retention of targetable construct at the target site. As shown, this combination of targetable construct and clearing agent result in a complex crosslinking 4 target sites.

Unless otherwise specified, "a" or "an" means "one or more."

I. Definitions

In the description that follows, a number of terms are used and the following definitions are provided to facilitate the understanding of the present invention. Unless otherwise defined, all technical and scientific terms used have the same meaning as commonly understood by one of ordinary skill in the art. In addition, the contents of all references cited herein are incorporated by reference in their entirety.

As used herein, the term "primary targeting agent" refers to at least a bispecific construct, containing at least one binding moiety that binds with a selected target, and at least one (preferably 2) binding moiety that binds with a targetable construct. As used herein, the term "bispecific antibody", is an antibody capable of binding to two different moieties, e.g., a targeted tissue and a targetable construct. The bispecific antibody can bind simultaneously to two targets which are of different structure. Bispecific antibodies (bsAb) and bispecific antibody fragments (bsFab) have at least one arm that specifically binds to, for example, a tumor, a tissue, a B-cell, T-cell, myeloid-, plasma-, and mast-cell antigen or epitope and at least one other arm that specifically binds to a targetable construct. A variety of bispecific antibody fusion proteins can be produced using molecular engineering. A bispecific antibody fusion protein is a recombinantly produced antigen-binding molecule in which two or more for the same or different single-chain antibody or antibody fragment segments with the same or different specificities are linked. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with a binding site for one antigen and two scFv with two binding sites for a second antigen. In another form, a diabody, which is a dimeric antibody fragment, is useful in the present invention. A diabody is composed of a heavy-chain variable domain (VH) and is linked to a light-chain variable domain (VL) by a peptide linker. Unlike single-chain (sc) Fv fragments, each antigen-binding site is formed by pairing of one VH and one VL domain from two different polypeptides. Diabodies have two antigen-binding sites, and can be bispecific, and are useful in the present invention as a primary targeting agent.

The primary targeting agent also can be a multispecific antibody, which is an antibody that can bind simultaneously to at least two targets that are of different structure, e.g., two different antigens, two different epitopes on the same antigen, or a hapten and/or an antigen or epitope. For example, one specificity would be for a B-cell, T-cell, myeloid-, plasma-, and mast-cell antigen or epitope. Another specificity could be to a different antigen on the same cell type, such as CD20, CD19, CD21, CD23, CD46, CD80, HLA-DR, CD74, and CD22 on B-cells. A multivalent antibody is an antibody that can bind simultaneously to at least two targets that are of the same or different structure. Multispecific, multivalent antibodies are constructs that have more than one binding site of different specificity. For example, a diabody can react with one binding site with one antigen and the other binding site with another antigen.

Further, the primary targeting agent can be an antibody or an antibody fusion protein that is a recombinantly produced antigen-binding molecule in which two or more of the same or different single-chain antibody or antibody fragment segments with the same or different specificities are linked. Valency of the fusion protein indicates how many binding arms or sites the fusion protein has to a single antigen or epitope; i.e., monovalent, bivalent, trivalent or multivalent. The multivalency of the antibody fusion protein means that it can take advantage of multiple interactions in binding to an antigen, thus increasing the avidity of binding to the antigen. Specificity indicates how many antigens or epitopes an antibody fusion protein is able to bind; i.e., monospecific, bispecific, trispecific, multispecific. Using these definitions, a natural antibody, e.g., an IgG, is bivalent because it has two binding arms but is monospecific because it binds to one epitope. Monospecific, multivalent fusion proteins have more than one binding site for an epitope but only binds with one epitope, for example a diabody with two binding sites reactive with the same antigen. The fusion protein may comprise a single antibody component, a multivalent or multispecific combination of different antibody components or multiple copies of the same antibody component. The fusion protein may additionally comprise an antibody or an antibody fragment and a therapeutic agent. Examples of therapeutic agents suitable for such fusion proteins include immunomodulators ("antibody-immunomodulator fusion protein") and toxins ("antibody-toxin fusion protein").

The primary targeting agent may specifically bind a variety of antigens or target via its target binding moiety. However, particular suitable antigens include carcinoembryonic antigen, tenascin, epidermal growth factor receptor, platelet derived growth factor receptor, fibroblast growth factor receptors, vascular endothelial growth factor receptors, gangliosides, HER/2neu receptors, and mixtures thereof. More specifically, the antigen may be selected from colon-specific antigen-p (CSAp), carcinoembryonic antigen (CEA), also known as CD66e, CD4, CD5, CD8, CD14, CD15, CD19, CD20, CD21, CD22, CD23, CD25, CD30, CD33, CD37, CD38, CD40, CD40L, CD45, CD46, CD52, CD66a-d, CD74, CD75, CD80, CD126, B7, HLA-DR, Ia, Ii, HM1.24, MUC 1, MUC 2, MUC 3, MUC 4, NCA, EGFR, HER 2/neu, PAM-4, TAG-72, EGP-1, EGP-2, AFP, HCG, HCG-beta, PLAP, PAP, histone, A3, KS-1, Le(y), S100, PSMA, PSA, tenascin, folate receptor, VEGF, PlGF, ILGF-1 (insulin-like growth factor-1), necrosis antigens, IL-2, IL-6, T101, MAGE, organotropic hormones, oncogene products, cytokeratin, and combinations thereof.

A "targetable construct" comprises a molecular scaffold which comprises or bears at least two orthogonal binding moieties recognized respectively by a binding moiety of a primary targeting agent and a binding moiety of a clearing agent. As used herein, a "molecular scaffold" (or simply "scaffold") is any chemical structure to which epitopes and other binding moieties can be attached at a variety of positions, and/or with a variety of orientations, relative to the scaffold and/or other moieties. Non-limiting examples of molecular scaffolds include polymers such as oligopeptides and oligonucleotides. See Skerra, Engineered protein scaffolds for molecular recognition. *J Mol Recognit* 13(4):167-187, 2000; Erratum in: *J Mol Recognit* 14(2):141, 2001.

As used herein a "clearing agent" is a construct that enhances clearance of unbound targetable construct from circulation and/or locks targetable construct to primary targeting agent. Preferably, the clearing agent has physical properties, such as size, charge, configuration or combinations thereof, that limit clearing agent access to the population of target cells recognized by a targetable construct used in the same treatment protocol as the clearing agent. This enhancement may be further improved by the administration of an anti-idiotypic clearing agent, such as an anti-idiotypic monoclonal antibody specific for the determinant of the primary targeting agent, which binds to the target site. The clearance effect may be further enhanced by using a galactosylated clearing agent, because a galactosylated clearing agent is rapidly cleared through the liver. Likewise, a clearing agent can include a rapidly clearing antibody, such as an antibody having mutations that enhance clearance. The clearing agent may be an IgG, and more preferably, an IgG 1, which if it fixes complement, would be cleared rapidly from the patient. For the present invention, clearing agents are also configured to cross-link separate target-bound targetable constructs.

As used herein, the term "pathogen" includes, but is not limited to fungi, viruses (e.g., human immunodeficiency virus (HIV), herpes virus, cytomegalovirus, rabies virus, influenza virus, hepatitis B virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus and blue tongue virus), parasites and bacteria (e.g., *Streptococcus agalactiae, Legionella pneumophilia, Streptococcus pyogenes, Escherichia coli, Neisseria gonorrhoeae, Neisseria meningitidis, Pneumococcus, Hemophilis influenzae* B, *Treponema pallidum,* Lyme disease spirochetes, *Pseudomonas aeruginosa, Mycobacterium leprae, Brucella abortus, Mycobacterium tuberculosis* and Tetanus toxin). See U.S. Pat. No. 5,332,567. Additional pathogens are listed in the Detailed Description.

As used herein, the term "antibody" refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An "antibody fragment" is a portion of an antibody such as F(ab')$_2$ F(ab)$_2$, Fab', Fab, Fv, sFv and the like. Regardless of structure, an antibody fragment binds with the same antigen that is recognized by the intact antibody. For example, an anti-CEA monoclonal antibody fragment binds with an epitope of CEA.

The term "antibody fragment" also includes any synthetic or genetically engineered protein that acts like an antibody by binding to a specific antigen to form a complex. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker ("sFv proteins"), and minimal recognition units consisting of the amino acid residues that mimic the hypervariable region.

The term "scFV" is used to mean a recombinant single chain polypeptide molecule in which light and heavy chain variable regions of an antibody are connected by a peptide linker. Single chain antibodies (scFv) generally do not include portions of the Fc region of antibodies that are involved in effector functions and are thus naked antibodies, although methods are known for adding such regions to known scFv molecules if desired. See Helfrich et al., A rapid and versatile method for harnessing scFv antibody fragments with various biological functions. *J Immunol Methods* 237: 131-145 (2000) and de Haard et al., Creating and engineering human antibodies for immunotherapy. *Advanced Drug Delivery Reviews* 31:5-31 (1998).

The term "IgG" is used to mean an antibody protein generated against, and capable of binding specifically to an antigen.

As used herein in relation to rapidly clearing mutant antibodies, the term "parent antibody" is used to mean an antibody which is similar to a mutant antibody in every way except that the Fc-hinge fragment of the IgG component in the parent antibody does not contain one or more amino acid mutations in the $C_H2$-$C_H3$ domain interface region. As used herein, the term "Fc-hinge" comprises the Cl, CH1, hinge, CH2 and CH3 regions of an IgG.

A "chimeric antibody" is a recombinant protein that contains the variable domains and complementary determining regions derived from a rodent antibody, while the remainder of the antibody molecule is derived from a human antibody.

The term "humanized antibodies" refers to antibodies that have been modified, by genetic manipulation and/or in vitro treatment to be more human-like in terms of amino acid sequence, glycosylation pattern, etc., in order to reduce the antigenicity of the antibody or antibody fragment in an animal to which the antibody is intended to be administered, usually in a human. See Gussow & Seemann, Humanization of monoclonal antibodies. *Methods Enz.* 203:99-121 (1991), and Vaswani & Hamilton, Humanized antibodies as potential therapeutic drugs. *Ann Allergy Asthma Immunol* 81:105-119 (1998). In many cases, humanized antibodies are recombinant proteins in which murine complementarity determining regions of a monoclonal antibody have been transferred from heavy and light variable chains of the murine immunoglobulin into a human variable domain. Alternatively, fully human antibodies can be obtained from transgenic non-human animals. See, e.g., Mendez et al., *Nature Genetics,* 15: 146-156 (1997); U.S. Pat. No. 5,633,425, which are incorporated herein by reference in their entireties. The primary target agent and the clearing agent can be composed of murine, chimeric, humanized, human antibodies as described above or combinations thereof.

As used herein in connection with binding moeities, the term "orthogonal" means that two or more binding moieties indicated to be orthogonal to each other do not bind at a significant level to the same complementary binding pair member, i.e., they recognize different epitopes on different molecules.

A "hapten" is a small molecule that cannot provoke an immune response unless first bound to an immunogenic carrier molecule. Although a hapten cannot itself provoke an immune response, it is specifically bound by antibodies generated during an immunogenic response to the hapten-carrier conjugate.

Figure 9:
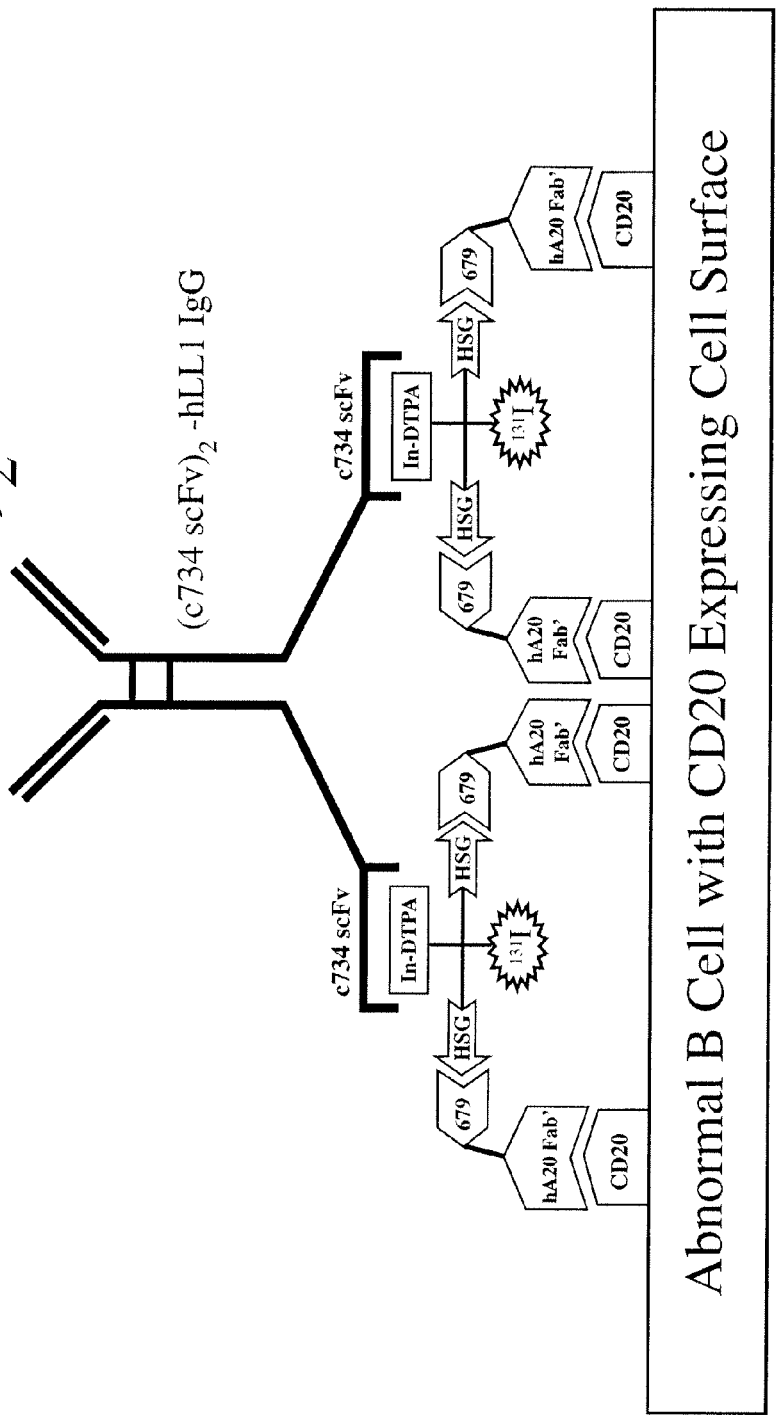

As used herein, a "therapeutic agent" is a molecule or atom which is conjugated to a primary targeting moiety, such as an antibody moiety, or conjugated to a targetable construct, or fused to the primary targeting agent, with for example, RNAse or a toxin, to produce a conjugate which is useful for therapy. Non-limiting examples of therapeutic agents include drugs, prodrugs, toxins, enzymes, enzymes that activate prodrugs to drugs, enzyme-inhibitors, nucleases, hormones, hormone antagonists, immunomodulators, e.g., cytokines, i.e, interleukins, such as interleukin-2, lymphokines, interferons and tumor necrosis factor, oligonucleotides (e.g., antisense oligonucleotides or interference RNAs, i.e., small interfering RNA (siRNA)), chelators, boron compounds, photoactive agents or dyes, radioisotopes or radionuclides. The LL1 scv734 IgG is an example of a locking antibody which is also a binding molecule as shown in FIG. 9 of the present application.

Suitable additionally administered drugs, prodrugs, and/or toxins may include aplidin, azaribine, anastrozole, azacytidine, bleomycin, bortezomib, bryostatin-1, busulfan, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin and analogs thereof, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, semustine streptozocin, tamoxifen, taxanes, taxol, testosterone propionate, thalidomide, thioguanine, thiotepa, teniposide, topotecan, uracil mustard, vinblastine, vinorelbine, vincristine, ricin, abrin, ribonuclease, ribonuclease, such as onconase, rapLR1, DNase I, Staphylococcal enterotoxin-A, pokeweed antiviral protein, gelonin, diphtheria toxin, *Pseudomonas* exotoxin, *Pseudomonas* endotoxin, nitrogen mustards, ethyleneimine derivatives, alkyl sulfonates, nitrosoureas, triazenes, folic acid analogs, anthracyclines, COX-2 inhibitors, pyrimidine analogs, purine analogs, antibiotics, epipodophyllotoxins, platinum coordination complexes, vinca alkaloids, substituted ureas, methyl hydrazine derivatives, adrenocortical suppressants, antagonists, endostatin or combinations thereof.

Suitable radionuclides may include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{75}$Se, $^{77}$As, $^{86}$Y, $^{89}$Sr, $^{89}$Zr, $^{90}$Y, $^{94}$Tc, $^{94m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$Pb $^{212}$Bi, $^{212}$Pb, $^{213}$Bi, $^{223}$Ra, $^{225}$Ac, or mixtures thereof. If the radionuclide is to be used therapeutically, it may be desirable that the radionuclide emit 70 to 700 keV gamma particles or positrons. If the radionuclide is to be used diagnostically, it may be desirable that the radionuclide emit 25-4000 keV gamma particles and/or positrons. The radionuclide may be used to perform positron-emission tomography (PET), and the method may include performing PET.

Suitable enzymes that may be administered with the primary therapeutic agent may include carboxylesterases, glucuronidases, carboxypeptidases, beta-lactamases, phosphatases, nucleases, proteases, lipases, and mixtures thereof.

Suitable photoactive agents and dyes, include agents for photodynamic therapy, such as a photosensitizer, such as benzoporphyrin monoacid ring A (BPD-MA), tin etiopurpurin (SnET2), sulfonated aluminum phthalocyanine (AlSPc) and lutetium texaphyrin (Lutex).

As used herein, a "diagnostic agent" is a molecule or atom which is conjugated to a primary targeting moiety, such as an antibody moiety or conjugated to a targetable construct to produce a conjugate, which is useful for diagnosis. Non-limiting examples of diagnostic agents include a photoactive agent or dye, a radionuclide, a radioopaque material, a contrast agent, a fluorescent compound, an enhancing agent (e.g., paramagnetic ions) for magnetic resonance imaging (MRI) and combinations thereof. Suitable enhancing agents are Mn, Fe and Gd. U.S. Pat. No. 6,331,175 describes MRI technique and the preparation of antibodies conjugated to a MRI enhancing agent and is incorporated in its entirety by reference. One or more enhancing agents can be useful for ultrasound imaging.

Suitable radionuclides for use in diagnosis, wherein the diagnostic agent emits 25 to 4000 keV gamma particles and/or positrons are $^{18}$F, $^{32}$P, $^{45}$Ti, $^{52}$Fe, $^{62}$Cu, $^{64}$Cu, $^{67}$Cu, $^{67}$Ga, $^{68}$Ga, $^{86}$Y, $^{89}$Zr, $^{90}$Y, $^{94m}$Tc, $^{94}$Tc, $^{99m}$Tc, $^{111}$In, $^{123}$I, $^{124}$I, $^{125}$I, $^{131}$I, $^{154-158}$Gd, $^{177}$Lu, $^{188}$Re, or mixtures thereof. Further, suitable radionuclides for use in diagnosis, wherein the diagnostic agent emits 60 to 700 keV gamma particles and/or positrons are $^{18}$F, $^{52}$Fe, $^{62}$Cu, $^{64}$Cu, $^{67}$Cu, $^{67}$Ga, $^{90}$Y, $^{111}$Ag, $^{111}$In, $^{125}$I, $^{131}$I, $^{142}$Pr, $^{153}$Sm, $^{161}$Tb, $^{166}$Dy, $^{166}$Ho, $^{177}$Lu, $^{186}$Re, $^{188}$Re, $^{189}$Re, $^{211}$At, $^{212}$Bi, $^{212}$Pb, $^{213}$Bi, $^{223}$Ra, $^{225}$Ac, or mixtures thereof. The radioisotope is used to perform positron-emission tomography (PET).

The therapeutic and/or diagnostic agent may be directly associated with the primary therapeutic agent (e.g., covalently or non-covalently bound thereto). Preferably, the diagnostic agents are selected from the group consisting of radioisotopes, enhancing agents for use in magnetic resonance imaging, and fluorescent compounds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose.

As used herein, the term "tissue" is used to mean a tissue as one of ordinary skill in the art would understand it to mean. As envisioned in the current application, tissue is also used to mean individual cells, groups of cells, or cell cultures, of a bodily tissue or fluid (e.g., blood cells). Furthermore, the tissue may be within a subject, or biopsied or removed from a subject. The tissue may also be a whole or any portion of a bodily organ. Additionally, the tissue may be "fresh" in that the tissue would be recently removed from a subject without any preservation steps between the excision and the methods of the current invention. The tissue may also have been preserved by such standard tissue preparation techniques including, but not limited to, freezing, quick freezing, paraffin embedding and tissue fixation, prior to application of the methods of the current invention. Exemplary tissues include, but are not limited to, tissues from the ovary, thymus, parathyroid, and spleen.

As used herein, the term "targeted tissue" or "target" is any biological entity, e.g., a system, organ, tissue, cell, organelle, receptor, surface antigen, clot, infarct, atherosclerotic plaques, transmembrane protein or secreted polypeptide to which a targetable construct is preferentially delivered. The term "delivered" encompasses being contacted with, bound to, and/or internalized by, a targeted tissue. For example, in therapeutic aspects of the invention, the targeted tissue is often infected, inflamed, malignant, dysfunctional or displaced or ectopic (e.g., infected cells, cancer cells, endometriosis, etc.).

As used herein, the term "epitope" (a.k.a. immunogenic recognition moiety) encompasses any molecule or moiety that is specifically bound by a recognition moiety or molecule. Non-limiting examples of recognition moieties and molecules include antibodies, antibody derivatives, antigen-binding regions and minimal recognition units of antibodies, and receptor-specific ligands.

As used herein, the term "subject" refers to any animal (i.e., vertebrates and invertebrates) including, but not limited to humans and other primates, rodents (e.g., mice, rats, and guinea pigs), lagamorphs (e.g., rabbits), bovines (e.g, cattle), ovines (e.g., sheep), caprines (e.g., goats), porcines (e.g., swine), equines (e.g., horses), canines (e.g., dogs), felines (e.g., cats), domestic fowl (e.g., chickens, turkeys, ducks, geese, other gallinaceous birds, etc.), as well as feral or wild animals, including, but not limited to, such animals as ungulates (e.g., deer), bear, fish, lagamorphs, rodents, birds, etc. It is not intended that the term be limited to a particular age or sex. Thus, adult and newborn subjects, as well as fetuses, whether male or female, are encompassed by the term.

II. General Methods, Agents, Constructs, Complexes And Kits Of The Invention

The present invention concerns methods for delivering an active species, such as a diagnostic or therapeutic agent to a target site. In general, the methods involve pre-targeting a primary targeting agent to the desired target. A targetable construct is administered, that binds to the primary targeting agent and carries the active species. A clearing agent is administered that "locks" bound targetable construct in place, and rapidly clears unbound targetable construct. "Locking" the bound targetable construct at the target binding site occurs because the binding equilibrium for targetable construct to primary targeting agent is shifted toward the bound state, generally by cross-linking two or more bound targetable constructs. In this way, removing the active species on circulating targetable construct from circulation causes less dissociation of targetable construct from the target site as would otherwise occur.

Thus, typically the clearing agent has a dual function. For the "lock" function, the clearing agent typically "locks" the targetable construct in place by cross-linking two or more adjacent constructs. At the same time, the binding between targetable construct and primary targeting agent is generally selected to be highly stable, typically be utilizing two or more binding moieties for each targetable construct. For the clearing function, the clearing agent can be selected to have a desired clearance time to reduce general tissue exposure (non-targeted) to the active species. Often a rapidly removed clearing agent is selected, for example, an IgG molecule with a mutation that increases clearance rate, or an antibody modified to provide a galactosylated antibody. In this way, the clearing agent reduces general tissue exposure to the active species, while at the same time reducing the dissociation of targetable construct containing active species at the target site. As a result, the method provides higher concentrations of active species at the target and/or provides longer exposure times due to the stabilization of the binding of the targetable construct at the target site.

In a further embodiment, the present invention concerns the targeting of therapeutic or diagnostic agents to particular sites in vivo in a mammal by using pre-targeting, with rapid clearing of non-localized active species. In this way, the primary targeting species, also referred to as the localization agent remains in equilibrium because the localization agent is not cleared from circulation. Instead, non-bound targetable conjugate bearing the active species is cleared, thereby reducing the exposure of non-target sites to the active species. The targetable conjugate is cleared using a clearing agent that binds to the targetable construct, causing its removal. The clearing agent is highly preferably constructed so that it also functions as a "locking" species, fixing the targetable conjugate to the localization agent. In this way, the clearing of the targetable construct does not result in the dissociation of substantial amounts of targetable construct from localization agent bound at the target sites.

In a further embodiment, the invention concerns a method for targeted delivery of a therapeutic or diagnostic agent, by administering to a mammal a primary targeting agent that includes at least one target binding moiety and at least one targetable construct binding moiety; a targetable construct that includes at least one primary targeting agent binding moiety, a clearing agent binding moiety, and usually a therapeutic or diagnostic moiety; and a clearing agent that includes at least one targetable construct binding moiety, wherein the clearing agent enhances retention of the targetable construct at a target site. The components are configured such that the clearing agent binds to the targetable construct (and can also bind to primary targeting agent) resulting in stabilized binding of targetable construct at the binding site as compared to binding of targetable construct to primary targeting agent alone or with clearing agent that does not stabilize targetable construct at the target binding site. In most cases, such stabilization is accomplished by cross-linking two or even more targetable constructs at the binding site.

In certain embodiments of primary targeting agent, the target binding moiety is an antibody; the primary targeting agent includes a plurality of target binding moieties, e.g., 2,3, or 4; a targetable construct binding moiety is an antibody or an antigen-binding fragment thereof; a targetable construct binding moiety is a hapten; a targetable construct binding moiety is a member of a specific binding pair; the primary targeting agent includes a plurality of targetable construct binding moieties, e.g. 2; the primary targeting agent targets a cancer cell; the primary targeting agent targets a tissue; the primary targeting agent targets a pathogen; a target binding antibody and/or targetable construct binding antibody is an IgG antibody (which can be an antibody fragment).

In embodiments of targetable constructs, the primary targeting agent binding moiety is orthogonal to the clearing agent binding moiety, such as orthogonal haptens; the targetable construct includes 2 primary targeting agent binding moieties; the targetable construct includes 2 primary targeting agent binding moieties and a clearing agent binding moiety; the targetable construct includes a therapeutic agent; the targetable construct includes diagnostic agent; the primary targeting agent binding moiety is an antibody or a hapten; the clearing agent binding moiety is an antibody or a hapten; both the primary targeting agent binding moiety and the clearing agent binding moiety are antibodies or are haptens; the primary targeting agent binding moiety and the clearing agent binding moiety are members of respective specific binding pairs.

In particular embodiments of clearing agent, the clearing agent includes at least 2 targetable construct binding moieties; the targetable construct binding moiety(ies) is an antibody or an antigen-binding fragment thereof, the targetable construct binding moiety(ies) are haptens; the targetable construct binding moiety(ies) is a member of a specific binding pair; a targetable construct binding antibody of the clearing agent includes an IgG antibody (which may be a fragment); an IgG antibody is modified such that the antibody and associated clearing agent is cleared more rapidly from circulation than the parent antibody without such modification; the IgG modification can include one or more amino acid changes and/or deletions; an IgG deletion includes a $C_H2$ domain deletion; a clearing agent antibody includes attached galactose; the clearing agent binds with a plurality of targetable constructs, e.g., 2 or 3; binding of clearing agent to targetable construct bound to target bound primary targeting agent stabilizes binding (increases time targetable construct remains bound) of targetable construct at the target site; binding of clearing agent to targetable construct that is not bound at a target site increases the rate of clearance of targetable construct from circulation.

In certain embodiments of the method, the primary targeting agent includes a targetable construct binding antibody construct and a target binding antibody construct; the targetable construct includes at least 2 copies of a hapten that binds with the targetable construct binding antibody construct, and a hapten that binds with a clearing agent antibody construct; and the clearing agent includes a targetable construct binding antibody construct that binds with at least 2 targetable constructs.

In some cases, it is not necessary for the clearing agent to rapidly clear the targetable construct, so essentially the locking function is sufficient. This is particularly applicable where the targetable construct is itself rapidly clearing. In such a system, targetable construct binds to primary targeting agent and is "locked" at the target sites as unbound targetable construct clears from circulation. Thus, the present invention also includes the use of cross-linking clearing agents that are not rapidly clearing.

Many applications of the invention involve cell surface localization or targeting. However, the general methods of this invention can also be extended to include internalization of the active species in cells. In these embodiments, the methods utilize constructs that incorporate an internalization moiety that causes the cell to internalize an associated complex. Such an internalization moiety can be associated with various constructs, such as forming a part of the clearing agent, or part of a separate internalization agent that binds to a targetable construct or to a clearing agent. In this regard, the invention concerns an approach for internalizing complexes, e.g., complexes that include therapeutic or diagnostic agents, into target cells. The approach involves targeting or pretargeting a localization agent to a target, and adding an internalization agent that enhances cellular internalization of the associated complex. In this way, targeted internalization occurs instead of the non-specific internalization that would occur by use of the internalization agent without the localization agent. This approach can be used in conjunction with the pretargeting methods described herein, or in other targeting methods. The localization agent can, for example, be one of the components of the basic targeting method, or can be a separate agent that binds to one more of those components.

In particular, the invention provides a method for enhancing cellular internalization of a therapeutic or diagnostic agent, by administering to a mammal a primary targeting agent that includes a target binding moiety; and a separate internalization agent comprising an internalization moiety, where the primary targeting agent forms a complex with the internalization agent thereby enhancing internalization; and the complex also includes a therapeutic or diagnostic moiety. The therapeutic or diagnostic moiety can be part of the primary targeting agent.

In preferred embodiments, the internalization moiety binds to or is part of the targetable construct or the clearing agent. Thus, in certain embodiments, the method also includes administering to the mammal a targetable construct that includes a primary targeting agent binding moiety and a clearing agent binding moiety, and a clearing agent that includes a targetable construct binding moiety and an internalization moiety. Alternatively, the clearing agent can include an internalization agent binding moiety, and an internalization agent that includes a clearing agent binding moiety is also administered. Likewise in certain embodiments, the method includes administering to the mammal a targetable construct that includes a primary targeting agent binding moiety, an internalization agent binding moiety and a clearing agent binding moiety; a clearing agent that includes a targetable construct binding moiety; and an internalization agent that includes a targetable construct binding moiety and an internalization moiety. Use of a separate internalization agent can be advantageous by allowing association of internalization moiety with targetable construct only or preferentially at the binding site.

For aspects of the present invention that involve an internalization moiety, internalization can be accomplished in various ways. In particular embodiments, the internalization moiety binds to a recycling receptor, such as a folate receptor. For binding to a folate receptor, the internalization moiety can, for example, include folate or methotrexate, or a folate analog binding to a folate receptor. In other embodiments, the internalization moiety includes a peptide that enhances non-receptor mediated internalization, such as the HIV-1 tat protein, transportan, MAP (model amphipathic peptide), antennapedia peptide, also known as penetratin, and proteins or peptides that are known to internalize moieties to which they are attached. Nagahara et al., *Nature Medicine*, 4(12):1449 1998 discloses the use of tat in fusion proteins. Other cell penetrating peptides are known in the prior art and are disclosed in Thoren et al., *FEBS Letters* 482: 265-268 (2000); Mazel et al., *Anti-Cancer Drugs* 12: 107-116 (2001); Hallbrink et al., *Biochim. et Biophys. Acta* 1515: 101-109 (2001); Thoren et al., *Biochem. Biophys. Res. Commun.* 307: 100-107 (2003). The method can utilize constructs as described above, and/or involve internalization agents or internalization moieties as described herein.

In aspects of the invention that includes a diagnostic or therapeutic moiety, such diagnostic or therapeutic moiety can be of many different types. For example, a therapeutic moiety can be or include a photoactive agent, a radioactive isotope, a non-radioactive metal chelate, a drug, an enzyme for activating a prodrug, prodrug, and/or a toxin. Similarly, a diagnostic moiety can be or include, for example, a contrast agent, a light scattering metal colloid particle; a radioactive isotope, and/or a radioimaging metal chelate.

In this cellular internalization enhancing method the targetable construct binding moiety of the clearing agent comprises an antibody or an antigen binding antibody fragment thereof, and more particularly wherein the antibody or fragment thereof is an IgG antibody or fragment thereof. More particularly the antibody or antibody fragment there of is an antibody with a $C_H2$ deletion that enhances clearance from circulation. The antibody or antibody fragment can also be modified with galactose to enhance clearance.

Further the internalization enhancement method utilizes a clearing agent that binds with a plurality of targetable constructs. Further, the clearing agent to targetable construct stabilizes binding of targetable construct to primary targeting agent at binding sites and enhances clearance of targetable construct not bound to primary targeting agent at binding sites. The targetable construct binding moiety of the clearing agent comprises an antibody or antibody fragment, particularly an IgG antibody or antibody fragment. The antibody or antibody fragment is an IgG antibody with a $C_H2$ deletion that enhances clearance from circulation or an antibody or antibody fragment that is modified with galactose.

Further, the invention discloses a method for increasing contrast in an in vivo visualization system, by adminstering to a mammal a primary targeting agent that includes a target binding moiety and at least one targetable construct binding moiety; a targetable construct that includes a primary targeting agent binding moiety, a clearing agent binding moiety, and a visualization moiety; and a clearing agent that includes at least one targetable construct binding moiety, thereby reducing the ratio of circulating targetable construct to target bound targetable construct and/or increasing the rate of clearance of circulating target. The clearing agent further comprises an internalization moiety. The targetable construct further comprises an internalization agent binding moiety, and the method further comprises administering to the mammal an internalization agent comprising a targetable construct binding moiety and an internalization moiety. In an embodiment, the targetable construct binding moiety of the clearing agent comprises an antibody or antibody fragment, which preferably is an IgG antibody or antibody fragment. The IgG antibody with a $C_H2$ deletion that enhances clearance from circulation or is modified with galactose. The clearing agent may bind with a plurality of targetable constructs. Further, the binding of the clearing agent to the targetable construct stabilizes binding of targetable construct to primary targeting agent at binding sites and enhances clearance of targetable construct not bound to primary targeting agent at binding sites.

The present invention also encompasses a method for clearing a circulating therapeutic or diagnostic agent by administering a clearing agent to a mammal having a circulating therapeutic or diagnostic agent, where the clearing agent specifically binds to at least one moiety on a circulating molecule or complex that includes the therapeutic or diagnostic agent and enhances clearance of the molecule or complex. The method can involve targetable constructs and/or clearing agents as described herein.

In particular embodiments, the therapeutic or diagnostic agent is part of a targetable construct that includes at least 2 orthogonal haptens, preferably at least 2 copies of an orthogonal hapten; the targetable construct includes a peptide, preferably as a scaffold or linker; therapeutic agent is a radioisotope, a drug, a toxin, an enzyme that activates a prodrug, a non-radioactive metal chelate, or an immunostimmulatory agent. In the method the clearing agent comprises an antibody or antibody fragment that specifically binds to the circulating molecule or complex. The clearing agent can bind at least two circulating molecule or complex, thereby resulting in crosslinking of the molecules or complexes. The clearing agent is as described above, an IgG or a fragment, or an IgG antibody with a $C_H2$ deletion that enhances clearance from circulation or is modified with galactose. The clearing agent can also bind to a plurality of targetable constructs. Further, the binding of the clearing agent to the targetable construct stabilizes binding of targetable construct to primary targeting agent at binding sites and enhances clearance of targetable construct not bound to primary targeting agent at binding sites.

As described in greater detail below, constructs for use in this invention can be configured in many different ways. For example, for a particular binding pair (e.g., an antibody/hapten pair), typically the respective members of that binding pair can be located on the relevant construct as desired. Thus, where an antibody/hapten binding pair is utilized, the antibody will be on one construct, and the cognate hapten will be on a construct to which the first construct will bind, or the antibody and hapten may be reversed on the two constructs. Such alternative constructs will be apparent from the following description. A few exemplary configurations are shown schematically in FIGS. 1-5, and 7-9.

A number of references are cited herein that provide information applicable to the present invention. For example, cited references include description of primary targeting agents, targetable constructs, and clearing agents that are useful or can be adapted to be useful in this invention. As a particularly useful example, Goldenberg et al., U.S. application Ser. No. 10/150,654, entitled "Use of Bi-Specific Antibodies for Pre-Targeting Diagnosis and Therapy" includes (but is not limited to) applicable description of bispecific antibody constructs, targetable constructs, clearing agents, targets, therapeutic and diagnostic moieties, methods of conjugating, methods of testing, and methods of using, and is incorporated herein by reference in its entirety.

In particular, the invention concerns constructs useful in the present methods. Thus, the invention concerns a tri-specific targetable construct adapted for delivery of a therapeutic or diagnostic moiety. The construct includes at least one first binding moiety suitable for binding with a separate primary targeting agent; a second binding moiety suitable for binding with a clearing agent; and a third binding moiety suitable for binding with an internalization agent. The construct preferably also includes a diagnostic or therapeutic moiety. The therapeutic moiety is a radioactive isotope, a non-radioactive metal chelate, a drug, a prodrug, a toxin or an enzyme that activates a prodrug or other therapeutic moieties disclosed herein. The diagnostic moiety is a photoactive agent, a contrast agent, a light scattering metal colloid particle, a radioactive isotope or a radioimaging metal chelate or other diagnostic moieties disclosed herein. The construct preferably binds to a mammalian cell and more preferably this construct is administered to a mammal and which results in being located inside the mammal.

In preferred embodiments, at least one of the first, second, and third binding moieties is a hapten; any two of the binding moieties are haptens; all three of the binding moieties are haptens; the binding moieties are preferably orthogonal. Additional features of the construct are as described herein for targetable constructs.

In certain embodiments, the construct is bound to a mammalian cell; such cells can be in a mammal, e.g., a human.

As disclosed herein, the invention provides a clearing agent suitable for clearing a targetable construct from circulation in a mammal. The clearing agent includes a binding moiety, and in certain embodiments, at least two binding moieties, suitable for binding a targetable construct; and an internalization moiety. Various embodiments of the clearing agent and/or internalization moieties are as described herein. The internalization moiety can be bound by a recycling cell surface receptor or a non-receptor mediated internalization peptide as described above. Additionally, the clearing agent can be an antibody, fragment thereof, a $C_H2$ deleted antibody or a galactosylated antibody as described herein.

In another related aspect, the invention provides a molecular complex that includes a targetable construct comprising at least one primary targeting agent binding moiety and an internalizing agent binding moiety, bound with an internalizing agent. The targetable construct may further comprise a clearing agent binding moiety. The internalizing agent of the complex further may comprise a targetable construct binding moiety and internalization moiety. The targetable construct further may comprise a therapeutic or diagnostic moiety as described herein. Various embodiments of clearing agent, and/or internalization moiety are as described for other aspects herein.

Yet another related aspect concerns a molecular complex that includes a targetable construct that includes at least one, preferably 2, primary targeting agent binding moieties, a clearing agent binding moiety, and a therapeutic or diagnostic moiety as described herein, bound with a clearing agent. In preferred embodiments, the primary targeting agent binding moiety and the clearing agent binding moiety include orthogonal haptens; at least two targetable constructs crosslinked by a clearing agent; and the complex also includes a primary targeting agent.

Another molecular complex includes a polyvalent primary targeting agent that includes a target binding moiety and a plurality of targetable construct binding moieties, preferably two, bound with a polyvalent targetable construct comprising a plurality of primary targeting agent binding moieties; a clearing agent binding moiety, and a therapeutic or diagnostic moiety as described herein. The targetable construct binding moieties may be antibody binding domains. The primary targeting agent binding moieties are orthogonal to the clearing agent binding moiety.

A further molecular complex includes a primary targeting agent that includes a target binding moiety and at least one targetable construct binding moiety; bound with a targetable construct that includes at least one primary targeting agent binding moiety, a clearing agent binding moiety, and a therapeutic or diagnostic binding moiety; as described herein, and bound with an internalizing agent that includes a targetable construct binding moiety or a clearing agent binding moiety, and an internalizing moiety.

Yet another complex includes a primary targeting agent that includes a target binding moiety and a therapeutic or diagnostic moiety, as described herein, bound with an internalization agent comprising a primary targeting agent binding moiety and an internalizing moiety.

In certain embodiments of complexes, the complex is bound to a mammalian cell; the complex can be bound to such cell in a mammal; the complex is bound at a binding site.

In view of the constructs, kits, and methods for targeting therapeutic or diagnostic agents to targeted cells, the invention also provides methods for treating and/or diagnosing a disease or condition in a subject (typically a patient), preferably a human subject. The method involves administering to a subject at least one therapeutic or diagnostic moiety in a targeted delivery method as described herein. Such diseases and conditions treatable by this method are disclosed herein below.

In certain embodiments, the therapeutic or diagnostic moiety is targeted in a manner that promotes internalization, e.g., with crosslinking to a rapidly internalizing receptor or with an internalizing peptide. Typically the therapeutic or diagnostic moiety is internalized as part of a target-bound complex. In particular embodiments, the therapeutic or diagnostic moiety includes an active species as listed herein. Also in certain embodiments, the therapeutic or diagnostic moiety is administered as part of a combination therapy.

In particular embodiments, targeting is to a marker, organism, or tissue as indicated herein. Likewise, in particular embodiments, the method is used to treat or diagnose (which can include imaging) a disease or condition as indicated herein.

In yet another aspect, the invention provides an advantageous method for preparing DTPA conjugated peptides by synthesis on a solid phase medium, e.g., on a resin. The synthesis is exemplified by the description of the preparation of IMP 272 in the Examples herein.

Additional aspects concern kits, that incorporate constructs as described above. One such kit is a kit for administration of a therapeutic or diagnostic agent. The kit includes a primary targeting agent that includes a target binding moiety and at least one targetable construct binding moiety; a targetable construct that includes at least one primary targeting agent binding moiety, a therapeutic or diagnostic moiety, as described herein, and a clearing agent binding moiety; and a clearing agent, that includes a targetable construct binding moiety. The primary targeting agent, targetable construct, and clearing agent can be configured as described above.

Another such kit includes a primary targeting agent that includes a target binding moiety and at least one internalization agent binding moiety; and an internalization agent that includes an internalization moiety that enhances internalization of a complex that contains the internalization moiety, and a primary targeting agent binding moiety.

Preferably a kit is approved by a regulatory agency for in vivo use in a mammal, e.g., a human.

As recognized by those of skill in the art, a number of different specific binding pairs can be utilized in addition to antibody/hapten or other antibody/epitope binding pairs. These include for example, metal chelation pairs, ligand/receptor binding pairs (natural, analog, or synthetic ligands), biotin/avidin or streptavidin, and carbohydrate/lectin.

Likewise, a number of internalization mechanisms can be utilized in place of the folate receptor with folate or methotrexate. For example, hormone or hormone analog/hormone receptor pairs such as steroid hormones; specific peptide/peptide receptor; and non-receptor mediated peptide internalization.

III. Bispecific Primary Targeting Species

In the present targeting methods, a primary targeting agent is used to bind to a selected target, typically a cellular target. In many cases, the target will be cells of a tissue, or cells having particular characteristics. In most cases, it is desirable for the primary targeting agent to be a bi-specific agent. Thus, the primary targeting agent typically is a bi-specific agent, including both a target binding moiety and at least one targetable construct binding moiety, where the targetable construct will typically bear a moiety that is intended to direct to the target, e.g., a therapeutic or diagnostic moiety.

Bispecific primary targeting agents, particularly antibody-based agents, have been described for a number of applications. Such descriptions include, for example: application Ser. No. 09/337,756, entitled "Use of bi-specific antibodies for pre-targeting diagnosis and therapy," filed Jun. 22, 1999; application Ser. No. 09/382,186, entitled "Use of bi-specific antibodies for pre-targeting diagnosis and therapy," filed Aug. 23, 1999; application Ser. No. 09/823,746, entitled "Production and use of novel peptide-based agents for use with bi-specific antibodies," filed Apr. 3, 2001; U.S. provisional patent application Ser. No. 60/361,037, entitled "Bispecific antibody point mutations for enhancing rate of clearance," filed Mar. 1, 2002; and published PCT application WO 99/66951 by Hansen et al., entitled "Use of bi-specific antibodies for pre-targeting diagnosis and therapy," all of which are incorporated by reference in their entireties, including drawings. These documents describe bi-specific antibody constructs that can be used, or adapted for use, in primary targeting agents for the present invention, and preparation of such primary targeting agent constructs. In addition, targeting agents described in the other references cited in the Background can be used or adapted for use in the present invention, e.g. by ensuring that there are binding moieties such that the targeting agent is bi-specific. Preferably the targeting agent is also polyvalent for binding to either or both of a target and a targetable construct. An exemplary primary binding agent that utilizes antibody binding for the target binding moiety and biotin or avidin/streptavidin for the targetable construct binding moiety is described in Goldenberg, U.S. Pat. No. 5,525,338, entitled "Detection and Therapy of Lesions with Biotin/Avidin Conjugates." Description of biotin and avidin/streptavidin conjugation to antibodies and other species is well-known in the art. See, for example, references cited in the Background; Griffiths et al., U.S. Pat. No. 5,846,741; Griffiths et al, U.S. Pat. No. 5,965,115, and Griffiths et al., U.S. Pat. No. 6,120,768, which are incorporated herein by reference in their entireties.

For the present primary targeting agents, the target binding moiety is selected to bind to the desired target, and thus can be any moiety capable of the necessary specific binding. Such moieties can, for example, include receptor ligands or analogs of such ligands, or antibodies or antibody fragments that recognize and bind with the target. Highly preferably the target binding moiety or moieties are high affinity, thereby maintaining stable binding to target even when a complex is formed with targetable construct and clearing agent. Highly preferably there are a plurality of target binding moieties, which may target the same or different target sites. Preferably there are a plurality of target binding moieties that can be bound concurrently to target epitopes. In many cases, the primary targeting agent will include at least 2 target binding moieties that recognize the same target epitope. The presence of multiple target binding moieties provides more stable binding and/or binding to alternate targets.

Likewise, the targetable construct binding moiety is selected to specifically bind with a moiety (primary targeting agent binding moiety) of the targetable construct. Generally the targetable construct binding moiety is one member of a binding pair, such as an antibody/hapten binding pair. Those skilled in the art are familiar with other binding pairs that can be used.

In one configuration, the target binding moiety of the primary targeting agent is an antibody, such as an IgG that specifically binds to a target site (e.g., a targeted tissue or cell type). The targetable construct binding moiety can be an antibody or hapten moiety or moieties, for example, at least one and preferably two such moieties (or more), for example, antibody binding arms or scFv moieties. The binding moiety, e.g., scFv, is specific for a binding site, e.g., a hapten on a targetable construct. In this case, the targetable construct includes at least 1, and preferably two units (or more) of a recognizable hapten. Examples of recognizable haptens that can be used include, but are not limited to, histamine succinyl glycine (HSG), DTPA and fluorescein isothiocyanate. When two or more targetable construct binding moieties are present on the primary targeting agent, the agent is thus both bi-specific and bi-valent (or polyvalent, e.g., tri-valent, tetravalent, etc.).

As indicated above, the binding of primary targeting agent to target can also be enhanced by incorporating multiple binding moieties. In some cases, an intact IgG antibody will be used, thus providing 2 binding arms, or two or more binding moities will be linked. Additional binding moieties can, e.g., additional antibodies or fragments, may recognize the same or different epitopes. Such multiple binding moieties are linked with appropriate distance and flexibility to allow the multiple binding moieties to bind.

Thus, the use of bi-specific antibody construct that includes a moiety, e.g., an intact antibody or scFv component, which is reactive to a targetable construct allows a variety of therapeutic and diagnostic applications to be performed without raising new bsAb for each application.

An exemplary bi-specific primary targeting agent is designated hMN14-m679. HMN14 is humanized anti-CEA. The m679 portion is murine anti-HSG. This construct is described in detail in U.S. patent application Ser. No. 09/823,746 filed Apr. 3, 2001, and in Sharkey, McBride, Karacay, Chang, Griffiths, Hansen, and Goldenberg, A Universal Pre-Targeting System for Cancer Detection and Therapy Using Bispecific Antibody. *Cancer Research* 63:354-363 (2003). This agent can be used with a targetable construct containing HSG moieties, such that the HSG moieties bind with the m679 portion of the agent. The clearing agent binding moiety on the targetable construct could then be an orthogonal hapten, such as In-DTPA, and the clearing agent would include anti-In-DTPA binding moieties. An exemplary hMN14-h679 trivalent, bispecific fusion protein is described in U.S. Provisional Patent Application No. 60/464,532 filed on Apr. 22, 2003, and is herein incorporated by reference. An exemplary primary targeting agent of this type is shown schematically in FIGS. 1-5. A similar primary targeting agent is shown schematically in FIGS. 7-9.

Another construct that can be used is designated hMN14-734scFv (hMN14-m734 can also be used as well as other agents having hMN14 linked with an antibody fragment derived from the 734 antibody), the preparation and structure of which is described in published PCT application WO 99/66951. As above, the hMN14 is a humanized anti-CEA antibody, and 734scFv is anti-In-DTPA (indium complexed with DTPA). This agent can be used with a targetable construct containing In-DTPA moieties, The clearing agent binding moiety on the targetable construct could then be an orthogonal hapten, such as HSG, and the clearing agent would then include anti-HSG binding moieties.

IV. Targetable Constructs

As described above, the targetable construct carries the active species, or "load". In the general targeted delivery method described herein, the targetable construct binds to the primary targeting agent to localize the active species, and binds with the clearing agent to cross-link separate target-bound targetable construct, and to clear unbound construct.

Targetable constructs can be constructed in any configuration to provide binding to both primary targeting agent and clearing agent. Typically, a targetable construct will be based on a peptide scaffold, but other chemistry such as carbohydrate can also be used. The construct also provides binding to primary targeting agent and to clearing agent, the targetable construct also includes at least 2 orthogonal binding moieties. In general, those binding moieties are members of specific binding pairs, such as either antibodies or haptens. Preferably the construct includes at least two orthogonal haptens, one of which binds with a primary targeting agent, and the other binds with a clearing agent. Such haptens include, but are not limited to a chelator or metal-chelate complex. By way of non-limiting example, the chelator may be a hard base chelator for a hard acid cation, and at least one of the chelators is a soft base chelator for a soft acid cation; or a hard base chelator that comprises carboxylate and amine groups. Non-limiting examples of hard base chelators include DTPA (diethylenetriaminepentaacetic acid), NOTA (1,4,7-triaza-cyclononane-N,N',N"-triacetic acid), DOTA (1,4,7,10-tetraazacyclotetradecane-N,N',N'''N'''-tetraacetic acid), and TETA (tetraazacyclotetradecane-N,N',N'',N'''-tetraacetic acid).

Preferably the targetable construct includes at least two binding moieties that are selected to bind with a primary targeting agent, such as at least two haptens. Those multiple binding moieties may be the same or different. For simplicity of construction, it is preferable if they are the same.

The targetable construct also includes at least one binding moiety selected to bind with a clearing agent. In preferred embodiments, there is one such clearing agent binding moiety. In the present method it is desirable to cross-link separate targetable construct molecules in order to "lock" the targetable constructs at the target site. Therefore, the targetable construct should have fewer clearing agent binding moieties than the corresponding clearing agent has targetable construct binding moieties. For example, if the clearing agent includes 2 moieties that bind with the targetable construct, the targetable construct should have only 1 moiety that binds to the clearing agent, leaving the second binding moiety on the clearing agent available to bind to a separate targetable construct.

The targetable construct may be conjugated to a variety of agents useful for treating or identifying diseased tissue. Examples of conjugated agents include, but are not limited to, chelators, metal chelate complexes, radionuclides, drugs, toxins (e.g., ricin, abrin, Staphylococcal enterotoxin-A, pokeweed antiviral protein, gelonin, diphtherin toxin, *Pseudomonas* exotoxin, *Pseudomonas* endotoxin) and other effector molecules, such as cytokines, lymphokines, oligonucleotides, chemokines, immunomodulators, enzymes, radiosensitizers, asparaginase, RNase, Dnase, receptor targeting agents. Additionally, enzymes useful for activating a prodrug or increasing the target-specific toxicity of a drug can be conjugated to the targetable construct. A number of examples of specific moieties that can be attached are described herein.

1. Peptide/Hapten Constructs

As indicated above, the targetable construct can be constructed with various structures. However, for constructs designed to participate in antibody binding, the structure is preferably selected not only to allow sufficiently tight binding, but also for rapid in vivo clearance. In many embodiments, a peptide-based structure is used, typically in conjunction with haptens to provide for antibody binding. Exemplary targetable constructs that can be adapted to the present invention by incorporation of orthogonal binding moieties to bind a clearing agent are described in U.S. application Ser. No. 09/337,756 filed Jun. 22, 1999 and in U.S. application Ser. No. 09/823,746, filed Apr. 3, 2001, which are incorporated herein by reference in their entireties. Additional targetable constructs that can be adapted for use in this invention are described in the additional references cited in the Background concerning pre-targeting methods. In general, for the present invention a targetable construct should include at least one and preferably a plurality of primary targeting agent binding moieties, and at least one clearing agent binding moiety, where the primary targeting agent binding moieties and the clearing agent binding moieties are orthogonal. Of course, the moieties that provide the respective binding functions depend on the particular primary targeting agent and clearing agent selected for use in a particular system.

While a targetable construct will usually include at least two orthogonal haptens for binding with antibody, in some cases, it may be desirable to elicit an immune response directly against a portion of a targetable construct. In general, hydrophobic agents are best at eliciting strong immune responses, whereas hydrophilic agents are preferred for rapid in vivo clearance, thus, a balance between hydrophobic and hydrophilic should be established. This can be accomplished, in part, by using hydrophilic chelating agents to offset the inherent hydrophobicity of many organic moieties. Also, subunits of the targetable construct may be chosen which have opposite solution properties, for example, peptides, which contain amino acids, some of which are hydrophobic and some of which are hydrophilic. As an alternative to peptides, carbohydrates may be used, preferably carbohydrate chains of 2 to six sugar units. A polymeric carbohydrate such as dextran can also be used.

Peptides having as few as two amino-acid residues may be used, preferably two to ten residues, if also coupled to other moieties such as chelating agents. The linker is preferably a low molecular weight conjugate, preferably having a molecular weight of less than 50,000 daltons, and advantageously less than about 20,000 daltons, 10,000 daltons or 5,000 daltons, including the metal ions in the chelates. For instance, the known peptide DTPA-Tyr-Lys(DTPA)-OH (wherein DTPA is diethylenetriaminepentaacetic acid) has been used to generate antibodies against the indium-DTPA portion of the molecule. However, by use of the non-indium-containing molecule, and appropriate screening steps, new Abs against the tyrosyl-lysine dipeptide can be made.

More commonly, the peptide will have binding hapten moieties, such In-DTPA and HSG, wherein HSG is the histamine succinyl glycyl group of the formula:

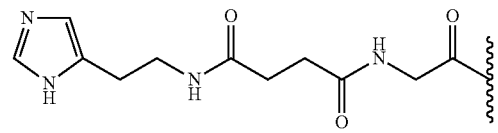

The peptides to be used as immunogens can be synthesized conveniently on an automated peptide synthesizer using a solid-phase support and standard techniques of repetitive orthogonal deprotection and coupling. Free amino groups in the peptide, that are to be used later for chelate conjugation, are advantageously blocked with standard protecting groups such as an acetyl group. Such protecting groups will be known to the skilled artisan. See, e.g., Greene and Wuts *Protective Groups in Organic Synthesis*, 1999 (John Wiley and Sons, N.Y.). When the peptides are prepared for use in the invention, they are advantageously cleaved from the resins to generate the corresponding C-terminal amides, in order to inhibit in vivo carboxypeptidase activity.

2. Chelate Moieties

The presence of chelate moieties on the linker moieties can provide several different functionalities. Hydrophilic chelate moieties help to ensure rapid in vivo clearance. In addition to hydrophilicity, chelators are chosen for their metal-binding properties. Such metal chelate combinations allow the incorporation of therapeutic or diagnostic metal isotopes, as well as, at least in some cases, providing a hapten moiety against which tight binding antibodies can be developed.

Exemplary useful metal-chelate combinations include 2-benzyl-DTPA and its monomethyl and cyclohexyl analogs, used with $^{47}$Sc, $^{52}$Fe, $^{55}$Co, $^{67}$Ga, $^{68}$Ga, $^{111}$In, $^{89}$Zr, $^{90}$Y, $^{161}$Tb, $^{177}$Lu, $^{212}$Bi, $^{213}$ and $^{225}$Ac for radio-imaging and RAIT. The same chelators, when complexed with non-radioactive metals, such as Mn, Fe and Gd can be used for MRI, when used along with the mutant bsAbs of the invention. Macrocyclic chelators such as NOTA (1,4,7-triaza-cyclononane-N,N',N''-triacetic acid), DOTA, and TETA (p-bromoacetamido-benzyl-tetraethylaminetetraacetic acid) are of use with a variety of metals and radiometals, most particularly with radionuclides of Ga, Y and Cu, respectively.

DTPA and DOTA-type chelators, where the ligand includes hard base chelating functions such as carboxylate or amine groups, are most effective for chelating hard acid cations, especially Group IIa and Group IIIa metal cations. Such metal-chelate complexes can be made very stable by tailoring the ring size to the metal of interest. Other ring-type chelators such as macrocyclic polyethers are of interest for stably binding nuclides such as $^{223}$Ra for RAIT. Porphyrin chelators may be used with numerous radiometals, and are also useful as certain cold metal complexes for bsAb-directed immuno-phototherapy. More than one type of chelator may be conjugated to a carrier to bind multiple metal ions, e.g., cold ions, diagnostic radionuclides and/or therapeutic radionuclides. Particularly useful therapeutic radionuclides include, but are not limited to $^{32}$P, $^{33}$P, $^{47}$Sc, $^{64}$Cu, $^{67}$Cu, $^{67}$Ga, $^{90}$Y, $^{111}$Ag, $^{111}$In, $^{125}$I, $^{131}$I, $^{142}$Pr, $^{153}$Sm, $^{161}$Tb, $^{166}$Dy, $^{166}$Ho, $^{177}$Lu, $^{186}$Re, $^{188}$Re, $^{189}$Re, $^{212}$Pb, $^{212}$Bi, $^{213}$Bi, $^{211}$At, $^{223}$Ra and $^{225}$Ac. Particularly useful diagnostic radionuclides include, but are not limited to, $^{18}$F, $^{45}$Ti, $^{52}$Fe, $^{62}$Cu, $^{64}$Cu, $^{67}$Cu, $^{67}$Ga, $^{68}$Ga, $^{86}$Y, $^{89}$Zr, $^{94m}$Tc, $^{94}$Tc, $^{99m}$Tc, $^{111}$In, $^{123}$I, $^{124}$I, $^{125}$I, $^{131}$I, $^{154-158}$Gd and $^{175}$Lu.

Chelators such as those disclosed in U.S. Pat. No. 5,753, 206, especially thiosemi-carbazonylglyoxylcysteine(Tscg-Cys) and thiosemicarbazinyl-acetylcysteine (Tsca-Cys) chelators are advantageously used to bind soft acid cations of Tc, Re, Bi and other transition metals, lanthanides and actinides that are tightly bound to soft base ligands, especially sulfur- or phosphorus-containing ligands. It can be useful to link more than one type of chelator to a peptide, e.g., a DTPA or similar chelator such as for In(III) cations, and a thiol-containing chelator, e.g., Tscg-Cys, for Tc cations. Because antibodies to a di-DTPA hapten are known (Barbet, U.S. Pat. No. 5,256,395) and are readily coupled to a targeting antibody to form a bsAb, it is possible to use a peptide hapten with cold diDTPA chelator and another chelator for binding a radioisotope, in a pretargeting protocol, for targeting the radioisotope. One example of such a peptide is Ac-Lys (DTPA)-Tyr-Lys(DTPA)-Lys(Tscg-Cys-)-NH$_2$. This peptide can be preloaded with In(III) and then labeled with 99-m-Tc cations, the In(III) ions being preferentially chelated by the DTPA and the Tc cations binding preferentially to the thiol-containing Tscg-Cys. Other hard acid chelators such as NOTA, DOTA, TETA and the like can be substituted for the DTPA groups, and Mabs specific to them can be produced using analogous techniques to those used to generate the anti-di-DTPA Mab.

Two different hard acid or soft acid chelators can be incorporated into the linker, e.g., with different chelate ring sizes, to bind preferentially to two different hard acid or soft acid cations, due to the differing sizes of the cations, the geometries of the chelate rings and the preferred complex ion structures of the cations. This will permit two different metals, one or both of which may be radioactive or useful for MRI enhancement, to be incorporated into a linker for eventual capture by a pretargeted primary targeting agent.

The chelators NOTA, DOTA and Tscg have been incorporated into exemplary chelator-peptide conjugate motifs as exemplified in the following constructs:

(a)

DOTA-Phe-Lys(HSG)-D-Tyr-Lys(HSG)-NH$_2$;

(b)

DOTA-Phe-Lys(HSG)-Tyr-Lys(HSG)-NH$_2$;

(c)

Ac-Lys(HSG)D-Tyr-Lys(HSG)-Lys(Tscg-Cys)-NH$_2$;

(d)

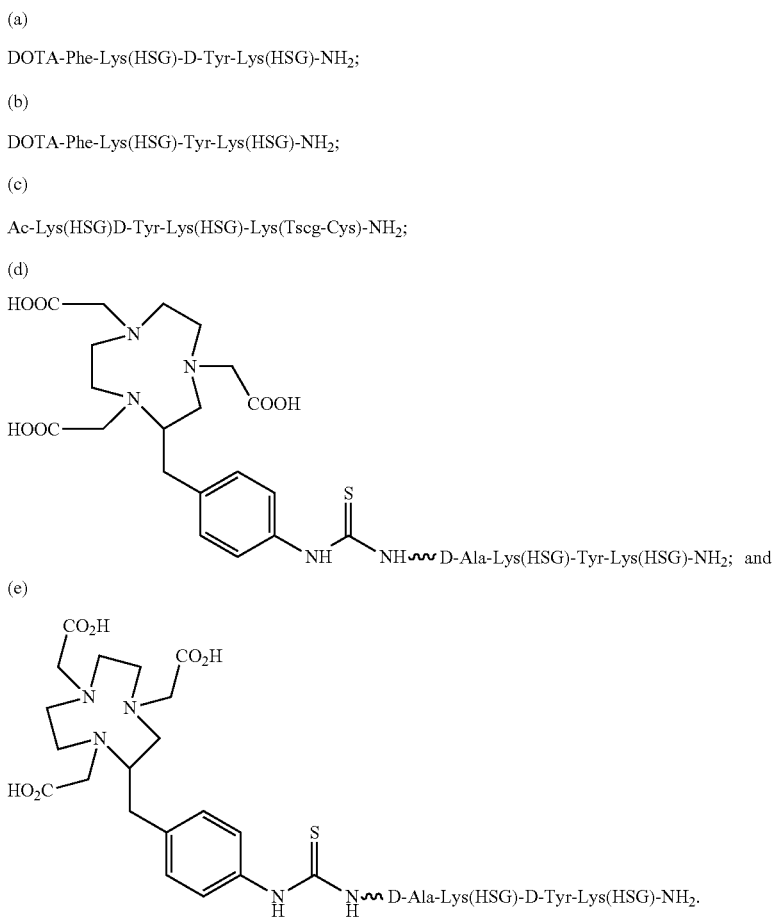

The chelator-peptide conjugates (d) and (e) above have been shown to bind $^{68}$Ga and thus can be useful in positron emission tomography (PET) applications.

Chelators are coupled to the linker moieties using standard chemistries. Briefly, the synthesis of the peptide Ac-Lys (HSG)D-Tyr-Lys(HSG)-Lys(Tscg-Cys-)-NH$_2$ was accomplished by first attaching Aloc-Lys(Fmoc)-OH to a Rink amide resin on the peptide synthesizer. The protecting group abbreviations "Aloc" and "Fmoc" used herein refer to the groups allyloxycarbonyl and fluorenylmethyloxy carbonyl. The Fmoc-Cys(Trt)-OH and TscG were then added to the side chain of the lysine using standard Fmoc automated synthesis protocols to form the following peptide: Aloc-Lys(Tscg-Cys (Trt)-rink resin. The Aloe group was then removed. The peptide synthesis was then continued on the synthesizer to make the following peptide: (Lys(Aloc)-D-Tyr(But)-Lys(Aloc)-Lys(Tscg-Cys(Trt)-)-rink resin. Following N-terminus acylation, and removal of the side chain Aloe protecting groups. The resulting peptide was then treated with activated N-trityl-HSG-OH until the resin gave a negative test for amines using the Kaiser test. See Karacay et al. *Bioconjugate Chem.* 11:842-854 (2000). The synthesis of Ac-Lys(HSG)D-Tyr-Lys(HSG)-Lys(Tscg-Cys-)-NH$_2$, as well as the syntheses of DOTA-Phe-Lys(HSG)-D-Tyr-Lys(HSG)-NH$_2$; and DOTA-Phe-Lys(HSG)-Tyr-Lys(HSG)-NH$_2$ are described in greater detail below.

3. General Methods for Preparation of Metal Chelates

Chelator-peptide conjugates may be stored for long periods as solids. They may be metered into unit doses for metal-binding reactions, and stored as unit doses either as solids, aqueous or semi-aqueous solutions, frozen solutions or lyophilized preparations. They may be labeled by well-known procedures. Typically, a hard acid cation is introduced as a solution of a convenient salt, and is taken up by the hard acid chelator and possibly by the soft acid chelator. However, later addition of soft acid cations leads to binding thereof by the soft acid chelator, displacing any hard acid cations that may be chelated therein. For example, even in the presence of an excess of cold $^{111}$InCl$_3$, labeling with 99m-Tc(V) glucoheptonate or with Tc cations generated in situ with stannous chloride and Na99m-TcO$_4$ proceeds quantitatively on the soft acid chelator. Other soft acid cations such as $^{186}$Re, $^{188}$Re, $^{213}$Bi and divalent or trivalent cations of Mn, Co, Ni, Pb, Cu, Cd, Au, Fe, Ag (monovalent), Zn and Hg, especially $^{64}$Cu and $^{67}$Cu, and the like, some of which are useful for radioimmunodiagnosis or radioimmunotherapy, can be loaded onto the peptide chelator combination by analogous methods. Re cations also can be generated in situ from perrhenate and stannous ions or a prereduced rhenium glucoheptonate or other transchelator can be used. Because reduction of perrhenate requires more stannous ion (typically above 200 µg/mL final concentration) than is needed for the reduction of Tc, extra care should be taken to ensure that the higher levels of stannous ion do not reduce sensitive disulfide bonds such as those present in disulfide-cyclized peptides. During radiolabeling with rhenium, similar procedures are used as are used with the Tc-99m. A preferred method for the preparation of ReO metal complexes of the Tscg-Cys- ligands is by reacting the peptide with ReOCl$_3$(P(Ph$_3$)$_2$ but it is also possible to use other reduced species such as ReO(ethylenediamine)$_2$.

Figure 7:
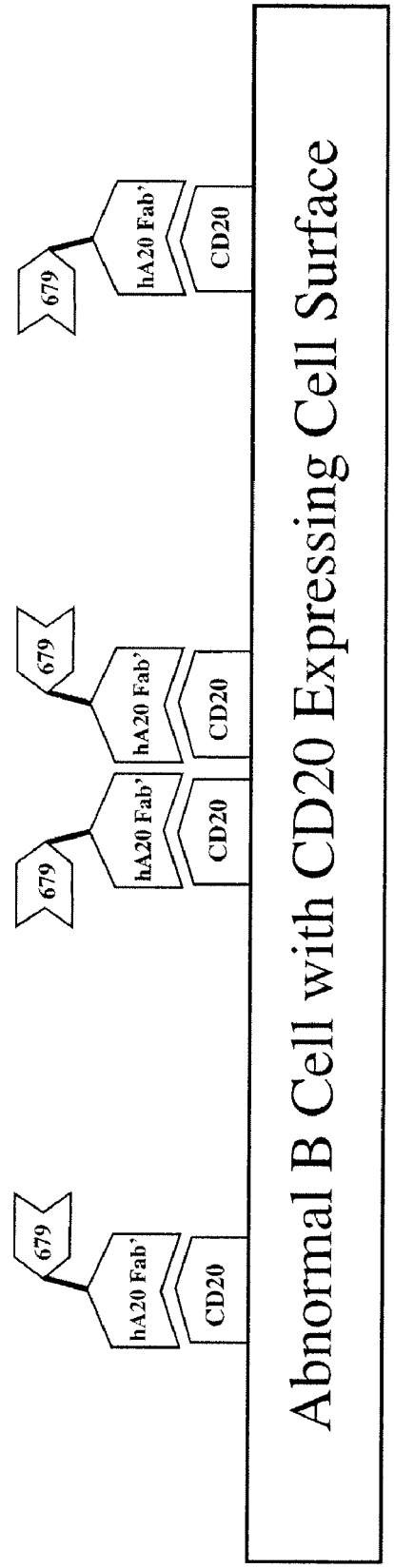
Figure 8:
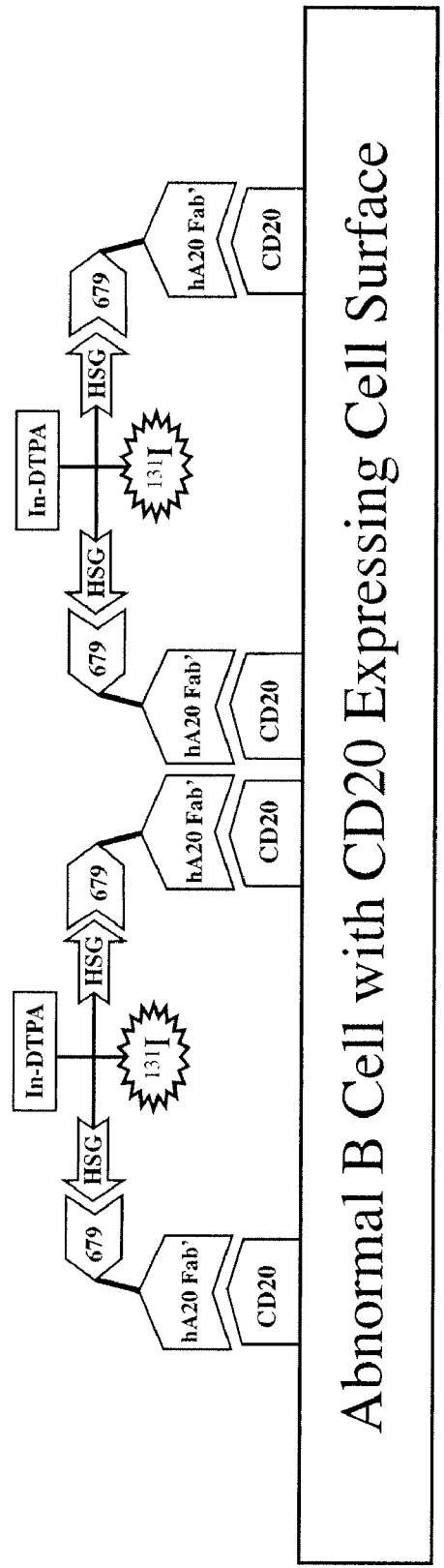

An exemplary targetable construct for the present invention was constructed that includes two HSG moieties and one DTPA moiety with a peptide scaffold or linker was constructed. (Illustrated shematically in FIGS. 1-4.) This construct is designated as IMP272, the preparation and structure of which are described in the Examples below. In this construct, the one DTPA moiety, used for binding to clearing agent, and the two HSG moieties are used for binding to primary targeting agent. For this purpose, the DTPA moiety chelates with indium, allowing binding to anti-In-DTPA antibody. Another exemplary targetable construct is shown in FIGS. 7-9. In this case, the targetable construct includes only one HSG moiety, so that it binds to only one primary targeting agent anti-HSG moiety.

V. Clearing Agents

In the present method, clearing agents provide a dual function by "locking" target-bound targetable construct at the target site by cross-linking separate targetable constructs, and also assisting in clearance of unbound targetable construct from circulation. In this context, the term "unbound" indicates that the construct is not bound at a target site, even though it may be bound to circulating primary targeting agent or other circulating components. In order to provide the locking function, the clearing agent highly preferably binds two or more separate targetable constructs, which may be of the same or different type. In most cases, the clearing agent is designed with only one type of targetable construct binding moiety, though multiple types of targetable construct binding moieties can alternatively be used.

In order to contribute to rapid clearance of unbound complex, preferably the clearing agent preferably includes one or more parts that are rapidly cleared. While native IgG antibodies are cleared relatively rapidly, the clearance rate can be enhanced by using certain modified antibodies or by using IgG1 which may fix complement, thus contributing to rapid clearance.

One type of modification that is known to enhance clearance rate is attachment of galactose (galactosylation). The level of galactosylation can be selected to provide desired clearance characteristics. See, e.g., Karacay et al., 1997, *Bioconjug Chem* 8(4):585-594. Galactose binds to the hepatic asialoglycoprotein receptor, whereby the associated agent or complex is rapidly recognized by liver hepatocytes. Use of galactosylated agents results in near-total hepatocytic recognition and sequestration within minutes post-injection, generally substantially in a single pass through the liver. As indicated, the degree of sugar residue modification of the agent determines the blood clearance rate. The number of sugar residues per molecule of agent to achieve a desired clearance rate may be determined empirically for each specific clearing agent by routine methods well-known in the art. It is convenient to express the degree of glycosylation in terms of the percentage of lysine residues modified by addition of sugars. For anti-idiotype antibody clearing agents, it has been found that modifying about 22% of the lysine residues does not provide significantly accelerated clearance of non-localized primary targeting conjugate, whereas modifying about 48% of the lysine residues greatly accelerate clearance, and modifying about 76% or more of the lysine residues results in virtually total clearance from circulation in a single pass through the liver. This is generally true for antibody fragments as well, although the percentages may vary to a degree. The level of glycosylation to achieve substantially complete clearance in one pass is readily determined.

Another type of modification that enhances clearance are certain types of mutations (generally substitutions or deletions) in the Fc-hinge portion of the IgG component, i.e., contains one or more amino acid mutations in the $C_H2$-$C_H3$ domain interface region. In other words, when the Fc-hinge portion of the IgG component of the mutant antibody is compared to the Fc-hinge portion of the IgG component of the parent antibody, the regions will differ by one or more amino acids. A mutation may encompass, for example, a "conservative" change, wherein a substituted amino has similar structural or chemical properties (e.g., replacement of leucine with isoleucine). A mutation also encompass, for example, a "non-conservative" change (e.g., replacement of a glycine with a tryptophan). Any amino acids in the $C_H2$-$C_H3$ domain interface region may be mutated. A preferred amino acid mutation is isoleucine 253 to alanine (I253A). A deletion of the $C_H2$ region can also provide such enhanced clearance.

Figure 3:
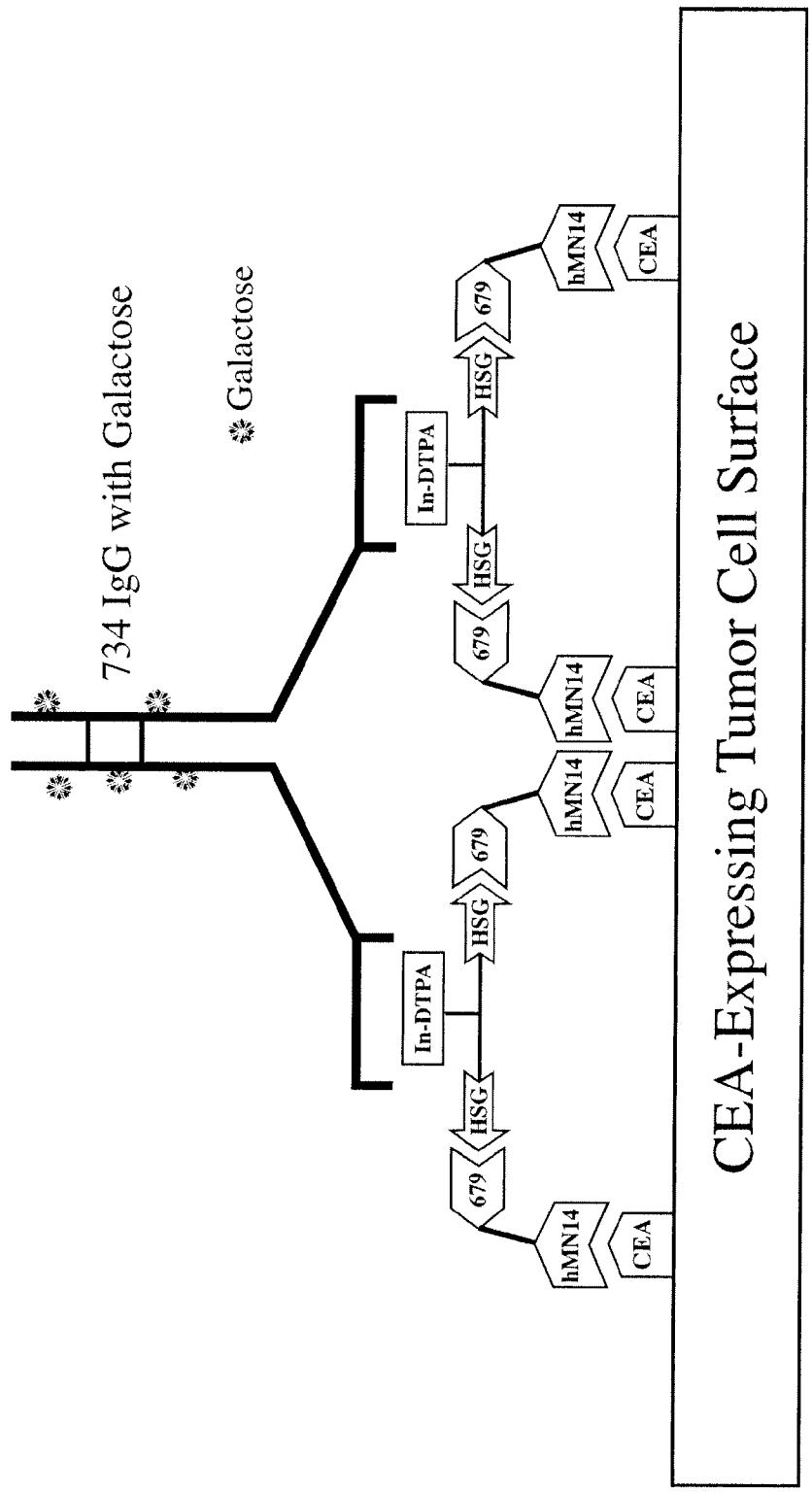
FIG. 3 is a schematic diagram showing pretargeting and locking as in FIG. 2, except that the clearing agent is modified with galactose moieties, such that the clearance rate of circulating clearing agent and any targetable constructs to which it is bound will be enhanced.
Figure 4:
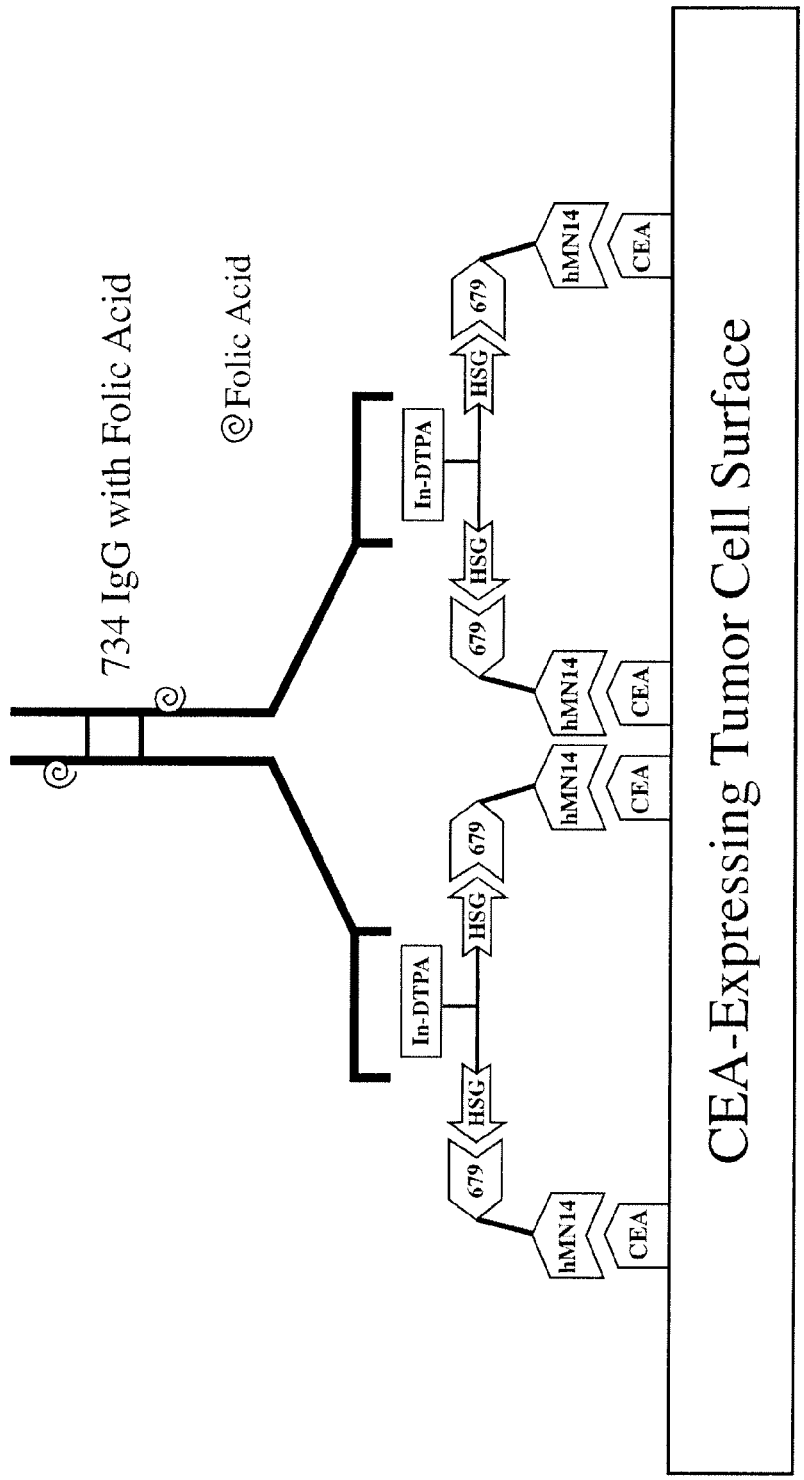
FIG. 4 is a schematic diagram showing pretargeting and locking as in FIG. 2, except that the clearing agent is modified with folic acid, such that the folic acid moieties will bind to folate receptors, enhancing internalization of the associated complex.
Figure 5:
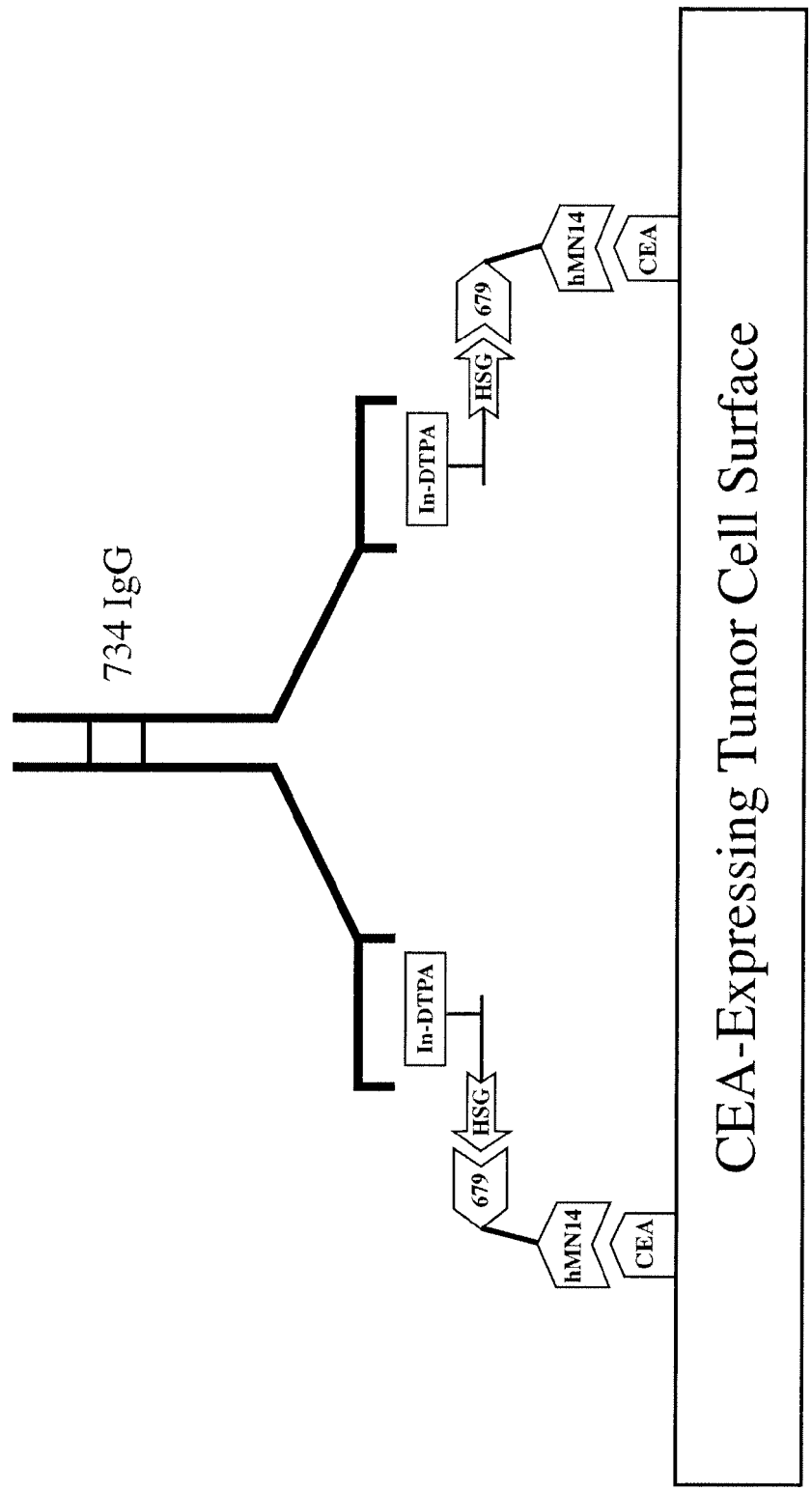
FIG. 5 is a schematic diagram showing an alternate configuration of targetable construct. In contrast to FIG. 2, the targetable construct has one HSG hapten, and so binds to one primary targeting agent. As in FIG. 2, the clearing agent crosslinks two target-bound targetable constructs, such that retention of targetable construct at the target site is enhanced. In this configuration, the complex crosslinks 2 target sites.

An exemplary clearing agent is shown schematically in FIGS. 2-5. The agent shown in FIG. 3 is modified with galactose to enhance clearance rate, and the agent shown in FIG. 4 is modified with folate to enhance internalization via folate receptors. Another exemplary clearing agent is shown schematically in FIG. 9. This clearing agent includes an antibody (hLL1) that binds to a rapidly internalizing B Cell tumor antigen (CD74). Binding of complexed clearing agent to CD74 then increases the internalization of the complex, and thus the internalization of the active species on the targetable construct.

VI. Concurrent Administration And Complexes Formed Before Administration

In many cases, it will be preferred to utilize pre-targeting, in which a primary targeting agent is administered and allowed to bind to target before administration of targetable construct. However, alternatively two or more of the system components can be adminstered essentially simultaneously or even mixed prior to administration. For example, a primary targeting agent and a targetable construct can be administered essentially at the same time, allowed to bind to target, followed by administration of clearing agent. Similarly, primary targeting agent, targetable construct, and clearing agent can be administered at the same time, and allowed to assemble on the target.

In addition, primary targeting agent and targetable construct can also be mixed prior to administration, forming complexes. Such complexes are administered similarly to administration of primary targeting agent, and allowed to bind to target. Clearing agent can then be used in the normal manner, locking bound complex at the target site and clearing unbound complex from circulation. Likewise, clearing agent can also be added to the mixture, and all three components administered as complexes. Mixing of all three components is particularly applicable when the clearing agent is not a rapidly clearing entity, but is primarily used for its "locking" function.

VII. Lock And Chase Targeting Methods

As discussed briefly above, the constructs described for the present invention provide an advantageous targeting method. The various constructs can be used in a number of different modes. In methods for targeting, the primary targeting agent provides the initial or primary targeting species that localizes that agent and other components of an associated complex to a target site. Thus, typically a pre-targeting method is used, where the primary targeting agent is administered to the subject and allowed to disperse and bind to target. Once sufficient accretion of the primary targeting species on targets is achieved, a targetable construct is administered. The targetable construct includes at least one binding site that recognizes an available binding site of the primary targeting agent and a diagnostic or therapeutic agent. Exemplary targetable constructs are described herein. The doses and timing of the reagents can be readily worked out by a skilled artisan, and are dependent on the specific nature of the reagents employed. While in general a pretargeting method may be performed with or without the use of a clearing agent, in most applications of the present invention, a clearing agent is used that also functions as a "locking" agent to stabilize association of targetable construct in a complex with primary targeting agent at target sites, even when the concentration of circulating targetable construct is reduced.

In addition to targeting, the present constructs can be configured to also enhance internalization of a complex by a targeted cell. The internalization is accomplished by attaching one or more internalization moieties to a complex that is to be internalized. Use of such internalization agents is described below.

The following illustrate some of the various designs that can be implemented for use in the present methods, in these cases, using combinations of antibodies and haptens. As indicated above, other binding pairs can be used as alternatives to, or in addition to antibodies and/or haptens.

1. Primary targeting agent: bsAb (2 target binding Ab moieties & 2 targetable construct hapten binding Ab moieties);
Targetable construct: peptide backbone with 2 orthogonal haptens(2 copies of a hapten recognized by hapten-binding antibodies on the primary targeting agent & the other recognized by a hapten-binding antibody on a clearing agent) plus therapeutic or diagnostic moiety;
Clearing agent: bi-valent Ab recognizing single copy hapten on targetable construct.

2. Primary targeting agent: bsAb (1 target binding Ab moiety & 1 targetable construct hapten binding Ab moieties);
Targetable construct: peptide backbone with 2 orthogonal haptens(2 copies of a hapten recognized by hapten-binding antibody on the primary targeting agent & the other recognized by a hapten-binding antibody on a clearing agent) plus therapeutic or diagnostic moiety;
Clearing agent: bi-valent Ab recognizing single copy hapten on targetable construct.

3. Primary targeting agent: bi-specific agent containing both Ab & hapten (2 target binding Ab moieties & 2 copies of a hapten recognized by Ab on targetable construct;
Targetable construct: peptide backbone with bi-valent Ab recognizing hapten on primary targeting agent & hapten (1 copy) recognized by Ab on clearing agent & therapeutic or diagnostic moiety;
Clearing agent: bi-valent Ab recognizing hapten on targetable construct.

4. Primary targeting agent: bi-specific agent containing both Ab (with 2 target binding moieties) and 2 copies of a hapten recognized by Ab on targetable construct;
Targetable construct: peptide backbone with bi-valent Ab recognizing hapten on primary targeting agent & 2 copies of a hapten recognized by Ab on clearing agent & therapeutic or diagnostic moeity;
Clearing agent: 4 Ab moieties recognizing hapten on targetable construct.

5. Primary targeting agent: bsAb (2 target binding Ab moieties & 2 targetable construct hapten binding Ab moieties);
Targetable construct: peptide backbone with 2 orthogonal haptens(2 copies of a hapten recognized by hapten-binding antibodies on the primary targeting agent & the other recognized by a hapten-binding antibody on a clearing agent) plus therapeutic or diagnostic moiety;
Clearing agent: bi-valent Ab recognizing single copy hapten on targetable construct & internalization moiety.

6. Primary targeting agent: bsAb (2 target binding Ab moieties & 2 targetable construct hapten binding Ab moieties);
Targetable construct: peptide backbone with 2 orthogonal haptens(2 copies of a hapten recognized by hapten-binding antibodies on the primary targeting agent & the other recognized by a hapten-binding antibody on a clearing agent) plus therapeutic or diagnostic moiety;

Clearing agent: bi-valent Ab recognizing single copy hapten on targetable construct & internalization agent binding moiety (Ab);

Internalization agent: hapten recognized by hapten binding Ab moiety on clearing agent (orthogonal to both haptens on targetable construct.

7. Primary targeting agent: bsAb (1 target binding Ab moiety & 1 targetable construct hapten binding Ab moieties);

Targetable construct: peptide backbone with 2 orthogonal haptens(1 copy of a hapten recognized by hapten-binding antibody on the primary targeting agent & 1 copy of a hapten recognized by a hapten-binding antibody on a clearing agent) plus therapeutic or diagnostic moiety;

Clearing agent: bi-valent Ab recognizing single copy hapten on targetable construct.

Some exemplary configurations utilizing antibodies and haptens are shown schematically in the Figures. Binding of primary targeting agent, targetable construct, and clearing agent is illustrated in FIGS. 1-5.

Figure 6:
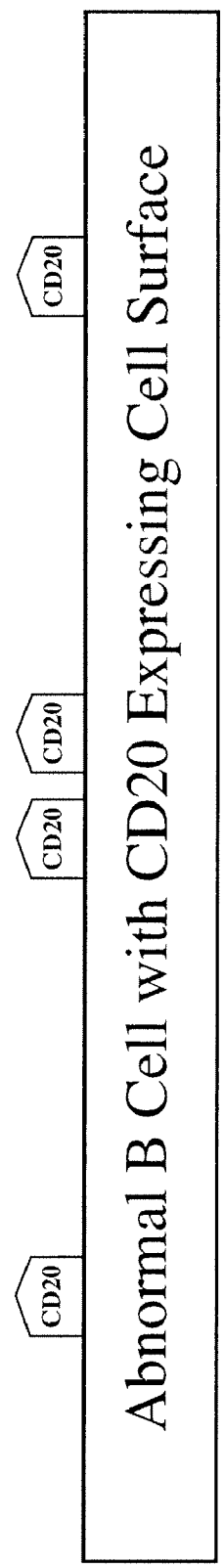
FIGS. 6-9 is a series of schematic diagrams illustrating the use a primary targeting agent to pretarget a cell surface marker, a targetable construct that binds to the primary targeting agent and crosslinks two such bound primary targeting agents, and a clearing agent that bind to targetable construct, crosslinking two bound targetable constructs, thereby forming a target-bound complex involving binding to 4 cell surface markers.

In addition, a sequential schematic illustration showing the series of bindings for an exemplary configuration is shown in the series of FIGS. 6-9. FIG. 6 illustrates a B Cell with multiple CD20 antigens displayed on the surface. The CD20 serves as the target antigen for the primary targeting agent as shown in FIG. 7. FIG. 7 indicates that the primary targeting agent is injected and illustrates the binding of primary targeting agent to the CD20 antigens as shown in FIG. 6. As shown, the primary targeting agent has an anti-CD20 Ab moiety (hA20Fab') linked with an anti-HSG Ab moiety for binding to targetable construct. After the primary targeting agent binds to the target sites, targetable construct is injected as shown in FIG. 8. As shown, the targetable construct binds to the localized primary targeting agents through the HSG haptens. Each targetable construct includes two HSG moieties and so can crosslink two localized primary targeting agents, an active species ($^{131}$I) and one DTPA moiety for binding to clearing agent. Binding of the targetable construct is followed by injection of clearing agent as shown in FIG. 9. The clearing agent includes is a bi-valent clearing agent with two anti-In-DTPA Ab moieties, and so can bind to and crosslink two targetable constructs. As the targetable constructs are themselves bound to two primary targeting agents, the result is the formation of a crosslinked complex bound to four target antigens, thereby "locking" the targetable construct at the target. In addition, the clearing agent in FIG. 9 includes an Ab moiety (hLL1) that binds to a different cell surface antigen, CD74, which is a rapidly internalizing surface antigen. Binding to CD74 can thus enhance internalization of the associated complex, include the active species (in this case, $^{131}$I).

The above combinations are only exemplary, other configurations can also be constructed, e.g., using other binding pairs replacing some or all of the Ab/hapten pairs in the exemplary combinations above.

VI. Applications Of Targeting Methods

The high resolution targeting provided by the invention can be utilized in many different types of applications for both therapy and diagnosis (including visualization). In such applications, the present constructs and methods can be used to deliver a moiety to a target site, thereby providing treatment and/or diagnosis or imaging, e.g., of a normal tissue or cell distribution. Several different types of applications are described below and in patents and patent applications that are incorporated by reference.

Without limitation the present compositions and methods can be used for therapy and/or diagnosis or imaging for cardiovascular lesions (infarcts, clots, emboli, atherosclerotic plaques), other pathological lesions (e.g., amyloid in amyloidosis and in Alzheimer's disease), cancers (e.g., leukemias, lymphomas, sarcomas, melanomas, carcinomas, gliomas, skin cancers), infectious diseases (e.g., bacterial, rickettsial, fungal, parasitical, and viral pathogens), inflammation (e.g., autoimmune diseases, such as rheumatoid arthritis, systemic erythematosis, multiple sclerosis), displaced or ectopic normal tissues and cells (e.g., endometrium, thymus, spleen, parathyroid), normal tissue ablation (e.g., bone marrow, spleen).

1. Detection and Imaging

Thus, for example, tumors can be detected in body cavities by means of directly or indirectly viewing various structures to which light of the appropriate wavelength is delivered and then collected. Lesions at any body site can be viewed so long as nonionizing radiation can be delivered and recaptured from these structures. For example, PET which is a high resolution, non-invasive, imaging technique can be used with the present agents for the visualization of human disease. In PET, 511 keV gamma photons produced during positron annihilation decay are detected.

The invention generally can utilize diagnostic agents that emit 25-600 keV gamma particles and/or positrons. Examples of such agents include, but are not limited to $^{18}$F, $^{45}$Ti, $^{52}$Fe, $^{62}$Cu, $^{64}$Cu, $^{67}$Cu, $^{67}$Ga, $^{68}$Ga, $^{86}$Y, $^{89}$Zr, $^{94m}$Tc, $^{94}$Tc, $^{99m}$Tc, $^{111}$In, $^{123}$I, $^{124}$I, $^{125}$I, $^{131}$I, $^{154-158}$Gd and $^{175}$Lu. Such signal generating agents are attached to one of the present components, typically a targetable construct, allowing targeting and subsequent imaging or detection.

Detection with intraoperative/endoscopic probes can also be performed, e.g., using a radiolabeled targetable construct (e.g., a peptide-based construct labeled with I-125). Such methods are described, for example, in U.S. Pat. Nos. 5,716, 595 and 6,096,289, and U.S. Patent Application Publication 2002/0146369, the entire contents of which are incorporated by reference.

Therapeutically and diagnostically useful immunoconjugates can be obtained by conjugating photoactive agents or dyes to a targetable construct. Fluorescent and other chromogens, or dyes, such as porphyrins sensitive to visible light, have been used to detect and to treat lesions by directing the suitable light to the lesion. In therapy, this has been termed photoradiation, phototherapy, or photodynamic therapy (PDT) (Jori et al. (eds.), *Photodynamic Therapy of Tumors and Other Diseases* (Libreria Progetto 1985); van den Bergh, *Chem. Britain* 22:430 (1986)). Moreover, monoclonal antibodies have been coupled with photoactivated dyes for achieving phototherapy. Mew et al., *J. Immunol.* 130:1473 (1983); idem., *Cancer Res.* 45:4380 (1985); Oseroff et al., *Proc. Natl. Acad. Sci. USA* 83:8744 (1986); idem., *Photochem. Photobiol.* 46:83 (1987); Hasan et al., *Prog. Clin. Biol. Res.* 288:471 (1989); Tatsuta et al., *Lasers Surg. Med.* 9:422 (1989); Pelegrin et al., *Cancer* 67:2529 (1991).

Photodynamic therapy (PDT) methods are also discussed in U.S. Pat. Nos. 6,096,289; 4,331,647; 4,818,709; 4,348, 376; 4,361,544; 4,444,744; 5,851,527, all of which are incorporated by reference in their entireties. In these methods, a photosensitizer, e.g., a hematoporphyrin derivative such as dihematoporphyrin ether, is administered to a subject. Antitumor activity is initiated by the use of light, e.g., 630 nm. Alternate photosensitizers can be utilized, including those useful at longer wavelengths, where skin is less photosensitized by the sun. Examples of such photosensitizers include, but are not limited to, benzoporphyrin monoacid ring A (BPD-MA), tin etiopurpurin (SnET2), sulfonated aluminum phthalocyanine (AlSPc) and lutetium texaphyrin (Lutex).

Additionally, in PDT, a diagnostic agent (e.g., a targetable construct as described herein) can be injected, for example, systemically, and laser-induced fluorescence can be used with endoscopes to detect sites of cancer which have accreted the light-activated agent. For example, this has been applied to fluorescence bronchoscopic disclosure of early lung tumors. Doiron et al. *Chest* 76:32 (1979). In another example, the present constructs can be used in single photon emission. For example, a Tc-99m-labeled diagnostic agent can be administered to a subject following administration of the primary targeting agent, followed by administration of a clearing agent. The subject is then scanned with a gamma camera that produces single-photon emission computed tomographic images and defines the lesion or tumor site.

As indicated above, the present compositions and methods can be applied in many contexts for diagnosis or imaging in addition to detection of cancer cells. For example, use of antibody targeting for detection of atheroslcerotic imaging is described in Example 8 of Goldenberg, U.S. Pat. No. 5,525, 338. Imaging was performed by scanning with a gamma camera. Cancer imaging and cancer therapy using antibody targeting were also described in that patent.

An example of an antibody target that can be used for imaging (and therapy) is an Alzheimer's disease specific tau protein epitope. (Vechterova et al., 2003, *Neuroreport* 14(1): 87-91, "DC11: a novel monoclonal antibody revealing Alzheimer's disease-specific tau epitope".) The identified monoclonal antibody (mAb DC11) bound to neurofibrillary pathology in brain derived from AD patients on immunohistochemistry, and lacked reactivity with healthy brain tissue. In Western blot, mAb DC11 recognized neither native healthy tau nor its full length recombinant counterpart. Thus, mAb DC11 (or another antibody with similar specificity) provides a useful target binding moiety with the specificity for conformation of pathological tau present in AD brains.

2. Therapeutic Applications

The present constructs, agents, and methods are highly advantageous for therapeutic applications. Generally, targets and diseases or conditions for which the present constructs are used for therapy can also be used for diagnosing (e.g., imaging) by appropriate selection of a diagnostic moieties instead of or in addition to the therapeutic moieties.

a. Enzymes and Prodrugs

In one type of application, a targetable construct can be conjugated to an enzyme capable of activating a prodrug at the target site, improving the efficacy of a normal therapeutic by controlling the body's detoxification pathways, or carrying out an enzymatic reaction that effects a therapeutic response. For example, after a suitable enzyme is pretargeted to the target site, a cytotoxic drug is injected, which is known to act at the target site. The drug may be one which is detoxified by the mammal's ordinary detoxification processes. For example, the drug may be converted into the potentially less toxic glucuronide in the liver. The detoxified intermediate can then be reconverted to its more toxic form by the pretargeted enzyme at the target site. Alternatively, an administered prodrug can be converted to an active drug by the pretargeted enzyme. The pretargeted enzyme improves the efficacy of the treatment by recycling the detoxified drug. This approach can be adopted for use with any enzyme-drug pair.

Certain cytotoxic drugs that are useful for anticancer therapy are relatively insoluble in serum. Some are also quite toxic in an unconjugated form, and their toxicity is considerably reduced by conversion to prodrugs. Conversion of a poorly soluble drug to a more soluble conjugate, e.g., a glucuronide, an ester of a hydrophilic acid or an amide of a hydrophilic amine, will improve its solubility in the aqueous phase of serum and its ability to pass through venous, arterial or capillary cell walls and to reach the interstitial fluid bathing the tumor. Cleavage of the prodrug deposits the less soluble drug at the target site. Many examples of such prodrug-to-drug conversions are described in Hansen U.S. Pat. No. 5,851, 527, which is incorporated herein by reference in its entirety.

Conversion of certain toxic substances such as aromatic or alicyclic alcohols, thiols, phenols and amines to glucuronides in the liver is the body's method of detoxifying them and making them more easily excreted in the urine. One type of antitumor drug that can be converted to such a substrate is epirubicin, a 4-epimer of doxorubicin (Adriamycin), which is an anthracycline glycoside and has been shown to be a substrate for human beta-D-glucuronidase See, e.g., Arcamone *Cancer Res.* 45:5995 (1985). Other analogues with fewer polar groups are expected to be more lipophilic and show greater promise for such an approach. Other drugs or toxins with aromatic or alicyclic alcohol, thiol or amine groups are candidates for such conjugate formation. These drugs, or other prodrug forms thereof, are suitable candidates for the site-specific enhancement methods of the present invention.

As another example, the prodrug CPT-11 (irinotecan) is converted in vivo by carboxylesterase to the active metabolite SN-38. One application of the invention, therefore, is to use a bsAb targeted against a tumor and a hapten (e.g. di-DTPA) followed by injection of a di-DTPA-carboxylesterase conjugate. Once a suitable tumor-to-background localization ratio has been achieved, the CPT-11 is given and the tumor-localized carboxylesterase serves to convert CPT-11 to SN-38 at the tumor. Due to its poor solubility, the active SN-38 will remain in the vicinity of the tumor and, consequently, will exert an effect on adjacent tumor cells that are negative for the antigen being targeted. This is a further advantage of the method. Modified forms of carboxylesterases have been described and are within the scope of the invention. See, e.g., Potter et al., *Cancer Res.* 58:2646-2651 (1998) and Potter et al., *Cancer Res.* 58:3627-3632 (1998).

As a further example, etoposide is a widely used cancer drug that is detoxified to a major extent by formation of its glucuronide and is within the scope of the invention. See, e.g., Hande et al. *Cancer Res.* 48:1829-1834 (1988). Glucuronide conjugates can be prepared from cytotoxic drugs and can be injected as therapeutics for tumors pre-targeted with mAb-glucuronidase conjugates. See, e.g., Wang et al. *Cancer Res.* 52:4484-4491 (1992). Accordingly, such conjugates also can be used with the targeting methods described here. Similarly, designed prodrugs based on derivatives of daunomycin and doxorubicin have been described for use with carboxylesterases and glucuronidases. See, e.g., Bakina et al. *J. Med. Chem.* 40:4013-4018 (1997). Other examples of prodrug/enzyme pairs that can be used within the present invention include, but are not limited to, glucuronide prodrugs of hydroxy derivatives of phenol mustards and beta-glucuronidase; phenol mustards or CPT-11 and carboxypeptidase; methotrexate-substituted alpha-amino acids and carboxypeptidase A; penicillin or cephalosporin conjugates of drugs such as 6-mercaptopurine and doxorubicin and beta-lactamase; etoposide phosphate and alkaline phosphatase.

b. Boron Neutron Capture Therapy (BNCT)

The invention can also be applied in the context of Boron Neutron Capture Therapy (BNCT) protocols. BNCT is a binary system designed to deliver ionizing radiation to tumor cells by neutron irradiation of tumor-localized $^{10}B$ atoms. BNCT is based on the nuclear reaction which occurs when a stable isotope, isotopically enriched $^{10}B$ (present in 19.8% natural abundance), is irradiated with thermal neutrons to produce an alpha particle and a $^{7}Li$ nucleus. These particles have a path length of about one cell diameter, resulting in high linear energy transfer. Just a few of the short-range 1.7 MeV alpha particles produced in this nuclear reaction are sufficient to target the cell nucleus and destroy it. Success with BNCT of cancer requires methods for localizing a high concentration of $^{10}B$ at tumor sites, while leaving non-target organs essentially boron-free. Compositions and methods for treating tumors in subjects using pre-targeting bsAb for BNCT are described in patent application Ser. No. 09/205,243 (incorporated herein by reference in its entirety) and can easily be modified for the purposes of the present invention.

c. Intraoperative, Intravascular, and Endoscopic Tumor and Lesion Detection, Biopsy and Therapy As indicated above for detection and imaging, in additional applications the present invention can be used in intraoperative, intravascular, and endoscopic tumor and lesion detection, biopsy and therapy as described in U.S. Pat. Nos. 5,716, 595 and 6,096,289, and U.S. Patent Application Publication 2002/0146369, all of which are incorporated herein by reference in their entireties.

d. Applications to Treatment of Diseases and Other Conditions

As indicated above, the present constructs and methods are applicable to a variety of diseases and conditions for which relevant tissues can be targeted. Some of the diseases and conditions that can be treated using this invention are briefly described below.

1. Cancer Treatment

As indicated above by the description of examples of techniques and agents useful for treating cancer, the present invention is quite useful for treating cancer. In general, the present invention can target an anticancer agent or component of an anticancer treatment to cancer cells. The targeting is preferably performed using a cell-surface cancer marker. In many cases, the marker is a protein or peptide that is present in much higher (e.g., several-fold or greater higher) on cancer cells that on normal cells. Such markers are often specific for a particular type of cancer, or a set of related cancers. A number of exemplary markers are provided herein, but those skilled in the art will recognize that other markers are known and that yet others will be identified. Such additional markers can also be used as targets in the present invention.

2. Autoimmune Disorders

As another exemplary application, the present compositions can be used in connection with autoimmune disorders. For example, targeting agents can be used that target B-cell antigens, such as CD22, CD20, CD19, CD74, or HLA-DR antigens. Examples of the use of targeting for treatment of autoimmune disorders is described in Goldenberg and Hansen, International application PCT/US00/015780, International Publication WO 00/74718 A1, entitled "Immunotherapy of Autoimmune Disorders Using Antibodies Which Target B-Cells." As describe therein, such treatments can include the use of antibodies that bind more than one B-cell antigen and the combination of the B-cell targeting with other treatments in multi-modal treatments methods. Examples of autoimmune diseases that can be treated include, without limitation, class III autoimmune diseases such as immune-mediated thromcytopenias (such as acute idiopathic thrombocytopenic purpura and chronic thrombocytopenic purpura), dermatomyositis, Sydenham" chorea, myasthenia gravis, systemic lupus erythematosus, lupus nephritis, rheumatic fever, polyglandular syndromes, bullous pemphigoid, diabetes mellitus, Henoch-Schonleim purpura, post-streptococcal nephritis, erythema nodosum, Takayasu's arteritis, Addison's disease, rheumatoid arthritis, multiple sclerosis, sarcoidosis, ulcerative lcolitis, erythema multiforme, IgA nephropathy, polyarteritis nodosa, ankylosing spondylitis, Goodpasture's syndrome, thromboangitis ubiterans, Sjogren's syndrome, primary biliary cirrhosis, Hashimoto's throiditis, throtoxicosis, scleroderma, chronic active hepatisis, polymyositis/dermatomyositis, polychrondritis, pamphigus vulgaris, Wegener's granulomatosis, mebranous nephropathy, amyotrophic lateral sclerosis, tabes dorsalis, giant cell arteritis/polymyalgia, pernicious anemia, rapidly progressive glomerulonephritis, and fibrosing alveolitis.

3. Infectious Diseases

Infectious entities such as pathogenic or opportunistic bacteria, fungi, rickettsia, protozoa, and viruses provide targets that can be used. Such targets can be on the cells of the infectious entity, or can be on the surface of infected host cells (e.g., in cases where infection of the cell leaves a characteristic marker on the cell surface). A number of particular infectious entities are listed herein as providing targets; which will not be repeated here.

4. Normal Cell Targeting

In many cases, the present methods are applied to target pathological targets, e.g., cancer cells, infected cells, infective entities, cells with a biochemical imbalance or defect in a biochemical function. However, in come cases it is beneficial to target normal cells, e.g., for 5. Combination Therapies In addition to methods in which a single therapeutic moiety is delivered using the present invention, the components and methods can be configured to simultaneously deliver at least one additional therapeutic moiety and/or with separate therapeutic methods. For example, the application of multiple agent therapy using targeted immunotherapy of cancer is described in Griffiths et al., U.S. Pat. No. 6,077,499, entitled "Targeted Combination Immunotherapy of Cancer", which is incorporated herein by reference in its entirety. Such a 2-agent (or multiple agent, e.g., 2, 3, 4-agent) method can be performed in the present invention, for example, by utilizing targetable construct that are constructed on the same binding moieties, but with different therapeutic moieties, or by utilizing a targetable construct that includes different therapeutic moieties. Such different therapeutic moieties can, for example, include two different drugs, two different toxins, two different radionuclides, a radionuclide and a drug, a radionuclide and a toxin, a drug and a toxin. Alternatively, separate targetable constructs can be utilized that bind to separate binding moieties, typically on a primary targeting agent or agents. Such combination therapy is also described in Griffiths, et al., International application PCT/US01/41048, International Publication WO 01/97855 A2, entitled "Targeted Combination Immunotherapy of Cancer and Infectious Diseases", which incorporated herein by reference in its entirety.

e. In Vitro Applications

The present constructs and methods can be employed not only for therapeutic or imaging purposes, but also as aids in performing research in vitro. For example, the bispecific primary targeting agents can be used in vitro to ascertain if a targetable construct can form a stable complex with one or more bsAbs or other bi-specific primary targeting agents. Such an assay aids the skilled artisan in identifying targetable constructs that form such stable complexes. This, in turn, allows the skilled artisan to identify targetable constructs that are likely to be superior as therapeutic and/or imaging agents.

Such an assay is advantageously performed by combining the targetable construct in question with at least two molar equivalents of a mutant bsAb. Following incubation, the mixture is analyzed by size-exclusion HPLC to determine whether or not the construct has bound to the bsAb. Alternatively, the assay is performed using standard combinatorial methods wherein solutions of various bsAbs are deposited in a standard 96 well plate. To each well, is added solutions of targetable construct(s). Following incubation and analysis, one can readily determine which construct(s) bind(s) best to which bsAb(s).

In such assays, the order of addition of the bi-specific agent to the targetable construct is not crucial; that is, the bi-specific agent may be added to the construct and vice versa. Likewise, neither the mutant bsAb nor the construct needs to be in solution; that is, they may be added either in solution or neat, whichever is most convenient. Lastly, the method of analysis for binding is not crucial as long as binding is established. Thus, one may analyze for binding using standard analytical methods including, but not limited to, FABMS, high-field NMR or other appropriate method in conjunction with, or in place of, size-exclusion HPLC. Those skilled in the art are familiar with many suitable detection methods.

VII. Target Antigens And Epitopes

A target epitope is comprised within, displayed by and/or released from targeted tissues of a subject, samples or cell cultures thereof. A sample may be a bodily tissue or fluid tissue and may be within a subject, or biopsied or removed from a subject, or a whole or any portion of a bodily organ. Additionally, the tissue may be "sample" in that the tissue is recently removed from a subject without any preservation steps between the excision and the methods of the current invention. The tissue may also have been preserved by such standard tissue preparation techniques including, but not limited to, freezing, quick freezing, paraffin embedding and tissue fixation, prior to application of the methods of the current invention.

By "displayed" it is meant that a portion of the membrane protein is present on the surface of a cell, tissue and/or organ, and is thus in contact with the external environment of the cell, tissue or organ. A target epitope may be associated with a disease including but not limited to cancers, other proliferative disorders, and pathogenic infections, and other diseases and conditions.

A. Antigens and Epitopes Associated with Hyperproliferative Diseases

The bispecific primary targeting agents (e.g., antibodies) used in the present invention can be designed to be specific to a variety of cell surface or intracellular antigens associated with hyperproliferative diseases. Normal tissue homeostasis is achieved by an intricate balance between the rate of cell proliferation and cell death. Disruption of this balance either by increasing the rate of cell proliferation or decreasing the rate of cell death can result in the abnormal growth of cells and is thought to be a major event in the development of cancer and other hyperproliferative diseases. Thus, a "hyperproliferative disease" is one in which cells have an abnormally high rate of cell division and/or an abnormally low rate of necrosis and/or apoptosis. Non-limiting examples include tumorigenesis; tumor progression; cancers, such as leukemia, solid tumors and metastases; psoriasis; benign hyperproliferative diseases, such as benign prostatic hypertrophy, benign hyperplasia of the skin, and hemangiomas; chronic inflammatory proliferative diseases, such as psoriasis and rheumatoid arthritis; proliferative ocular disorders, such as diabetic retinopathy and macular degeneration; and proliferative cardiovascular diseases, such as restenosis and atherosclerosis. Restenosis, characterized by the regrowth of smooth muscle cells into the lumen of blood vessels following angioplasty or other arterial damage, is a frequent and recurring problem in the long term success of angioplasty, and also occurs after arterial reconstructions, atherectomy, stent implantation, and laser angioplasty.

These antigens may be substances produced by, e.g., the tumor or may be substances which accumulate at a tumor site, on tumor cell surfaces or within tumor cells, whether in the cytoplasm, the nucleus or in various organelles or subcellular structures, including cell-surface or intracellular receptors. Among such tumor-associated markers are those disclosed, but not intended to be limiting, by Herberman, Immunodiagnosis of Cancer, in Fleisher ed., *The Clinical Biochemistry of Cancer*, page 347 (American Association of Clinical Chemists, 1979) and in U.S. Pat. Nos. 4,150,149; 4,361,544; and 4,444,744.

Tumor-associated markers have been categorized by Herberman, supra, in a number of categories including oncofetal antigens, placental antigens, oncogenic or tumor virus associated antigens, tissue associated antigens, organ associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG) or the gamma region of carcino embryonic antigen (CEA), which stimulate the production of antibodies having a greatly reduced cross-reactivity to non-tumor substances as described in U.S. Pat. Nos. 4,361,644 and 4,444,744 (incorporated by reference herein in their entireties).

Examples, which are non-limiting, of suitable tumor-associated markers or receptors, include the B-cell complex structures (e.g., CD19, CD20, CD21, CD22, CD23, CD74, CD80), other receptors expressed on hematopoietic and certain solid tumors (e.g., CD74, HLA-DR), and tumor-associated markers expressed on diverse cancers (e.g., carcinoembryonic antigen, CSAp, MUC-1, MUC-2, MUC-3, MUC-4, Tag-72, EGP-1, EGP-2, the antigen specific for A33 antibody, PSA, PSMA, EGFR, HER2/neu, PAM-4, AFP, HCG and its sub-units, melanoma-associated antigens (e.g., S100), glioma-associated antigens, ovarian cancer-associated antigens, etc.), as well as target molecules expressed by the vasculature of the tumors (tumor angiogenesis markers, usually produced by the vascular endothelium), such as VEGF and tenascin (the latter in brain tumors, for example), and also to oncogene-associated markers, such as p53. In addition to the exemplary antibodies to such antigens disclosed herein, antibodies to these antigens are known in the art (see, for example, Kim S., Song S., Kim Y., Park S. Expression and Characterization of a Recombinant Fab Fragment Derived from an Anti-Human alpha-Fetoprotein Monoclonal Antibody. *Mol. Cells.* 11:158-163, 2001; and Haisma H J, Sernee M F, Hooijberg E, Brakenhoff R H, Meulen-Muileman I, Pinedo H M; Boven E. Construction and characterization of a fusion protein of single-chain anti-CD40 antibody and human β-glucuronidase for antibody-directed enzyme prodrug therapy. *Blood* 92:184-190, 1998.

Another marker of interest is transmembrane activator and CAML-interactor (TACI). See Yu et al. Nat. Immunol. 1:252-256 (2000). Briefly, TACI is a marker for B-cell malignancies (e.g., lymphoma). Further it is known that TACI and B cell maturation antigen (BCMA) are bound by the tumor necrosis factor homolog a proliferation-inducing ligand (APRIL). APRIL stimulates in vivo proliferation of primary B and T cells and increases spleen weight due to accumulation of B cells in vivo. APRIL also competes with TALL-I (also called BLyS or BAFF) for receptor binding. Soluble BCMA and TACT specifically prevent binding of APRIL and block APRIL-stimulated proliferation of primary B cells. BCMA-Fc also inhibits production of antibodies against keyhole limpet hemocyanin and Pneumovax in mice, indicating that APRIL and/or TALL-I signaling via BCMA and/or TACI are required for generation of humoral immunity. Thus, APRIL-TALL-I and BCMA-TACI form a two ligand-two receptor pathway involved in stimulation of B and T cell function.

Tumor-specific antigens (TSAs), tumor-associated differentiation antigens (TADAs) and other antigens associated with cancers and other hyperproliferative diseases also include, but are not limited to, C1 IAC, a human cancer associated protein (Osther, U.S. Pat. No. 4,132,769); the CA125 antigen, an antigen associated with cystadenocarcinoma of the ovary, (Hanisch et al., Carbohydr. Res. 178:29-47, 1988; O'Brien, U.S. Pat. No. 4,921,790); CEA (carcinembryonic antigen), an antigen present on many adenocarcinomas (Horig et al., Strategies for cancer therapy using carcinembryonic antigen vaccines, Expert Reviews in Molecular Medicine, http://www-ermm.cbcu.cam.ac.uk: 1, 2000); CORA (carcinoma or orosomucoid-related antigen) described by Toth et al. (U.S. Pat. No. 4,914,021); DF3 antigen from human breast carcinoma (Kufe, in U.S. Pat. Nos. 4,963,484 and 5,053,489); DU-PAN-2, a pancreatic carcinoma antigen (Lan et al., Cancer Res. 45:305-310, 1985); HCA, a human carcinoma antigen (Codington et al., U.S. Pat. No. 5,693,763); Her2, a breast cancer antigen (Fendly et al., The Extracellular Domain of HER2/neu Is a Potential Immunogen for Active Specific Immunotherapy of Breast Cancer, Journal of Biological Response Modifiers 9:449-455, 1990); MSA, a breast carcinoma glycoprotein (Tjandra et al., Br. J. Surg. 75:811-817, 1988); MFGM, a breast carcinoma antigen (Ishida et al., Tumor Biol. 10:12-22, 1989); PSA, prostrate specific antigen (Nadji et al., Prostatic-specific-antigen, Cancer 48:1229-1232, 1981); STEAP (six transmembrane epithelial antigens of the prostate) proteins (Afar et al., U.S. Pat. No. 6,329,503); TAG-72, a breast carcinoma glycoprotein (Kjeldsen et al., Cancer Res. 48:2214-2220, 1988); YH206, a lung carcinoma antigen (Hinoda et al., Cancer J. 42:653-658, 1988); the p97 antigen of human melanoma (Estin et al., Recombinant Vaccinia Virus Vaccine Against the Human Melanoma Antigen p97 for Use in Immunotherapy, Proc. Natl. Acad. Sci. USA, 85:1052-1056, 1988); and the melanoma specific antigen described by Pfreundschuh in U.S. Pat. No. 6,025,191).

B. Pathogen-Related Antigens

While the present invention is particularly advantageous for targeting to epitopes related to cancer and other proliferative diseases, it is not limited to such epitopes. For example, the present invention can be used to target epitopes related to the presence of pathogens, such as viruses, bacteria, and fungi. A wide variety of monoclonal antibodies have been developed against infectious agents, e.g., as summarized in Polin, 1984, *Eur. J. Clin. Microbiol.* 4(5):387-398. Particular antibodies against infectious agents are described in U.S. Pat. Nos. 3,927,193; 4,331,647; 4,348,376; 4,361,544; 4,818,709, and 4,624,846. Such antibodies or other suitable antibodies directed against those targets can be used in this invention. Further, some exemplary pathogens are pointed out below.

1. Viruses

Examples of viruses that can be targeted include, but are not limited to, hepatitis type A, hepatitis type B, hepatitis type C, influenza, varicella, adenovirus, herpes simplex type I (HSV-I), herpes simplex type II (HSV-II), rinderpest, rhinovirous, echovirus, rabies virus, Ebola virus, rotavirus, respiratory syncytial virus, papilloma virus, papova virus, cytomegalovirus (CMV), echinovirus, arbovirus, huntavirus, coxsackie virus, mumps virus, measles virus, rubella virus, polio virus, human immunodeficiency virus type I (HIV-I) and human immunodeficiency virus type II (HIV-II), Sendai virus, feline leukemia virus, Reovirus, poliovirus, human serum parvo-like virus, simian virus 40 (SV40), respiratory syncytial virus (RSV), mouse mammary tumor virus (MMTV), Varicella-Zoster virus, Dengue virus, rubella virus, measles virus, adenovirus, human T-cell leukemia viruses, Epstein-Barr virus, murine leukemia virus, vesicular stomatitis virus (VSV), smallpox (Variola virus), Sindbis virus, lymphocytic choriomeningitis virus, Rinderpest virus, wart virus and blue tongue virus.

2. Intracellular Pathogens

Similarly, non-limiting examples of intracellular obligate pathogens include *Chlamydia* sp., *Rickettsia* sp., intracellular protozoa, including but not limited to, species of *Leishmania, Kokzidioa*, and *Trypanosoma*, including without limitation intracellular spirochetes, including but not limited to, *Borrelia burgdorfei*, the causative agent of Lyme disease; and species of *Plasmodia*, sporozoan obligate intracellular parasites of liver and red blood cells, including but not limited to *P. falciparum*, the causative agent of malaria, *Trypanosoma brucei*, a hemoflagellate causing sleeping sickness, and *Trypanosoma cruzi*, the cause of Chagas disease. For reviews of the immunology of such pathogens, see Blackman M J. Proteases involved in erythrocyte invasion by the malaria parasite: function and potential as chemotherapeutic targets. *Curr Drug Targets.* 2000 July; 1(1):59-83; Kosma P. Chlamydial lipopolysaccharide. *Biochim Biophys Acta.* 1999 Oct. 8; 1455 (2-3):387-402; Casadevall A. Antibody-mediated protection against intracellular pathogens. *Trends Microbiol.* 1998 March; 6(3):102-7; Hoffman S L, Franke E D. Inducing protective immune responses against the sporozoite and liver stages of Plasmodium. *Immunol Lett.* 1994 July; 41(2-3):89-94; Keusch G T. Immune responses in parasitic diseases. Part A: general concepts. *Rev Infect Dis.* 1982 July-August; 4(4): 751-5; and Colli W, Alves M J M. Relevant glycoproteins on the surface of *Trypanosoma cruzi*.

3. Bacteria

Likewise, bacterial pathogens include, but are not limited to, *Streptococcus aureus, Streptococcus agalactiae, Legionella pneumophilia, Streptococcus pyogenes, Escherichia coli, Salmonella typhimurium, Neisseria gonorrhoeae, Neisseria meningitidis, Pneumococcus* sp., *Hemophilis influenzae* B, *Yersina pestis, Mycobacteria* sp. including by way of non-limiting example *Mycobacterium leprae* and *Mycobacterium tuberculosis, Treponema pallidum, Pseudomonas aeruginosa, Francisella tularensis, Brucella* sp. including *Brucella abortus, Bacillus anthracis* including Anthrax spores, *Clostridium botulinum* including Botulism toxin, and *Clostridium tetani* including Tetanus toxin). See U.S. Pat. No. 5,332,567.

4. Pathogenic Fungi

Fungal pathogens that can be targeted include, but are not limited to, *Candida* sp., *Aspergillus* sp., *Mucor* sp., *Rhizopus* sp., *Fusarium* sp., *Penicillium marneffei* and *Microsporum. Trichophyton mentagrophytes, Candida albicans, Histoplasma capsulatum, Blastomyces dermatitidis*, and *Coccidioides immitis*. Other such fungal pathogens can also be used.

C. Other Targets

The targets listed above are not intended to be limiting. It is recognized antigens or epitopes distinguishing other diseases, conditions, infectious agents, tissues and the like are known and more are being identified. An example is the Alzheimer's disease specific tau protein epitope indicated above. (Vechterova et al., 2003, *Neuroreport* 14(1):87-91, "DC11: a novel monoclonal antibody revealing Alzheimer's disease-specific tau epitope".)

VIII. Active Species

In the present invention, a variety of different species can be directed by targeting to a target site. In most cases, the species to be delivered to the target is a diagnostic or therapeutic species. These include, for example, visualization agents, contrast agents, radioactive therapeutic isotopes, drugs, and toxins, but are not limited to these. A number of examples are described herein in connection with conjugation or complexation to targetable construct. Such active species can also be conjugated with other delivery components for use in additional targeting methods. For example, the active species can be conjugated with a primary targeting agent (a species that directly binds to a target) for use in method that utilize a separate internalization agent that binds with the primary targeting agent.

IX. Internalization Moieties

The present targeting methods and constructs can also be used in conjunction with techniques for enhancing internalization of the targeted complex or portions thereof. In these methods, a targetable construct specifically associates with an internalization moiety. Such an internalization moiety can be incorporated as a moiety on a primary targeting agent or clearing agent, or can be presented as a separate internalization agent that specifically associates with the primary targeting agent, targetable construct, or clearing agent. Highly preferably, the internalization moiety is separated from the active species prior to targeting in order to reduce non-targeted internalization of the active species.

A variety of different species that enhance internalization are known and can be utilized. Examples include folic acid (folate) or methotrexate with internalization via folate receptor; steroid hormones and their respective receptors; receptor-recognized peptides, e.g., somatostatin, LHRH bombesin/CCKB, substance P, VIP. In addition, bispecific antibodies that cross-link the targetable construct to a rapidly internalizing membrane protein can also be used to enhance internalization. For example, the targetable construct can be directed to CD20 on lymphoma cells, and then cross-linked to CD74 using a bispecific antibody. A suitable anti-CD74 antibody to use to construct the cross-linking bispecific antibody is LL1, described in U.S. Pat. No. 6,458,933, incorporated herein by reference in its entirety. Alternatively, a bispecific antibody can be used to cross-link the targetable construct to CD22, or CD19, both known to be rapidly internalizing b-cell specific molecules present on b-cell lymphomas. A suitable anti-CD22 antibody for this purpose is LL2, described in U.S. Pat. No. 5,789,554, incorporated herein by reference in its entirety. As a second example, the targetable construct can be directed to CD66e (CEA) on carcinoma cells, and then cross-linked to EGP-1 using a bispecific antibody. A suitable anti-EGP-1 antibody to use to construct the cross-linking bispecific antibody is RS7, described in Govindan et al., U.S. Provisional Appl. No. 60/360,229, filed Mar. 1, 2002, entitled RS7 ANTIBODIES, which is incorporated by reference herein in its entirety. EGP-2 (Anticancer Res 1998 September-October; 18(5B): 3669-75) represents another rapidly internalizing tumor associated antigen present on CD66e positive carcinoma cells, which can be used as described above for EGP-1 to effect internalization.

Likewise, certain viral or virus-like peptides that are internalized by a non-receptor mediated mechanism can be used. Examples of cell-penetrating peptides include without limitation, pentratin, transportan, Tat, and MAP. See, for example, Hallbrink et al., 2001, Cargo delivery kinetics of cell-penetrating peptides, BBiochimica et Biophysica Acta 1515: 1001-1009; Gallouzi & Steitz, 2001, Delineation of mRNA export pathways by the use of cell-permeable peptides, Science 294:1895-1901, which are incorporated herein by reference in their entireties.

X. Methods For Internalizing Molecular Complexes

Internalization moieties (e.g., as described above) can be used to assist in internalization of targeted active species. Especially where the active species is a toxic agent, it is highly preferably to minimize the level of non-targeted internalization mediated by an internalization moiety. Thus, the internalization moiety should be separate from the active species in order to avoid such non-specific internalization. That is, the internalization moiety should be part of a separate species than the active species. For example, where an primary targeting agent, targetable construct, and clearing agent are used and the active species is part of the targetable construct, the internalization moiety can attached to the clearing agent or less desirably to the primary targeting agent, or can be presented as a separate species that is administered following binding of complex at target site and specifically binds with primary targeting agent, targetable construct, or clearing agent. By separating the active species from the internalization moiety physically and/or temporally, the non-specific internalization of active species is minimized.

In another example, such internalization agents can be used even without the present targeting, locking, and clearing methods. For example, the active species, such as a toxin or therapeutic radionuclide is conjugated or complexed on a primary targeting agent. That agent is administered and allowed to accrete at the target site. Then internalization agent is administered, where the internalization agent include a binding moiety that specifically binds to the primary targeting agent to form a complex and enhances internalization of the complex. In this way, the amount of circulating active species associated with internalization agent is minimized, thereby minimizing non-specific internalization of the active species.

In another example, as pointed out above, internalization can be accomplished without a specific internalization agent, by cross-linking a primary targeting agent to a rapidly internalizing cell surface receptor. This method is particularly applicable where the target is one that is present on normal cells, but is present at a much higher level on specific targeted cells, e.g., cancer cells. In these cases, there will be relatively little targeting agent bound to no, mal cells as compared to that bound to the targeted cells. Cross-linking to a rapidly internalizing surface molecule and resulting internalization will therefore occur much more frequently on the targeted cells than on normal cells. In this way, internalization of the active species in normal cells will occur at a much lower level than in the targeted cells.

XI. Kits

In order to facilitate carrying out the methods of the invention, it is advantageous to provides kits, e.g., kits containing components suitable for treating or diagnosing diseased tissue in a patient. Such a kit can contain at least one construct as described herein, e.g., a primary targeting agent, a targetable construct, a clearing agent, an internalization agent, and each combination of such components. If a targetable construct is included, highly preferably the construct includes a diagnostic or therapeutic moiety, or is configured to bind to such a moiety.

In addition, if the composition containing components for administration are not formulated for delivery via the alimentary canal, which includes but is not limited to sublingual delivery, a device capable of delivering the therapeutic agent through some other routes can also be included. One type of device, for applications such as parenteral delivery, is a syringe that is used to inject the composition into the body of an animal in need of the therapeutic agent. Inhalation devices may also be used.

It can also be advantageous to include separate containers, each of which comprises one or more reagents of the kit, or a container that has a plurality of compartments. In a preferred embodiment, the containers are vials that contain sterile, lyophilized formulations of a composition that are suitable for reconstitution. A kit can also contain one or more buffers suitable for reconsititution and/or dilution of other reagents, such as primary targeting agent, targetable construct, clearing agent, and/or internalization agent. Other containers that may be used include, but are not limited to, a pouch, tray, box, tube, or the like. Kit components may be packaged and maintained sterilely within the containers.

Another component that can be included is instructions to a person using a kit for its use. The instructions can be present on one or more of the kit components, the kit packaging and/or a kit package insert. Such instructions include, by way of non-limiting example, instructions for use of the kit and its reagents, for reconstituting lyophilized reagents or otherwise preparing reagents, and/or for monitoring subjects following administration.

In preferred embodiments, the kits is approved for use, e.g., for use with humans, by the applicable national or regional regulatory authority charged with regulating diagnostic and/or therpeutic agents, e.g., the U.S. Food and Drug Administration.

Examples of the Present Kits Include:

A kit for administration of a therapeutic or diagnostic agent, including a primary targeting agent comprising a target binding moiety and at least one targetable construct binding moiety; a targetable construct comprising at least one primary targeting agent binding moiety, a therapeutic or diagnostic moiety, and a clearing agent binding moiety; and a clearing agent, comprising a targetable construct binding moiety.

Another example is a kit that includes a primary targeting agent that has at least one target binding moiety and at least one internalization agent binding moiety; and an internalization agent that has an internalization moiety that enhances internalization of a complex that includes that internalization moiety, and a primary targeting agent binding moiety. The kit can also include a targetable construct and/or a clearing agent, in which case the primary targeting agent would also include at least one targetable construct binding moiety.

A large number of other kits of this invention are provided that include selections of primary targeting agent, targetable construct, clearing agent, and/or internalization agent as described herein. For example, particular kits include primary targeting agents directed to particular targets described herein, targetable constructs that include active species and/or haptens as described, bi-valent clearing agents as described, and/or internalization agents or moieties as described.

XII. Administration

The present constructs can be used in treating and/or imaging normal tissue and organs using a variety of administration methods. Without limitation, administration can be intravenous, intraarterial, intraperitoneal, intramuscular, subcutaneous, intropleual, intrathecal, by perfusion through a regional catheter, and by direct intralesional injection. Exemplary administration methods are described in U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210. Additional methods are described in U.S. application Ser. No. 09/337,756 filed Jun. 22, 1999 and in U.S. application Ser. No. 09/823,746, filed Apr. 3, 2001. All of these references are incorporated by reference in their entireties. In addition to the description provided in those documents, the following describes some useful information for preparing and using pharmaceutical compositions.

In general, for administration to a mammal, the present constructs will be formulated in pharmaceutical compositions. The term "pharmaceutical composition" refers to a composition comprising an entity to be delivered, wherein the carrier is a pharmaceutically acceptable carrier, while a "veterinary composition" is one wherein the carrier is a veterinarily acceptable carrier. The term "pharmaceutically acceptable carrier" or "veterinarily acceptable carrier" includes any medium or material that is not biologically or otherwise undesirable, i.e., the carrier may be administered to an organism along with a composition or compound of the invention without causing any undesirable biological effects or interacting in a deleterious manner with the complex or any of its components or the organism. Examples of pharmaceutically acceptable reagents are provided in The United States Pharmacopeia, The National Formulary, United States Pharmacopeial Convention, Inc., Rockville, Md. 1990, hereby incorporated in its entirety by reference herein into the present application, as is *Pharmaceutical Dosage Forms & Drug Delivery Systems,* 7th Edition, Ansel et al., editors, Lippincott Williams & Wilkins, 1999.

The molecule to be delivered (e.g., primary targeting agent, targetable construct, clearing agent, or complex) is included in the pharmaceutical composition in an amount sufficient to produce the desired effect upon the patient. The pharmaceutical compositions of the invention can further comprise other chemical components, such as diluents and excipients. A "diluent" is a chemical compound diluted in a solvent, preferably an aqueous solvent, that facilitates dissolution of the drug in the solvent, and it may also serve to stabilize the biologically active form of the drug or one or more of its components. Salts dissolved in buffered solutions are utilized as diluents in the art. For example, preferred diluents are buffered solutions containing one or more different salts. A preferred buffered solution is phosphate buffered saline (particularly in conjunction with compositions intended for pharmaceutical administration), as it mimics the salt conditions of human blood. Since buffer salts can control the pH of a solution at low concentrations, a buffered diluent rarely modifies the biological activity of a biologically active peptide.

An "excipient" is any more or less inert substance that can be added to a composition in order to confer a suitable property, for example, a suitable consistency or to form a drug. Suitable excipients and carriers include, in particular, fillers such as sugars, including lactose, sucrose, mannitol, or sorbitol cellulose preparations such as, for example, maize starch, wheat starch, rice starch, agar, pectin, xanthan gum, guar gum, locust bean gum, hyaluronic acid, casein potato starch, gelatin, gum tragacanth, polyacrylate, methyl cellulose, hydroxypropylmethyl-cellulose, sodium carboxymethylcellulose, and/or polyvinylpyrrolidone (PVP). If desired, disintegrating agents can also be included, such as cross-linked polyvinylpyrrolidone, agar, or alginic acid or a salt thereof such as sodium alginate. Other suitable excipients and carriers include hydrogels, gellable hydrocolloids, and chitosan. Chitosan microspheres and microcapsules can be used as carriers. See WO 98/52547 (which describes microsphere formulations for targeting compounds to the stomach, the formulations comprising an inner core (optionally including a gelled hydrocolloid) containing one or more active ingredients, a membrane comprised of a water insoluble polymer (e.g., ethylcellulose) to control the release rate of the active ingredient(s), and an outer layer comprised of a bioadhesive cationic polymer, for example, a cationic polysaccharide, a cationic protein, and/or a synthetic cationic polymer; U.S. Pat. No. 4,895,724. Typically, chitosan is cross-linked using a suitable agent, for example, glutaraldehyde, glyoxal, epichlorohydrin, and succinaldehyde. Compositions employing chitosan as a carrier can be formulated into a variety of dosage forms, including pills, tablets, microparticles, and microspheres, including those providing for controlled release of the active ingredient(s). Other suitable bioadhesive cationic polymers include acidic gelatin, polygalactosamine, polyamino acids such as polylysine, polyhistidine, polyornithine, polyquaternary compounds, prolamine, polyimine, diethylaminoethyldextran (DEAE), DEAE-imine, DEAE-methacrylate, DEAE-acrylamide, DEAE-dextran, DEAE-cellulose, poly-p-aminostyrene, polyoxethane, copolymethacrylates, polyamidoamines, cationic starches, polythiodiethylaminomethylethylene and polyvinylpyridine.

The targetable constructs, other agent, and complexes of the invention can be formulated in any suitable manner. The targetable constructs and complexes may be uniformly (homogeneously) or non-uniformly (heterogeneously) dispersed in the carrier. Suitable formulations include dry and liquid formulations. Dry formulations include freeze dried and lyophilized powders, which are particularly well suited for aerosol delivery to the sinuses or lung, or for long term storage followed by reconstitution in a suitable diluent prior to administration. Other preferred dry formulations include those wherein a pharmaceutical composition according to the invention is compressed into tablet or pill form suitable for oral administration or compounded into a sustained release formulation. When the pharmaceutical composition is intended for oral administration but the targetable construct or complex is to be delivered to epithelium in the intestines, it is preferred that the formulation be encapsulated with an enteric coating to protect the formulation and prevent premature release of the targetable constructs and complexes included therein. As those in the art will appreciate, the pharmaceutical compositions of the invention can be placed into any suitable dosage form. Pills and tablets represent some of such dosage forms. The pharmaceutical compositions can also be encapsulated into any suitable capsule or other coating material, for example, by compression, dipping, pan coating, spray drying, etc. Suitable capsules include those made from gelatin and starch. In turn, such capsules can be coated with one or more additional materials, for example, and enteric coating, if desired. Liquid formulations include aqueous formulations, gels, and emulsions.

Some preferred embodiments concern compositions that comprise a bioadhesive, preferably a mucoadhesive, coating. A "bioadhesive coating" is a coating that allows a drug to adhere to a biological surface or substance better than occurs absent the coating. A "mucoadhesive coating" is a preferred bioadhesive coating that allows a substance, for example, a composition according to the invention, to adhere better to mucosa occurs absent the coating. For example, micronized particles (e.g., particles having a mean diameter of about 5, 10, 25, 50, or 100 ◼m) can be coated with a mucoadhesive. The coated particles can then be assembled into a dosage form suitable for delivery to an organism. Preferably, and depending upon the location where the cell surface transport moiety to be targeted is expressed, the dosage form is then coated with another coating to protect the formulation until it reaches the desired location, where the mucoadhesive enables the formulation to be retained while the compositions or compounds of the invention interact with the target cell surface transport moiety.

The pharmaceutical compositions of the invention facilitate administration of monoclonal antibodies to an organism, preferably an animal, preferably a mammal, bird, fish, insect, or arachnid. Preferred mammals include bovine, canine, equine, feline, ovine, and porcine animals, and non-human primates. Humans are particularly preferred. Multiple techniques of administering or delivering a compound exist in the art including, but not limited to, oral, rectal (e.g., an enema or suppository) aerosol (e.g., for nasal or pulmonary delivery), parenteral, and topical administration. Preferably, sufficient quantities of the composition or compound of the invention are delivered to achieve the intended effect. The particular amount of composition or compound to be delivered will depend on many factors, including the effect to be achieved, the type of organism to which the composition is delivered, delivery route, dosage regimen, and the age, health, and sex of the organism. As such, the particular dosage of a composition or compound of the invention included in a given formulation is left to the ordinarily skilled artisan's discretion.

Those skilled in the art will appreciate that when the pharmaceutical compositions of the present invention are administered as agents to achieve a particular desired biological result, which may include a therapeutic or protective effect(s), it may be necessary to combine the composition or compound of the invention with a suitable pharmaceutical carrier. The choice of pharmaceutical carrier and the preparation of the composition or compound as a therapeutic or protective agent will depend on the intended use and mode of administration. Suitable formulations and methods of administration of therapeutic agents include, but are not limited to, those for oral, pulmonary, nasal, buccal, ocular, dermal, rectal, or vaginal delivery.

Depending on the mode of delivery employed, the constructs used in the present invention can be delivered in a variety of pharmaceutically acceptable forms. For example, the constructs can be delivered in the form of a solid, solution, emulsion, dispersion, micelle, liposome, and the like, incorporated into a pill, capsule, tablet, suppository, aerosol, droplet, injectable, or spray. Pills, tablets, suppositories, aerosols, powders, droplets, and sprays may have complex, multilayer structures and have a large range of sizes. Aerosols, powders, droplets, and sprays may range from small (1 micron) to large (200 micron) in size.

Pharmaceutical compositions of the present invention can be used in the form of a solid, a lyophilized powder, a solution, an emulsion, a dispersion, a micelle, a liposome, and the like, wherein the resulting composition contains one or more of the targetable constructs or complexes of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include, for example, glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Examples of a stabilizing dry agent includes triulose, preferably at concentrations of 0.1% or greater (See, e.g., U.S. Pat. No. 5,314,695).

Although individual needs may vary, determination of optimal ranges for effective amounts of pharmaceutical compositions is within the skill of the art. Human doses can be extrapolated from animal studies (Katocs et al., Chapter 27 In: *Remington's Pharmaceutical Sciences,* 18th Ed., Gennaro, ed., Mack Publishing Co., Easton, Pa., 1990). Generally, the dosage required to provide an effective amount of a pharmaceutical composition, which can be adjusted by one skilled in the art, will vary depending on the age, health, physical condition, weight, type and extent of the disease or disorder of the recipient, frequency of treatment, the nature of concurrent therapy (if any) and the nature and scope of the desired effect(s). See, for example, Nies et al., Chapter 3 In: Goodman & Gilman's *The Pharmacological Basis of Therapeutics*, 9th Ed., Hardman et al., eds., McGraw-Hill, New York, N.Y., 1996)

Dosing of therapeutic compositions is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The term "patient" is intended to encompass animals (e.g., cats, dogs and horses) as well as humans. Persons of ordinary skill can easily determine optimum dosages, dosing methodologies and repetition rates. Optimum dosages may vary depending on the relative potency of individual therapeutic agents, and can generally be estimated based on $EC_{50}$ found to be effective in in vitro and in vivo animal models.

The range of doses (the amount of targetable construct or complex administered) is broad, since in general the efficacy of a therapeutic effect for different mammals varies widely with doses typically being 20, 30 or even 40 times smaller (per unit body weight) in man than in the rat. In general, dosage is from 0.01 ug to 100 g per kg of body weight, preferably 0.01 ug to 10 g/kg of body weight, 0.01 ug to 1000 mg/kg of body weight, 0.01 ug to 100 mg/kg of body weight, 0.01 ug to 10 mg/kg of body weight, 0.01 ug to 1 mg/kg of body weight, 0.01 ug to 100 ug/kg of body weight, 0.01 ug to 10 ug/kg of body weight, 0.01 ug to 1 ug/kg of body weight, 0.01 ug to 10 ug/kg of body weight, 0.01 ug to 1 ug/kg of body weight, 0.01 ug to 0.1 ug/kg of body weight, and ranges based on the boundaries of the preceding ranges of concentrations. Thus, for example, the preceding description of dosages encompasses dosages within the range of 100 to 10 g per kg of body weight, 10 g to 1000 mg/kg of body weight, 1000 mg to 100 mg, etc.

Doses may be given once or more daily, weekly, monthly or yearly, or even once every 2 to 20 years. Persons of ordinary skill in the art can easily estimate repetition rates for dosing based on measured residence times and concentrations of the targetable construct or complex in bodily fluids or tissues. Following successful treatment, it may be desirable to have the patient undergo maintenance therapy to prevent the recurrence of the disease state, wherein the therapeutic agent is administered in maintenance doses, ranging from 0.01 ug to 100 g per kg of body weight, once or more daily, to once every 20 years.

The specific dose is calculated according to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data.

An individual patient's dosage can be adjusted as the progress of the disease is monitored. Blood levels of the targetable construct or complex in a patient can be measured to see if the dosage needs to be adjusted to reach or maintain an effective concentration. Pharmacogenomics may be used to determine which targetable constructs and/or complexes, and dosages thereof, are most likely to be effective for a given individual (Schmitz et al., *Clinica Chimica Acta* 308:43-53, 2001; Steimer et al., *Clinica Chimica Acta* 308:33-41, 2001).

XIII Methods For Raising Antibodies

Antibodies to desired epitopes are generated by well-known methods for Ab production. For example, injection of an immunogen, such as (peptide), KLH, wherein KLH is keyhole limpet hemocyanin, and n=1-30, in complete Freund's adjuvant, followed by two subsequent injections of the same immunogen suspended in incomplete Freund's adjuvant into immunocompetent animals, is followed three days after an i.v. boost of antigen, by spleen cell harvesting. Harvested spleen cells are then fused with Sp2/0-Ag14 myeloma cells and culture supernatants of the resulting clones analyzed for anti-peptide reactivity using a direct-binding ELISA. Fine specificity of generated Abs can be analyzed for by using peptide fragments of the original immunogen. These fragments can be prepared readily using an automated peptide synthesizer. For Ab production, enzyme-deficient hybridomas are isolated to enable selection of fused cell lines. This technique also can be used to raise antibodies to one or more of the chelates comprising the linker, e.g., In(III)-DTPA chelates. Monoclonal mouse antibodies to an In(III)-di-DTPA are known (Barbet '395 supra).

The antibodies used in the present invention for targeting are specific to any of a variety of cell surface or intracellular tumor-associated antigens as marker substances. These markers may be substances produced by the tumor or may be substances which accumulate at a tumor site, on tumor cell surfaces or within tumor cells, whether in the cytoplasm, the nucleus or in various organelles or sub-cellular structures. Among such tumor-associated markers are those disclosed by Herberman, "Immunodiagnosis of Cancer", in Fleisher ed., "The Clinical Biochemistry of Cancer", page 347 (American Association of Clinical Chemists, 1979) and in U.S. Pat. Nos. 4,150,149; 4,361,544; and 4,444,744.

Tumor-associated markers have been categorized by Herberman, supra, in a number of categories including oncofetal antigens, placental antigens, oncogenic or tumor virus associated antigens, tissue associated antigens, organ associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG) or the gamma region of carcinoembryonic antigen (CEA), which stimulate the production of antibodies having a greatly reduced cross-reactivity to non-tumor substances as disclosed in U.S. Pat. Nos. 4,361, 644 and 4,444,744.

Another marker of interest is transmembrane activator and CAML-interactor (TACI). See Yu et al. *Nat. Immunol.* 1:252-256 (2000). Briefly, TACI is a marker for B-cell malignancies (e.g., lymphoma). Further it is known that TACI and B cell maturation antigen (BCMA) are bound by the tumor necrosis factor homolog a proliferation-inducing ligand (APRIL). APRIL stimulates in vitro proliferation of primary B and T cells and increases spleen weight due to accumulation of B cells in vivo. APRIL also competes with TALL-I (also called BLyS or BAFF) for receptor binding. Soluble BCMA and TACT specifically prevent binding of APRIL and block APRIL-stimulated proliferation of primary B cells. BCMA- Fc also inhibits production of antibodies against keyhole limpet hemocyanin and Pneumovax in mice, indicating that APRIL and/or TALL-I signaling via BCMA and/or TACI are required for generation of humoral immunity. Thus, APRIL-TALL-I and BCMA-TACI form a two ligand-two receptor pathway involved in stimulation of B and T cell function.

After the initial raising of antibodies to the immunogen, the antibodies can be sequenced and subsequently prepared by recombinant techniques. Humanization and chimerization of murine antibodies and antibody fragments are well known to those skilled in the art. For example, humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by the publication of Orlandi et al., *Proc. Nat'l Acad. Sci. USA* 86: 3833 (1989), which is incorporated by reference in its entirety. Techniques for producing humanized Mabs are described, for example, by Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993), each of which is hereby incorporated by reference.

Alternatively, fully human antibodies can be obtained from transgenic non-human animals. See, e.g., Mendez et al., *Nature Genetics,* 15: 146-156 (1997); U.S. Pat. No. 5,633,425. For example, human antibodies can be recovered from transgenic mice possessing human immunoglobulin loci. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy- or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny which produce human antibodies in response to immunization.

Unrearranged human immunoglobulin genes also can be introduced into mouse embryonic stem cells via microcell-mediated chromosome transfer (MMCT). See, e.g., Tomizuka et al., *Nature Genetics,* 16: 133 (1997). In this methodology microcells containing human chromosomes are fused with mouse embryonic stem cells. Transferred chromosomes are stably retained, and adult chimeras exhibit proper tissue-specific expression.

As an alternative, an antibody or antibody fragment of the present invention may be derived from human antibody fragments isolated from a combinatorial immunoglobulin library. See, e.g., Barbas et al., *METHODS: A Companion to Methods in Enzymology* 2: 119 (1991), and Winter et al., *Ann. Rev. Immunol.* 12: 433 (1994), which are incorporated by reference. Many of the difficulties associated with generating monoclonal antibodies by B-cell immortalization can be overcome by engineering and expressing antibody fragments in *E. coli*, using phage display. To ensure the recovery of high affinity, monoclonal antibodies a combinatorial immunoglobulin library must contain a large repertoire size. A typical strategy utilizes mRNA obtained from lymphocytes or spleen cells of immunized mice to synthesize cDNA using reverse transcriptase. The heavy- and light-chain genes are amplified separately by PCR and ligated into phage cloning vectors. Two different libraries are produced, one containing the heavy-chain genes and one containing the light-chain genes. Phage DNA is isolated from each library, and the heavy- and light-chain sequences are ligated together and packaged to form a combinatorial library. Each phage contains a random pair of heavy- and light-chain cDNAs and upon infection of *E. coli* directs the expression of the antibody chains in infected cells. To identify an antibody that recognizes the antigen of interest, the phage library is plated, and the antibody molecules present in the plaques are transferred to filters. The filters are incubated with radioactively labeled antigen and then washed to remove excess unbound ligand. A radioactive spot on the autoradiogram identifies a plaque that contains an antibody that binds the antigen. Cloning and expression vectors that are useful for producing a human immunoglobulin phage library can be obtained, for example, from STRATAGENE Cloning Systems (La Jolla, Calif.).

A similar strategy can be employed to obtain high-affinity scFv. See, e.g., Vaughn et al., *Nat. Biotechnol.,* 14: 309-314 (1996). An scFv library with a large repertoire can be constructed by isolating V-genes from non-immunized human donors using PCR primers corresponding to all known $V_H$, $V_\kappa$ and $V_\lambda$ gene families. Following amplification, the $V_\kappa$ and $V_\lambda$ pools are combined to form one pool. These fragments are ligated into a phagemid vector. The scFv linker, $(Gly_4, Ser)_3$, is then ligated into the phagemid upstream of the $V_L$ fragment. The $V_H$ and linker-$V_L$ fragments are amplified and assembled on the $J_H$ region. The resulting $V_H$-linker-$V_L$ fragments are ligated into a phagemid vector. The phagemid library can be panned using filters, as described above, or using immunotubes (Nunc; Maxisorp). Similar results can be achieved by constructing a combinatorial immunoglobulin library from lymphocytes or spleen cells of immunized rabbits and by expressing the scFv constructs in *P. pastoris*. See, e.g., Ridder et al., *Biotechnology,* 13: 255-260 (1995). Additionally, following isolation of an appropriate scFv, antibody fragments with higher binding affinities and slower dissociation rates can be obtained through affinity maturation processes such as CDR3 mutagenesis and chain shuffling. See, e.g., Jackson et al., *Br. J. Cancer,* 78: 181-188 (1998); Osbourn et al., *Immunotechnology,* 2: 181-196 (1996).

A chimeric antibody is a recombinant protein that contains the variable domains and complementary determining regions derived from a rodent antibody, while the remainder of the antibody molecule is derived from a human antibody. Humanized antibodies are recombinant proteins in which murine complementarity determining regions of a monoclonal antibody have been transferred from heavy and light variable chains of the murine immunoglobulin into a human variable domain.

A variety of recombinant methods can be used to produce bi-specific antibodies and antibody fragments. For example, bi-specific antibodies and antibody fragments can be produced in the milk of transgenic livestock. See, e.g., Colman, A., *Biochem. Soc. Symp.*, 63: 141-147, 1998; U.S. Pat. No. 5,827,690. Two DNA constructs are prepared which contain, respectively, DNA segments encoding paired immunoglobulin heavy and light chains. The fragments are cloned into expression vectors which contain a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted fragment is flanked on its 3' side by cognate genomic sequences from a mammary-specific gene. This provides a polyadenylation site and transcript-stabilizing sequences. The expression cassettes are coinjected into the pronuclei of fertilized, mammalian eggs, which are then implanted into the uterus of a recipient female and allowed to gestate. After birth, the progeny are screened for the presence of both transgenes by Southern analysis. In order for the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

A chimeric Ab is constructed by ligating the cDNA fragment encoding the mouse light variable and heavy variable domains to fragment encoding the C domains from a human antibody. Because the C domains do not contribute to antigen binding, the chimeric antibody will retain the same antigen specificity as the original mouse Ab but will be closer to human antibodies in sequence. Chimeric Abs still contain some mouse sequences, however, and may still be immunogenic. A humanized Ab contains only those mouse amino acids necessary to recognize the antigen. This product is constructed by building into a human antibody framework the amino acids from mouse complementarity determining regions.

EXAMPLES

Example 1

IMP 272 Synthesis, Antibody Binding, and Serum Stability

The exemplary peptide IMP 272 (shown below) was synthesized and labeled with $^{111}$In as described below.

(IMP 272, MH$^+$: 1512)
DTPA-Gln-Ala-Lys(HSG)-D-Tyr-Lys(HSG)-NH$_2$

Synthesis

The peptide was synthesized by solid phase peptide synthesis on Sieber Amide resin (0.424 g, 0.53 mmol/g) using the Fmoc procedure. The following amino acids (6 equivalents per coupling) were added in the order shown; Fmoc-Lys (Aloc)-OH, Fmoc-D-Tyr(OBut)-OH, Fmoc-Lys(Aloc)-OH, Fmoc-Ala-OH and Fmoc-Gln(Trt)-OH. Each amino acid was double coupled with two hour couplings, first using diisopropylcarbodiimide, followed by a coupling using O-Benzotriazole-N,N,N',N'-tetramethyl-uronium-hexafluoro-phosphate (HBTU) as the activating agents.

The DTPA was assembled on the resin by removing the terminal Fmoc group from the glutamine, and reacting the N-terminal amino group with 0.866 g chloroacetic anhydride, 0.042 g DMAP, 1.76 mL DIEA and 5 mL NMP. The reaction was mixed for 21 hr. The resin was washed with NMP and IPA. Diethylenetriamine, 1.0 mL was mixed with 4.0 mL NMP and the solution was added to the chloroacetyl resin. The reaction was mixed for 21 hr. The resin was washed with NMP/IPA. t-Butyl bromoacetate, 1.50 mL was mixed with 2.0 mL DIEA and 3.0 mL NMP. The solution was added to the resin and mixed for 21 hr. The Aloc side chains were then removed with the Pd catalyst in the usual way and the trityl-HSG-OH was double coupled to the lysine side chains. The peptide was cleaved from the resin with TFA, precipitated in ether, and purified by HPLC to obtain the desired peptide.

IMP 272 Formulation Kit

A formulation kit containing 15 μg of IMP 272 was used in this study. This kit was made by the following procedure: Hydroxypropyl-β-cyclodextrin, 10.053 g, 0.426 g of citric acid and 0.0015 g of IMP 272 were dissolved in 85 mL of DI water. The pH of the solution was adjusted to pH 4.30 by the addition of 1 M NaOH. The solution was diluted to 100 mL with DI water. The solution was filtered through a Millex GV (0.22 μm) filter in one mL aliquots into three mL lyophilization vials. The vials were placed on dry ice to freeze solution and then lyophilized. When the lyophilization cycle was complete the vials were sealed under vacuum and removed from the lyophilizes.

Labeling $^{111}$InCl$_3$ (30.4 μL) was added to 500 μL of DI H$_2$O. This solution was added to the prepared vial of IMP 272 and allowed to sit for approximately 20 minutes at room temperature. An additional 600 μL of cold In Acetate Buffer (1.0× 10$^{-4}$M InCl$_3$, 0.5M NaOAc, pH 6.5) was then added to the same vial and allowed to sit for an additional 45 minutes. The total volume was 1130 μL with a molar quantity of 1.220× 10$^{-8}$ moles of IMP 272 yielding a concentration of 8.777× 10$^{-6}$M. After the labeling was completed, the peptide was tested for stability in fresh human and nude mouse serum over 24 hrs. The peptide was also tested for binding to humanized antibodies; m679×hMN14, and, m734×hMN14. The size exclusion and reverse phase chromatograms show that the peptide labels well and can bind hMN-14×679 and hMN-14× m734 either singly or all at once.

$^{111}$In IMP 272, 60 μL, was added to 540 μL fresh human serum. This was vortexed and placed under a constant temperature of 37° C. The peptide concentration for this mixture was 8.777×10$^{-7}$M. The peptide incubated in human serum was intact after 1 hour of incubation in human serum at 37° C. but has lost some of the binding to HSG after 24 hr at 37° C. The size exclusion HPLC indicates that about 50% of the binding to one of the two HSG's has been compromised at the 24 hr time point.

$^{111}$In IMP 272, 44 μL, was added to 400 μl fresh nude mouse serum. This was vortexed and placed under a constant temperature of 37° C. The peptide concentration for this mixture was 8.698×10$^{-7}$M. Size exclusion HPLC and reverse phase HPLC chromatograms show that the peptide is stable for 24 hr in mouse serum at 37° C.

Conclusions

The peptide, IMP 272 labeled well with $^{111}$In. In addition, after labeling, the peptide bound well to two m679×hMN14 antibodies and one m734×hMN14 antibody separately. When combined with both antibodies a shift in the retention time and broadening of the peak can be seen. When combined with mouse serum under incubation at 37° C., the peptide was stable. When combined with human serum at 37° C., the peptide is partially metabolized. One of the HSG's loses its ability to bind to the antibody.

Example 2

Clearing of Targetable Construct Using Clearing Agent (Chase)

For particular constructs, the clearing (chase) component of the lock and chase method can be tested as described herein for the IMP 272 peptide. The peptide, IMP 272 DTPA-Gln-Ala-Lys(HSG)-D-Tyr-Lys(HSG)-NH2 MH+ 1512, was made for lock and chase bispecific antibody drug targeting. The peptide contains two HSG groups to bind to antibodies at the surface of a tumor in the normal pretargeting fashion. The peptide also carries a DTPA, which (when filled with indium) binds to the m734 antibody. The IgG has two binding anus for DTPA so it can bind to two peptides bound to the tumor surface. The extra cross linking at the tumor surface extends the amount of time that the peptide remains at the tumor site. The In-DTPA cross linking by a m734 IgG antibody provides the lock in the lock and chase antibody system. If the antibody is modified with galactose then it will clear more rapidly from the bloodstream than a non-galactosylated antibody. The amount of galactose on the antibody will affect the clearance rate. High levels (30-40 gal/ab) cause the antibody to be cleared rapidly and more moderate levels (10-20 gal/ab) clears the antibody at a more moderate rate. This test is preferably carried out using 60 GW-39 tumor bearing nude mice so 65 mice should be implanted with the tumors to be sure that enough tumor bearing mice are available for the test.

Each mouse in the pretargeting arms of the study is injected with 100 µL of a solution containing 15 µg of I-125 labeled hMN-14×m679 (5 µCi/mouse). The antibody is injected 24 hours prior to the injection of the peptide.

Typically, the peptide is formulated into lyophilized kits, which contain 15 µg of peptide. The peptide is labeled with In-111 and then excess cold indium is added to saturate all the DTPA's on the peptide.

Peptide Radiolabeling

The kits are lyophilized in 3 mL vials and are reconstituted with 1 mL water (sterile water is acceptable) A 0.5 mL aliquot should be removed and mixed with 3.0 mCi In-111. The In-111 kit solution should be incubated at room temperature for 10 min. An aliquot, 117 µL, is removed and mixed with 117 µL of the cold indium containing ($1\times10^{-4}$ M In) acetate buffer (0.5 M NaOAc, pH 6.54) and then incubated at room temperature for an additional 10 min. The solution is then diluted with 6.80 mL saline in a sterile vial. The labeled peptide can be analyzed by ITLC in saturated NaCl. The loose In-111 will be at the top 20% of the ITLC strip.

Animal Studies

Group I (hMN-14×m679 Pretargeted 24 hr, IMP 272 and 25 hr m734 IgG Higal)

Inject 15 GW-39 tumor bearing nude mice with 100 µL of a solution of 15 µg (5 µCi, $1.5\times10^{-10}$ mol) hMN-14×m679. After 24 hr inject a solution of 1.5×−11 mol (10 µCi) IMP 272 in 100 µL. At 25 hr post injection of the bispecific antibody inject 12 µg ($8\times10^{-11}$ mol) m734 IgG Highly galactosylated in 100 µL. The animals, 5 per time point, should be sacrificed at 3 hr, 24 hr and 48 hr post injection of the peptide. The following organs and tissues are collected and counted: Tumor, Blood, Muscle, Liver, Lungs, Kidneys, Spleen, Large Intestine, Small Intestine, Stomach, Urine, and Tail.

Group II (hMN-14×m679 Pretargeted 24 hr, Premixed IMP 272, m734 IgG Higal)

Inject 15 GW-39 tumor bearing nude mice with 100 µL of a solution of 15 µg (5 µCi, $1.5\times10^{-10}$ mol) hMN-14×m679. After 24 hr inject a solution of $1.5\times10^{-11}$ mol (10 µCi) IMP 272 mixed with 12 µg ($8\times10^{-11}$ mol) m734 IgG (Highly galactosylated) in 100 µL. The animals, 5 per time point, should be sacrificed at 3 hr, 24 hr and 48 hr post injection of the peptide. The following organs and tissues are collected and counted: Tumor, Blood, Muscle, Liver, Lungs, Kidneys, Spleen, Large Intestine, Small Intestine, Stomach, Urine, and Tail.

Group III (hMN-14×m679 Pretargeted 24 hr, IMP 272 and 25 hr m734 IgG Modgal)

Inject 15 GW-39 tumor bearing nude mice with 100 µL of a solution of 15 µg (5 µCi, $1.5\times10^{-10}$ mol) hMN-14×m679. After 24 hr inject a solution of $1.5\times10^{-11}$ mol (10 µCi) IMP 272 in 100 µL. At 25 hr post injection of the bispecific antibody inject 12 µg ($8\times10^{-11}$ mol) m734 IgG (Moderately galactosylated) in 100 µL. The animals, 5 per time point, should be sacrificed at 3 hr, 24 hr and 48 hr post injection of the peptide. The following organs and tissues are collected and counted: Tumor, Blood, Muscle, Liver, Lungs, Kidneys, Spleen, Large Intestine, Small Intestine, Stomach, Urine, and Tail.

Group IV (hMN-14×m679 Pretargeted 24 hr, Premixed IMP 272, m734 IgG Modgal)

Inject 15 GW-39 tumor bearing nude mice with 100 µL of a solution of 15 µg (5 µCi, $1.5\times10^{-10}$ mol) hMN-14×m679. After 24 hr inject a solution of $1.5\times10^{-11}$ mol (10 µCi) IMP 272 mixed with 12 µg ($8\times10^{-11}$ mol) m734 IgG (Moderately galactosylated) in 100 µL. The animals, 5 per time point, should be sacrificed at 3 hr, 24 hr and 48 hr post injection of the peptide. The following organs and tissues should be collected and counted: Tumor, Blood, Muscle, Liver, Lungs, Kidneys, Spleen, Large Intestine, Small Intestine, Stomach, Urine, and Tail.

Example 3

Testing of Lock Component of Lock and Chase

Similar to the testing of the chase component as in the preceding example, the lock aspect of the lock and chase method can also be tested. For example, the peptide, IMP 272 DTPA-Gln-Ala-Lys(HSG)-D-Tyr-Lys(HSG)-NH$_2$ MH$^+$ 1512, was made for lock and chase bispecific antibody drug targeting. As described above, the peptide contains two HSG groups to bind to bispecific antibodies at the surface of a tumor in the normal pretargeting fashion. The peptide also carries a DTPA, which (when filled with indium) binds to the m734 antibody. The IgG has two binding arms for DTPA, and so is capable of binding to two peptides bound to the tumor surface. The extra cross linking at the tumor surface extends the amount of time that the peptide remains at the tumor site. The In-DTPA cross linking by a m734 IgG antibody provides the lock in the lock and chase antibody system. This test utilizes 50 GW-39 tumor bearing nude mice, so 55 mice should be implanted with the tumors to be sure that enough tumor bearing mice are available for the test.

Each mouse in the pretargeting arms of the study is injected with 100 µL, of a solution containing 15 µg of I-125 labeled hMN-14×m679 (5 µCi/mouse). The antibody is injected 24 hours prior to the injection of the peptide.

The peptide has been formulated into lyophilized kits, which contain 15 μg of peptide. The peptide is labeled with In-111 and then excess cold indium is added to saturate all the DTPA's on the peptide.

Peptide Radiolabeling

The kits are lyophilized in 3 mL vials and is reconstituted with 1 mL water (sterile water is OK) A 0.5 mL aliquot is removed and mixed with 3.0 mCi In-111. The In-111 kit solution is incubated at room temperature for 10 min. An aliquot, 100 μL, is removed and mixed with 100 μL of the cold indium containing acetate buffer ($1.0 \times 10^{-4}$ M $InCl_3$, 0.5M NaOAc, pH 6.5) and then incubated at room temperature for an additional 10 min. The solution is then diluted with 5.80 mL saline in a sterile vial. The labeled peptide is analyzed by ITLC in saturated NaCl. The loose In-111 will be at the top 20% of the ITLC strip.

Animal Studies

Group I (hMN-14×m679 Pretargeted 24 hr, IMP 272 and 25 hr m734 IgG)

Inject 15 GW-39 tumor bearing nude mice with 100 μL, of a solution of 15 μg (5 μCi, $1.5 \times 10^{-10}$ mol). After 24 hr inject a solution of $1.5 \times 10^{-11}$ mol (10 μCi) IMP 272 in 100 μL. At 26 hr post injection of the bispecifc antibody inject 12 μg ($8 \times 10^{11}$ mol) m734 IgG in 100 μL. The animals, 5 per time point, should be sacrificed at 3 hr, 24 hr and 48 hr post injection of the peptide. The following organs and tissues should be collected and counted: Tumor, Blood, Muscle, Liver, Lungs, Kidneys, Spleen, Large Intestine, Small Intestine, Stomach, Urine, and Tail.

Group II (hMN-14×m679 Pretargeted, 24 hr IMP 272)

Inject 15 GW-39 tumor bearing nude mice with 100 μL of a solution of 15 μg (5 μCi, $1.5 \times 10^{-10}$ mol). After 24 hr inject a solution of $1.5 \times 10^{-11}$ mol (10 μCi) IMP 272 in 100 μL. The animals, 5 per time point, should be sacrificed at 3 hr, 24 hr and 48 hr post injection of the peptide. The following organs and tissues should be collected and counted: Tumor, Blood, Muscle, Liver, Lungs, Kidneys, Spleen, Large Intestine, Small Intestine, Stomach, Urine, and Tail.

Group III (IMP 272 Alone)

Inject 20 GW-39 tumor bearing nude mice with 100 μL of a solution of $1.5 \times 10^{11}$ mol (10 μCi) IMP 272 in 100 μL. The animals, 5 per time point, should be sacrificed at 30 min, 1 hr, 3 hr, and 24 hr post injection of the peptide. The following organs and tissues should be collected and counted: Tumor, Blood, Muscle, Liver, Lungs, Kidneys, Spleen, Large Intestine, Small Intestine, Stomach, Urine, and Tail.

The following study is performed to examine the ability of the subsequent injection of an anti-In-DTPA F(ab')$_2$ antibody (734) to increase the retention of a pre-targeted defined chemical substance (DCS), known as IMP-272, on a human colonic tumor (GW-39). This concept is known as "Lock and Chase." These data will be used to calculate half-life and dosimetry of the DCS in the tumor and various other tissues and make a comparison to animals not administered the 734 F(ab')$_2$.

Example 4

Further Testing of Lock Component of Lock and Chase Application

To study the half-life of a pretargeted defined chemical substance (DCS), known as IMP-272 on a tumor, the following experiment is performed in nude mice bearing GW-39 human colorectal cancer xenografts. Animals receive three injections as follows: first injection of anti-CEA BS1.5HP diabody (hMN-14×679) followed 24 hours later with IMP-272, which is followed 3 hours later by the anti-In-DTPA F(ab')$_2$ antibody, 734. BS1.5HP is labeled with $^{125}$I and the IMP-272 is labeled with $^{111}$In. The synthesis and use of this diabody is disclosed in Clin. Cancer Res. 9:3886s-3896s (2003), and is herein incorporated in its entirety by reference. Known standard molecular biology methods were used to prepare the BS1.5HP To test for maximum cross-linking of peptide on the surface of the tumor, the total protein dose of 734 F(ab')$_2$ injected ranges from 10 μg to 100 μg. Four groups of mice are administered 10 μCi $^{125}$I-BS1.5HP (27 μg, $5.0 \times 10^{-10}$ moles) followed 24 hours later by 25 μCi $^{111}$In-IMP-272 ($5.0 \times 10^{-11}$ moles) for a bispecific:IMP-272 ratio of 10:1. IMP-272 is administered 3 hours before the administration of 734 F(ab')$_2$ to target the tumor and clear from the blood. The only differences among the groups is the amount of 734 F(ab')$_2$ administered.

Group I: Saline only control [20 mice; sac 5/time-point at 3-, 24-, 48-, and 72-hrs post-saline injection]

Group II: 10 μg total 734 F(ab')$_2$ protein dose [20 mice, sac 5/time-point at 3-, 24-, 48-, and 72-hrs post-734 injection]

Group III: 20 μg 734 F(ab')$_2$ [20 mice, sac 5/time-point at 3-, 24-, 48-, and 72-hrs post-734 injection]

Group IV: 100 μg 734 F(ab')$_2$ [20 mice, sac 5/time-point at 3-, 24-, 48-, and 72-hrs post-734 injection]

Material and Methods:

Test and Control Reagents

Dose Preparation and Analysis: The BS1.5HP as provided by Edmund Rossi, Ph. D. [Lot #011303, 1 mg/mL in 150 mM sucrose, 10 mM phosphate, pH 6.0] and the DCS IMP-272 that was prepared as lyophilized kits by William McBride, Ph. D. [Lot #BM11-154] and has the chemical formula:

IMP-272:[$^{111}$In]DTPA-Gln-Ala-Lys(HSG)-D-Tyr-Lys(HSG)-NH$_2$ (MW-1512)

DTPA=diethylenetriamine-pentaacetic acid and [$^{111}$In]DTPA is recognized by antibody 734. HSG:=histamine-succinyl-glycine group and HSG is recognized by the 679 portion of BS1.5HP.

Antibody 734 F(ab)$_2$ [Lot #052201] was derived by pepsin digestion of the 734 IgG followed by protein A and ion-exchange chromatography purification.

Radiolabeling: Sodium iodide-125 (Na$^{125}$I) obtained from NEN Life Science Products (Boston, Mass.) and Indium-111 chloride ($^{111}$InCl$_3$) obtained from IsoTex (Friendsville, Tex.) are used in these experiments. The chloromine-T method is employed for the radioiodination of the BS1.5HP with quenching by addition of excess tyrosine. Purification is accomplished by size-exclusion on a PD 10 column.

IMP-272 ($1 \times 10^{-8}$ mol peptide/kit) is labeled with $^{111}$In under metal free conditions. Briefly, the kit is reconstituted with 1 mL sterile water. A 0.6 mL aliquot of the IMP-272 is mixed with $^{111}$InCl$_3$ (3 mCi). This is followed by incubation at room temperature for 15 minutes. A 2.4 mL aliquot of cold In(OAc)$_3$ ($1.0 \times 10^{-4}$ M In, pH 4.5 buffer) is removed and mixed with the In-111 labeled peptide solution and incubated at room temperature for an additional 15 minutes. This solution is then diluted in saline to 12 mL in a sterile vial. The labeled DCS is analyzed by ITLC in saturated NaCl. Unbound $^{111}$In migrates to the top 20% of the ITLC strip.

Radiolabeled BS1.5HP is analyzed on size exclusion HPLC column before and after mixing with CEA. The IMP-272 is likewise analyzed before and after being mixed with unlabeled BS1.5HP. The following provides information regard the mice used.

Strain, sex, age, weight, source: The mice used in this study are female athymic nu/nu mice of approximately 20 grams from Taconic (Germantown, N.Y.). These mice are used because GW-39 grows in nude mice as s.c. tumors allowing for easy tracking of tumor growth so that the time of study initiation can be better determined (tumor volume ~0.2 cm$^3$). Five mice per time-point are required for statistical power. All animals were purchased as virus-free from the vendor. Animals were quarantined for a period of one week. Animals are housed in Thoren cage units with care given in accordance with CMMI approved procedures. Initial tumor volume is determined by caliper measurements in 3 dimensions and calculated by length×width×depth. Mice are placed into groups of approximately 5 animals per time-point such that they will all have tumors of similar size (mean±SD) between time-points within a group and between the groups themselves. Mice with tumors of approximately 0.2 cm$^3$ (0.2-0.5 cm$^3$) are used in this study.

Cell type and source: The human colorectal tumor, GW-39, can only be maintained as serial passage of tumors in mice. Tumors of approximately 1 cm$^3$ are serially propagated by subcutaneous injection of 0.3 mL of a 10% (w/v) tumor suspension prepared by mincing the tumors in 0.9% saline with subsequent passage through a 40-mesh wire screen. Past experience with this tumor has shown that ~17 days is required for the tumors to reach the appropriate size. The tumor size at the beginning of the study is approximately 0.2 cm$^3$.

Animals are injected i.v. via the lateral tail vein with 10 μCi of $^{125}$I-BS1.5HP diabody (27 μg; $5.0 \times 10^{10}$ moles). The study is based on past experience with this reagent in this tumor model system, which indicated that at 24 hours post-injection there should be less than 1% ID/g in the blood. At this time, 25 μCi of the $^{111}$In-IMP-272 (76 ng; $5.0 \times 10^{-11}$ moles) will be administered i.v. to the mice. After 3 hours 5 mice are necropsied. The remaining groups of mice are injected either with saline (control group) or 734 F(ab')$_2$. Total protein dose for the 734 groups ranges from 10 to 100 μg (labeled 734+"cold" 734). The injection volume is between 0.05 mL and 0.2 mL and is prepared and injected within the same time recommended for clinical use (i.e., within 6 hrs).

The following groups of animals are studied: 5 mice assigned to Group I are necropsied 3 hours post-IMP-272 injection and serve as a starting point of reference for IMP-272 tumor uptake before the administration of the 734.

Five mice per time-point (3, 24, 48, and 72 hrs) are necropsied from each group. Group I has 5 extra mice and is the only group with a 0-hour time-point (3 hrs post-IMP-272 injection) useful to determine the amount of IMP-272 targeted to the tumors and the amount in the blood at the time the 734 F(ab')$_2$ is administered. It is the starting point of reference for all 4 groups. Since these mice receive only saline and not any 734, it also serves as the control group to track the loss of IMP-272 from the tumor and normal tissues when it is not "locked" onto the surface by 734.

Mice are administered reagents i.v. to mimic the route of injection relevant to clinical application. Activities of radiolabeled products were chosen based on the time-points used in this study (3 hrs to 96 hrs post-injection) and the half-life of $^{111}$In (68 hrs) and $^{125}$I (60 days). A bispecific monoclonal antibody to IMP-272 ratio of 10:1 ($5.0 \times 10^{-10}$:$5.0 \times 10^{-11}$ moles) has been shown, and described in the *Clin. Cancer Res.* Vo. 9, 3886s-3896s, above, to result in high specific targeting of a DCS to GW-39 tumors (~20% ID/g at 3 hrs).

The selection of an amount of 734 F(ab')$_2$ to achieve maximum cross-linking of bound peptide on the tumor is important and such a dose has been predicted to be less than saturating to ensure that a single divalent molecule of 734 F(ab')$_2$ is bound to two peptides. In an effort to best determine what effect protein dose is sufficient in this system, the three doses being tested are 10 μg, 20 μg, and 100 μg. These doses were selected based on the assumption that at 3 hrs post-IMP-272, there will be approximately 20% ID/g which translates to $1 \times 10^{-11}$ moles per gram tumor. Looking at 734, there would be approximately 5% ID/g of an F(ab')$_2$ in the tumor 3 hrs post-injection. The molecular weight of 734 F(ab')$_2$ is 100,000 daltons and therefore 10 μg equals $1 \times 10^{-10}$ moles. At 5% ID/g this would equal $5 \times 10^{-12}$ moles per gram tumor, which is ½ the amount of IMP-272 that would be in the tumor. These dosages were selected to allow for maximum cross-linking. Additionally, two other groups were set up with increasing amounts of 734 F(ab)$_2$. to result in excess in the tumor relative to the IMP-272:

Injection Schedule and Calculations

Inject $5 \times 10^{-11}$ moles IMP-272 @ 3 hrs ~20% ID/g tumor=$1 \times 10^{-11}$ moles Inject $1 \times 10^{-10}$ moles 734 F(ab')$_2$ (10 μg) @ 3 hrs~5% ID/g=$5 \times 10^{-12}$ moles 734 F(ab')$_2$: IMP-272=0.5

| | | | | |
|---|---|---|---|---|
| 85 Athymic Nude Mice Inoculated s.c. with GW-39 Human Colonic Carcinoma Cells. | | | | |
| Group | Injected (N) Reagents | BS:DCS Ratio | Dose | Schedule |
| I | 25 BS1.5HP | (10:1) | 27 μg ($5.0 \times 10^{-10}$ moles) | 0 hrs |
| | IMP-272 | | 76 ng ($5.0 \times 10^{-11}$ moles) | 24 hrs post-BS1.5HP |
| | Saline (control) | | 100 μL saline | 3 hrs post-IMP-272 |
| II | 20 BS1.5HP | (10:1) | 27 μg ($5.0 \times 10^{-10}$ moles) | 0 hrs |
| | IMP-272 | | 76 ng ($5.0 \times 10^{-11}$ moles) | 24 hrs post-BS1.5HP |
| | 734 F(ab')$_2$ | | 10 μg ($1.0 \times 10^{-10}$ moles) | 3 hrs post-IMP-272 |
| III | 20 BS1.5HP | (10.1) | 27 μg ($5.0 \times 10^{-10}$ moles) | 0 hrs |
| | IMP-272 | | 76 ng ($5.0 \times 10^{-11}$ moles) | 24 hrs post-BS1.5HP |
| | 734 F(ab')$_2$ | | 20 μg ($2.0 \times 10^{-10}$ moles) | 3 hrs post-IMP-272 |
| IV | 20 BS1.5HP | (10:1) | 27 μg ($5.0 \times 10^{-10}$ moles) | 0 hrs |
| | IMP-272 | | 76 ng ($5.0 \times 10^{-11}$ moles) | 24 hrs post-BS1.5HP |
| | 734 F(ab')$_2$ | | 100 μg ($1.0 \times 10^{-9}$ moles) | 3 hrs post-IMP-272 |

Inject $2 \times 10^{-10}$ moles 734 F(ab')$_2$ (20 µg) @ 3 hrs ~5% ID/g=$1 \times 10^{-11}$ moles 734 F(ab')$_2$: IMP-272=1.0

Inject $1 \times 10^{-9}$ moles 734 F(ab')$_2$ (100 µg) @ 3 hrs ~5% ID/g=$5 \times 10^{11}$ moles 734 F(ab)$_2$: IMP-272=10.0

The animals are observed on a regular basis including evaluation of tumor sizes, paralysis and pathology evaluation and toxicity, such as blood chemistries, WBC, histology and additional routine tests and observations during the test period.

At the specified necropsy time, 5 animals are anesthetized, bled by cardiac puncture followed by cervical dislocation. Organs are removed, weighed and placed in containers. The following tissues were taken for analysis: tumor, liver, spleen, kidney, lungs, blood, stomach, small intestine, large intestine, bone (femur), washed bone (femur), and muscle. Tissues is counted in a calibrated gamma counter for $^{111}$In and $^{125}$I. A crossover curve is be generated from $^{111}$In to correct for any counts crossing over into the $^{125}$I channels. Each set of tissues is counted in conjunction with a counting standard made from the mixture of labeled and "cold" product left over from the injections. These standards are used to calculate the total injected radioactivity at any given time-point for any of the two radiolabeled reagents. Typically, this involves the preparation of a 1:100 dilution of the injected material with 0.1 mL counted. Any tissue containing >$2 \times 10^6$ cpm, is recounted at a later time when the activity has decayed sufficiently to ensure accurate determinations of radioactivity in the tissues.

The study is terminated based on criteria, such as when the tumor reaches a certain size, moribund, hind limb paralysis, pre-determined time-point, etc.): Mice are sacrificed as described above and at the times listed above.

Statistical Analysis: Comparisons between the tissues of mice injected with various doses of 734 F(ab')$_2$ or saline control utilize Student's t-test, which is performed after determining equality of variance using the f-test and a Grubbs' Critical Z test for identifying any outliers. Animals are removed as outliers based on % ID/g of the blood or tumor. These two tissues were chosen since (i) if the blood value is too low it may indicate a bad injection and will result in lower uptake of label in all tissues including the tumor, and (ii) if the tumor is not properly excised i.e. too much normal tissue present on the tumor or if it is necrotic, this too may result in an inaccurate determination of % ID/g. Even though statistical significance may be achieved with this "Lock and Chase" concept between the groups of mice receiving 734 F(ab')$_2$ and those that did not (control), for practical reasons an increase in dosimetry of greater than 50% may be necessary for further pursuit of this concept.

Example 5

Preparation and Structure of Exemplary Primary Targeting Agents

As indicated above, many different configurations of primary targeting agent can be constructed and useful in the present invention. In many cases, the agent is a bi-specific antibody design (bsAB), i.e., contains antibody binding domains specific for two different epitopes. A number of different bi-specific antibody primary targeting agents have been constructed and demonstrated to provide effective targeting, including the following examples.

Preparation of hMN14-m679

Construction of exemplary hMN14-m679 primary targeting agents (bsAB) is described in U.S. patent application Ser. No. 09/823,746 filed Apr. 3, 2001, and in Sharkey, McBride, Karacay, Chang, Griffiths, Hansen, and Goldenberg, A Universal Pre-Targeting System for Cancer Detection and Therapy Using Bispecific Antibody. *Cancer Research* 63: 354-363 (2003). Also described in those references is the use of bsAB primary targeting agents in conjunction with targetable constructs bearing an active species, and optionally in conjunction with a clearing agent.

Preparation of hMN14-734

The bispecific antibody hMN-14×734 was prepared by coupling an equal amount of the Fab' fragment of the humanized anti-CEA antibody (hMN-14) to the Fab' fragment of the murine anti-indium-DTPA antibody (734) activated by o-phenylene-bismaleimide, followed by purification over a Ca-DTPA column (to remove unconjugated hMN-14 specific) and a Supredex-200 column (to obtain the 100-kD product). The immunoreactivity of the bispecific conjugate for CEA was evaluated on size-exclusion HPLC by measuring the fraction of a radioiodinated sample that is shifted, in the presence of excess CEA, toward shorter retention time as a result of binding to CEA. The immunoreactivity was generally 85% or better. The ability of the bispecific conjugate to bind to the radiolabeled peptide was similarly demonstrated on size-exclusion HPLC by noting the shift of the radiolabeled peptide toward shorter retention time upon adding the bispecific conjugate.

Example 6

Preparation and Structure of Exemplary Clearing Agent

An exemplary clearing agent includes an anti-DTPA IgG antibody (m734 IgG). The m734 IgG is galactosylated by the method of Karacay et. al. *Bioconjugate Chem.*, 1997, 8, 585-594. The CTTG (0.23 g, $5.7 \times 10^{-5}$ mol) is dissolved in 6.2 mL of anhydrous methanol. Sodium methoxide, 0.5 M in methanol (115 µl, $5.75 \times 10^{-5}$ mol), is added to the above solution under argon and stirred at room temperature for 18 hr. The imidate is used immediately, or stored at 4° C. To galactosylate lysine residues on m734 IgG, imidate corresponding to various imidate:m734 IgG molar ratios are evaporated using a stream of argon. The antibody, m734 IgG, is added to each, the final protein concentration adjusted to 8.4 mg/mL by addition of 0.1 M sodium phosphate at pH 8.1, and the final pH is adjusted to 8.5-8.6 with a saturated solution of tribasic sodium phosphate. Reaction Mixtures are stirred at room temperature for 2 hr, and the modified m734 IgG's are purified on two consecutive sets of centrifuged spin columns packed with Sephadex G-50-80 in 0.1 M sodium phosphate at pH 7.3. Galactosylated m734 IgG samples are analyzed by MALDI-MS to determine the exact number of galactose residues present.

Example 7

Exemplary Lock and Chase Targeted Delivery

The bispecific antibody, hMN-14×m679 (15 µg in 100 µL PBS/per mouse) is injected into the GW-39 tumor bearing nude mice. The antibody is allowed to clear for 24 hr and the In-111 labeled IMP 272 (10 µCi/mouse in 100 µL, labeled as described previously). The galactosylated m734 IgG (25-30 µg in 100 µL PBS/per mouse) at 15 (Group A) and 30 min (Group B) post injection of the peptide. The animals (five per time point in each group) are sacrificed at 3 hr, 24 hr, 48 hr, and 72 hr. The targeting in Groups A & B will be compared to a control (Group C) which received the irrelevant galactosylated antibody Ag8 after injection of the peptide.

Example 8

Exemplary Targeted Delivery with Internalization

Therapy of B-Cell Lymphoma with Internalization by Cross-Linking to Rapidly Internalizing Surface Antigen A patient having B-cell lymphoma with extensive node involvement is infused intraveneously with a sterile, pyrogen-free solution containing a target dose of bispecific hA20Fab-679scFv prepared as described in U.S. application Ser. Nos. 09/337,756 and 60/360,229. After 24 hours, the patient then is infused intraveneously with a sterile, pyrogen-free PBS solution that contains a therapeutic dose of DTPA-Gln-Ala-Lys(HSG)-D-[I-131Tyr]-Lys(HSG)-$NH_2$. After 24 hours the patient then is intraveneously infused with 50 mg of sterile, pyrogen-free PBS solution of bispecific hLL1IgG[734scFv]. Rapid clearance of I-131 from the blood is observed, and subsequent radioimmunodetection demonstrates intensive localization and long retention of I-131 in the lymphoma involved nodes. CAT scans over the next few months demonstrate significant reduction in the size of the lymphoma-involved nodes. This administration is illustrated schematically in FIG. 6-9.

Targeted Delivery with Internalization Using Folate Receptor

Synthesis of Folic acid m734 IgG

Proteins, such as m734 IgG can be derivatized with folic acid by the method of Reddy et. al. *Blood,* 1999, 93, 3940-3948. Folic acid (10 mg) is dissolved in anhydrous DMSO and incubated under stirring with 25 mg 1-ethyl-3-(dimethylaminopropyl)carbodiimide for 30 min at room temperature. An aliquot (⅓ of the solution) of the solution is then added to 100 mg of m734 IgG (~10 mg/mL) in PBS at pH 7.4. After a 2 hr incubation with stirring at room temperature the reaction mixture is passed through a PD-10 desalting column equilibrated in PBS to separate the conjugated protein from excess free folic acid.

The antibody conjugate is analyzed by MALDI-MS to determine the exact number of folic acid residues per antibody.

Test of In-vivo Targeted Delivery With Folate Receptor Internalization

The bispecific antibody, hMN-14×m679 (15 μg in 100 μL PBS/per mouse) is injected into the GW-39 tumor bearing nude mice. The antibody is allowed to clear for 24 hr and the In-111 labeled IMP 272 (10 μCi/mouse in 100 μL, labeled as described previously) is then injected. The folic acid modified m734 IgG (25-30 μg in 100 μL PBS/per mouse) at 30 min (Group A) post injection of the peptide. The animals (five per time point in each group) are sacrificed at 3 hr, 24 hr, 48 hr, and 72 hr. The targeting in Group A is compared to a control (Group B) which received the unmodified m734 IgG and (Group C) the irrelevant folic acid modified antibody Ag8 after injection of the peptide.

Test of In-vitro Targeted Delivery with Folate Receptor Internalization

CEA expressing cells such as LoVo or TT cells are incubated for 1 hr with hMN-14×m679 and $^{111}$In/In DTPA-Gln-Ala-Lys(HSG)-D-Tyr-Lys(HSG)-$NH_2$ (IMP 272) [two antibodies to one peptide molar ratio]. The cells are then washed with fresh serum and incubated for 4 hr with the folic acid modified antibody and the control antibodies unmodified m734 IgG and folic acid modified Ag8 (each antibody incubation in separate wells). The cells will are then washed with fresh serum and the internalization of the peptide is examined at 30 min, 1 hr, 2 hr, 4 hr, 8 hr, 24 hr, 48 hr and 72 hr post incubation.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the invention.

It will be readily apparent to one skilled in the art that varying substitutions and modifications may be made to the invention disclosed herein without departing from the scope and spirit of the invention. For example, a variety of different binding pairs can be utilized, as well as a variety of different therapeutic and diagnostic agents. Thus, such additional embodiments are within the scope of the present invention.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention. For example, the invention is further illustrated by the following numbered embodiments:

We claim:

1. A kit comprising:
 a) a bispecific antibody comprising at least one target binding moiety that binds to a tumor-associated marker selected from the group consisting of carcinoembryonic antigen (CEA), colon-specific antigen-p (CSAp), CD4, CD5, CD8, CD14, CD15, CD19, CD20, CD22, CD40, CD40L, CD74, B7, HLA-DR, EGFR, HER 2/neu, TAG-72, EGP-1, HCG, HCG-beta, PSMA, PSA, VEGF, IL-2 and MAGE and at least one first targetable construct binding moiety that binds to a hapten selected from the group consisting of HSG (histamine succinyl glycine) and In-DTPA;
 b) a targetable construct comprising a first hapten that is HSG and a second hapten that is In-DTPA, wherein said targetable construct comprises at least one therapeutic or diagnostic agent; and
 c) an internalization agent comprising a second targetable construct binding moiety that binds to a hapten selected from the group consisting of HSG and In-DTPA and an internalization moiety selected from the group consisting of an anti-CD74 antigen-binding antibody fragment and a folate;
wherein said first and second targetable construct binding moieties bind to different haptens and wherein binding of the internalization agent to the second targetable construct enhances internalization of the diagnostic or therapeutic agent.

2. The kit of claim 1, wherein said target binding moiety, first targetable construct binding moiety, second targetable construct binding moiety and internalization moiety are antibody fragments selected from the group consisting of F(ab')$_2$, Fab', Fab, Fv, sFy and scFv antibody fragments.

3. The kit of claim 2, wherein said internalization moiety is an anti-CD74 antigen-binding antibody fragment.

4. The kit of claim 3, wherein said anti-CD74 antibody fragment is an LL1 antibody fragment.

5. The kit of claim 2, wherein said antibody fragment is a fragment of a humanized antibody, chimeric antibody, human antibody or murine antibody.

6. The kit of claim 1, wherein said HSG binding moiety is a 679 antibody fragment and said In-DTPA binding moiety in a) and c) is a 734 antibody fragment.

7. The kit of claim 1, wherein said therapeutic agent is selected from the group consisting of a drug, a prodrug, a toxin, an enzyme, an enzyme that activates a prodrug to a drug, an enzyme-inhibitor, a nuclease, a hormone, a hormone antagonist, an immunomodulator, a boron compound, a photoactive agent a dye and a radionuclide.

8. The kit of claim 7, wherein said therapeutic agent is selected from the group consisting of aplidin, azaribine, anastrozole, azacytidine, bleomycin, bortezomib, bryostatin-1, busulfan, camptothecin, 10-hydroxycamptothecin, carmustine, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, semustine streptozocin, tamoxifen, taxanes, taxol, testosterone propionate, thalidomide, thioguanine, thiotepa, teniposide, topotecan, uracil mustard, vinblastine, vinorelbine, vincristine, ricin, abrin, ribonuclease, rapLR1, DNase I, *Staphylococcal* enterotoxin-A, pokeweed antiviral protein, gelonin, diphtheria toxin, *Pseudomonas* exotoxin, *Pseudomonas* endotoxin, nitrogen mustard, ethyleneimine derivative, alkyl sulfonate, nitrosourea, triazene, folic acid, anthracycline, COX-2 inhibitor, pyrimidine analog, purine analog, antibiotic, epipodophyllotoxin, platinum coordination complex, vinca alkaloid, substituted urea, methyl hydrazine derivative, adrenocortical suppressant, endostatin, cytokine, interleukin, interferon, lymphokine, and tumor necrosis factor.

9. The kit of claim 7, wherein said radionuclide is selected from the group consisting of $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{75}$Se, $^{77}$As, $^{86}$Y, $^{89}$Zr, $^{90}$Y, $^{94}$Tc, $^{94m}$Tc, $^{99}$Mo, $^{99m}$Tc, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154\text{-}158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{192}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac.

10. The kit of claim 1, wherein said diagnostic agent is selected from the group consisting of a photoactive agent or dye, a radionuclide, a radio-opaque material, a contrast agent, and a fluorescent compound.

11. The kit of claim 10, wherein said radionuclide is selected from the group consisting of $^{18}$F, $^{45}$Ti, $^{52}$Fe, $^{62}$Cu, $^{64}$Cu, $^{67}$Cu, $^{67}$Ga, $^{90}$Y, $^{99m}$Tc, $^{111}$Ag, $^{111}$In, $^{125}$I, $^{131}$I, $^{142}$Pr, $^{153}$Sm, $^{161}$Tb, $^{166}$Dy, $^{166}$Ho, $^{177}$Lu, $^{186}$Re, $^{188}$Re, $^{189}$Re, $^{211}$At, $^{212}$Bi, $^{212}$Pb, $^{213}$Bi, $^{223}$Ra and $^{225}$AC.

12. A kit comprising:
   a) a primary targeting agent comprising a first bispecific antibody that binds to a tumor-associated antigen (TAA) and to a first hapten, wherein the first hapten is selected from the group consisting of HSG (histamine-succinyl-glycine) and In-DTPA and wherein the TAA is selected from the group consisting of carcinoembryonic antigen (CEA), colon-specific antigen-p (CSAp), CD4, CD5, CD8, CD14, CD15, CD19, CD20, CD22, CD40, CD40L, CD74, B7, HLA-DR, EGFR, HER 2/neu, EGP-1, HCG, HCG-beta, PSMA, PSA, VEGF, IL-2, and MAGE;
   b) a targetable construct comprising at least one therapeutic or diagnostic agent, a first hapten and a second hapten, each hapten selected from the group consisting of HSG and In-DTPA, wherein the first and second haptens are different; and
   c) an internalization agent comprising a second bispecific antibody that binds to said second hapten and to CD74;
wherein the targetable construct and the internalization agent are administered after the primary targeting agent.

13. The kit of claim 12, wherein the second bispecific antibody comprises an hLL1 antibody or antigen-binding fragment thereof.

14. The kit of claim 12, wherein the TAA is CEA, the first bispecific antibody is hMN-14×679, the targetable construct comprises two HSG haptens and one In-DTPA hapten and the second bispecific antibody is hLL1×734.

15. The kit of claim 14, wherein the second bispecific antibody comprises two copies of hLL1 and one copy of 734, or two copies of 734 and one copy of hLL1.

* * * * *